United States Patent
Deisher

(10) Patent No.: US 11,446,314 B2
(45) Date of Patent: *Sep. 20, 2022

(54) IMMUNOABLATIVE THERAPIES

(71) Applicant: AVM Biotechnology LLC, Seattle, WA (US)

(72) Inventor: Theresa Deisher, Seattle, WA (US)

(73) Assignee: AVM Biotechnology, LLC, Seattle, WA (US)

( * ) Notice: Subject to any disclaimer, the term of this patent is extended or adjusted under 35 U.S.C. 154(b) by 417 days.

This patent is subject to a terminal disclaimer.

(21) Appl. No.: 16/227,068

(22) Filed: Dec. 20, 2018

(65) Prior Publication Data

US 2020/0108078 A1 Apr. 9, 2020

(30) Foreign Application Priority Data

Oct. 3, 2018 (EP) .................... 18198491

(51) Int. Cl.
| | |
|---|---|
| *A61K 31/573* | (2006.01) |
| *A61K 9/00* | (2006.01) |
| *A61K 47/54* | (2017.01) |
| *A61P 25/14* | (2006.01) |
| *A61P 37/06* | (2006.01) |
| *A61P 31/18* | (2006.01) |
| *A61P 3/10* | (2006.01) |
| *A61P 35/00* | (2006.01) |
| *C07K 16/42* | (2006.01) |

(52) U.S. Cl.
CPC .......... *A61K 31/573* (2013.01); *A61K 9/0019* (2013.01); *A61K 9/0053* (2013.01); *A61K 47/547* (2017.08); *A61P 3/10* (2018.01); *A61P 25/14* (2018.01); *A61P 31/18* (2018.01); *A61P 35/00* (2018.01); *A61P 37/06* (2018.01); *C07K 16/4283* (2013.01)

(58) Field of Classification Search
CPC .. A61K 31/573; A61K 9/0019; A61K 9/0053; A61K 47/547; A61P 25/14; A61P 31/18; A61P 35/00; A61P 37/06; A61P 3/10; C07K 16/4283
See application file for complete search history.

(56) References Cited

U.S. PATENT DOCUMENTS

| | | | |
|---|---|---|---|
| 3,368,937 A * | 2/1968 | Macek ................ | A61K 31/44 514/125 |
| 5,728,388 A | 3/1998 | Terman | |
| 7,282,722 B2 | 10/2007 | Phillips | |
| 8,030,469 B2 | 10/2011 | Aoyagi et al. | |
| 9,855,298 B2 | 1/2018 | Bot et al. | |
| 9,962,408 B2 | 5/2018 | Deisher | |
| 10,426,740 B1 | 10/2019 | Deisher | |
| 2002/0006409 A1 | 1/2002 | Wood | |
| 2004/0247574 A1 | 12/2004 | Christopherson et al. | |
| 2006/0233766 A1 | 10/2006 | Messina et al. | |
| 2007/0196331 A1 | 8/2007 | Phillips et al. | |
| 2007/0243173 A1 | 10/2007 | Phillips | |
| 2007/0243174 A1 | 10/2007 | Phillips et al. | |
| 2007/0243175 A1 | 10/2007 | Phillips et al. | |
| 2007/0248577 A1 | 10/2007 | Phillips et al. | |
| 2009/0047263 A1 | 2/2009 | Yamanaka et al. | |
| 2009/0220583 A1 * | 9/2009 | Pereswetoff-Morath | A61K 9/127 424/450 |
| 2009/0299269 A1 | 12/2009 | Foley et al. | |
| 2010/0047215 A1 | 2/2010 | Phillips et al. | |
| 2011/0091434 A1 | 4/2011 | Miller et al. | |
| 2013/0287747 A1 | 10/2013 | Minning et al. | |
| 2013/0287748 A1 | 10/2013 | June et al. | |
| 2014/0050708 A1 | 2/2014 | Powell et al. | |
| 2014/0099309 A1 | 4/2014 | Powell, Jr. et al. | |
| 2014/0154228 A1 | 6/2014 | Volk et al. | |
| 2014/0227237 A1 | 8/2014 | June et al. | |
| 2018/0142015 A1 | 5/2018 | De Min et al. | |
| 2018/0296572 A1 | 10/2018 | Deisher | |

FOREIGN PATENT DOCUMENTS

| | | | |
|---|---|---|---|
| EP | 3490605 A1 | 6/2019 | |
| WO | 9513093 A1 | 5/1995 | |
| WO | 2003047616 A1 | 6/2003 | |
| WO | 03096970 A2 | 11/2003 | |
| WO | 2003097052 A2 | 11/2003 | |
| WO | 2004098644 A1 | 11/2004 | |
| WO | 2008081035 A1 | 7/2008 | |
| WO | 2008094689 A2 | 8/2008 | |
| WO | 2009152186 A1 | 12/2009 | |
| WO | 2012024519 A2 | 2/2012 | |
| WO | 2016191756 A1 | 12/2016 | |
| WO | 2018153984 A1 † | 8/2018 | |
| WO | WO-2018153984 A1 * | 8/2018 | ............. A61K 45/06 |

(Continued)

OTHER PUBLICATIONS

Sinha et. al., Indian Journal of Pediatrics, 2008, vol. 75(10), pp. 1057-1066 (Year: 2008).*

Goldenberg, P&T, vol. 37(3), pp. 175-184, publ. Mar. 2012 (Year: 2012).*

Atkinson et al., Lancet, vol. 383, pp. 68-82, publ. Jul. 2013 (Year: 2013).*

Shiel et. al., "Scleroderma", MedicineNet, publ. https://www.medicinenet.com/scleroderma/article.htm, publ. Oct. 21, 2020 (Year: 2020).*

CDC, https://www.cdc.gov/dotw/als/index.html, publ. Apr. 30, 2021 (Year: 2021).*

(Continued)

*Primary Examiner* — Sarah Pihonak

(74) *Attorney, Agent, or Firm* — McNeill Baur PLLC

(57) ABSTRACT

This invention pertains to pharmaceutical compositions comprising a glucocorticoid for use in the treatment of diseases by immunoablation. The compositions of the invention may be for use in the treatment of diseases that are mediated by immune cells such as lymphocytes.

14 Claims, 25 Drawing Sheets

(56) References Cited

FOREIGN PATENT DOCUMENTS

| | | |
|---|---|---|
| WO | 2018183927 | 10/2018 |
| WO | 2018183927 A1 | 10/2018 |

OTHER PUBLICATIONS

Activate clinical trial, clinical trial identifier: NCT03158935; https://clinicaltrials.gov/ct2/show/NCT03158935, first posted May 18, 2017.
Aicher et al., "Assessment of the Tissue Distribution of Transplanted Human Endothelial Progenitor Cells by Radioactive Labeling," Circulation, 107(16):2134-9 (PMID: 12695305) (2003).
Aker, A. M. et al. Phenols and parabens in relation to reproductive and thyroid hormones in pregnant women. Environ. Res. 151, 30-37 (2016).
Alenzi et al., "Stem cells: Biology and clinical potential", 2011, African Journal of Biotechnology, vol. 10(86), pp. 19929-19940.
Alexander, T. et al. Hematopoietic stem cell therapy for autoimmune diseases—Clinical experience and mechanisms. J. Autoimmun. 92, 35-46 (2018).
American Diabetes Association. Diagnosis and classification of diabetes mellitus. Diabetes Care 37 Suppl 1, S81-90 (2014).
Atkinson, M. A., Eisenbarth, G. S. & Michels, A. W. Type 1 diabetes. Lancet 383, 69-82 (2014).
Barbash et al., "Systemic Delivery of Bone Marrow-Derived Mesenchymal Stem Cells to the Infarcted Myocardium," Circulation, 108:863-8 (PMID: 12900340), (2003).
Barbosa Da Fonseca et al., "Migration and homing of bone-marrow mononuclear cells in chronic ischemic stroke after intra-arterial injection," Exp Neurol, 221(1):122-8 (PMID: 19853605), (2010).
Bierer et al., "Cyclosporin A and FK506: molecular mechanisms of immunosuppression and probes for transplantation biology", Current Opinion in Immunology 1993, 5:763-773.
Bone, R. N. & Evans-Molina, C. Combination Immunotherapy for Type 1 Diabetes. Curr. Diab. Rep. 17, 50 (2017).
Boroujeni et al., "Transplantation and Homing of Mouse Embryonic Stem Cells Treated with Erythropoietin in Spleen and Liver of Irradiated Mice," Iran Biomed J, 13(2):87-94 (PMID: 19471548), (2009).
Bracci et al., "Cyclophosphamide enhances the antitumor efficacy of adoptively transferred immune cells through the induction of cytokine expression, B-cell and T-cell homeostatic proliferation, and specific tumor infiltration", Clin Cancer Research, vol. 113. No. 2. Jan. 15, 2007 pp. 644-653.
Braitch et al., "Glucocorticoids increase CD4+CD25high cell percentage and Foxp3 expression in patients with multiple sclerosis", Acta Neurol Scand. Apr. 2009; 119(4): 239-245. doi:10.1111/j.1600-0404.2008.01090.x.
Brendolan et al., "Development and function of the mammalian spleen", BioEssays, 2007, 29:166-177.
Broder, M. S. et al. The Cost of Hematopoietic Stem-Cell Transplantation in the United States. Am. Heal. drug benefits 10, 366-374 (2017).
Burger, J. A. & Montserrat, E., Coming full circle: 70 years of chronic lymphocytic leukemia cell redistribution, from glucocorticoids to inhibitors of B-cell receptor signaling; Blood 2013 vol. 121 No. 9 1501-1509, doi: 10.1182/blood-2012-08-452607 (2013).
Cantu-Rodriguez, O. G. et al. Long-Term Insulin Independence in Type 1 Diabetes Mellitus Using a Simplified Autologous Stem Cell Transplant. J. Clin. Endocrinol. Metab. 101, 2141-2148 (2016).
Cell Therapy Catapult Phase I/II Study of Gene-modified WT1 TCR Therapy in MDS & AML Patients (https://clinicaltrials.gov/ct2/show/NCT02550535), first posted Sep. 15, 2015.
Chang et al., "Egress of CD19 CD5 cells into peripheral blood following treatment with the Bruton tyrosine kinase inhibitor ibrutinib in mantle cell lymphoma patients", Blood. Oct. 3, 2013; 122(14): 2412-2424.
Chatenoud et al., "Adaptive human regulatory T cells: myth or reality?", J. Clin. Invest. 116:2325-2327 (2006). doi:10.1172/JCI29748.
Cheadle et al., "Differential Role of Th1 and Th2 Cytokines in Autotoxicity Driven by CD19-Specific Second-Generation Chimeric Antigen Receptor T Cells in a Mouse Model", J Immunol 2014; 192:3654-3665; Prepublished Online Mar. 12, 2014; doi: 10.4049/jimmunol.1302148.
Chen et al., "Cyclosporine-assisted adipose-derived mesenchymal stem cell therapy to mitigate acute kidney ischemia—reperfusion injury," Stem Cell Res Ther, 4(3):62 (PMID: 23726287) (2013).
Childs et al. "Regression of Metastatic Renal-Cell Carcinoma after Nonmyeloablative Allogeneic Peripheral-Blood Stem-Cell Transplantation." New England J. Med., 2000, vol. 343, pp. 750-758.
Couri, C. E. B., Malmegrim, K. C. R. & Oliveira, M. C. New Horizons in the Treatment of Type 1 Diabetes: More Intense Immunosuppression and Beta Cell Replacement. Front. Immunol. 9, 1086 (2018).
Craddock et al., "The Immune Response to Foreign Red Blood Cells and the Participation of Short-Lived Lymphocytes," J Exp Med, 125:1149-72 (PMID: 6025321) (1967).
Daikeler, T., Tichelli, A. & Passweg, J. Complications of autologous hematopoietic stem cell transplantation for patients with autoimmune diseases. Pediatr. Res. 71, 439-444 (2012).
Darbre, P. D. & Harvey, P. W. Parabens can enable hallmarks and characteristics of cancer in human breast epithelial cells: a review of the literature with reference to new exposure data and regulatory status. J. Appl. Toxicol. 34, 925-938 (2014).
Defranco, A. L. Germinal centers and autoimmune disease in humans and mice. Immunol. Cell Biol. 94, 918-924 (2016).
Dudley et al. "A Phase I Study of Nonmyeloablative Chemotherapy and Adoptive Transfer of Autologous Tumor Antigen-Specific T Lymphocytes in Patients With Metastatic Melanoma", Journal of Immunotherapy, vol. 25, No. 3, Jan. 1, 2002 (Jan. 1, 2002), pp. 243-251.
Elmore, Susan, "Enhanced Histopathology of the Spleen", Toxicologic Pathology, 34:648-655, 2006.
Ettinger et al., "Effects of tumor necrosis factor and lymphotoxin on peripheral lymphoid tissue development," Int Immunol, 10(5):727-41 (PMID: 9678753), (1998).
Facui AS. Mechanisms of corticosteroid action on lymphocyte subpopulations. II. Differential effects of in vivo hydrocortisone, prednisone and dexamethasone on in vitro expression of lymphocyte function. Clinical and Experimental Immunology; 24(1):54-62 (1976).
Fehervari and Sakaguchi, "Development and function of CD25+ CD4+ regulatory T cells", Current Opinion in Immunology 2004, 16:203-208.
File History of U.S. Appl. No. 15/973,438, Sep. 12, 2019.
File History of U.S. Appl. No. 15/976,630, Jan. 7, 2020.
Flammer, J. R. & Rogatsky, I. Minireview: Glucocorticoids in autoimmunity: unexpected targets and mechanisms. Mol. Endocrinol. 25, 1075-1086 (2011).
Gaur and Ganguly, "Effect of Single Dose Betamethasone Administration in Pregnancy on Maternal and Newborn Parameters", Journal of Clinical and Diagnostic Research. May 2017, vol. 11(5): FC15-FC18.
Gholamrezanezhad et al., "In vivo tracking of 111 In-oxine labeled mesenchymal stem cells following infusion in patients with advanced cirrhosis," Nucl Med Biol, 38:961-7 (PMID: 21810549), (2011).
Haba et al., "An immunohistochemical study on the effects of cyclosporin on the gut-associated lymphoid tissue of rats," Gastroenterol Jpn, 26(5):593-602 (PMID: 1836439), (1991).
Haddad-Mashadrizeh et al., Evidence for crossing the blood barrier of adult rat brain by human adipose-derived mesenchymal stromal cells during a 6-month period of post-transplantation, Cytotherapy, 15:951-60 (PMID: 23732047), (2013).
Henderson et al., "Comparison of the effects of FK-506, cyclosporin A and rapamycin on IL-2 production", Immunology, 1991, 73:316-321.
Henig, I. & Zuckerman, T. Hematopoietic stem cell transplantation—50 years of evolution and future perspectives. Rambam Maimonides Med. J. 5, e0028 (2014).
Hinrichs, Glucocorticoids Do Not Inhibit Antitumor Activity of Activated CD8+ T Cells, J Immunother. Nov.-Dec. 2005;28(6):517-24.

(56) References Cited

OTHER PUBLICATIONS

International Search Report and Written Opinion dated Aug. 10, 2018 in PCT/US2018/025517 (13 pages).
Jackson et al., "Tirilazad Mesylate—Effects of the 21-Aminosteriod on the Lymphoid System of Laboratory Animals: A Comparison with the Glucocorticoid Methylpredinsolone," Fund. & Appl Toxicol, 26:246-57 (PMID: 7589913), (1995).
Jasmin et al., "Mesenchymal Bone Marrow Cell Therapy in a Mouse Model of Chagas Disease. Where Do the Cells Go?," PLoS Negl Trop Dis, 6(12):e1971 (2012).
Kalos et al., "T cells with chimeric antigen receptors have potent antitumor effects and can establish memory in patients with advanced leukemia." Sci Transl Med. Aug. 10, 2011;3(95):95ra73. doi: 10.1126/scitranslmed.3002842.
Kang et al., "Tissue Distribution of 18F-FDG-Labeled Peripheral Hematopoietic Stem Cells After Intracoronary Administration in Patients with Myocardial Infarction," J Nucl Med, 47(8):1295-301 (PMID: 16883008), (2006).
Kershaw et al., "A Phase I Study on Adoptive Immunotherapy Using Gene-Modified T Cells for Ovarian Cancer", Clin Cancer Res 2006;12(20) Oct. 15, 2006, pp. 6106-6115.
Ulrich et al., "Validation of immune function testing during a 4-week oral toxicity study with FK506", Toxicology Letters 149 (2004) 123-131.
Voltarelli et al., Autologous nonmyeloablative hematopoietic stem cell transplantation in newly diagnosed type 1 diabetes mellitus. JAMA 297, 1568-1576 (2007).
Wang et al., "Early administration of tumor necrosis factor-alpha antagonist promotes survival of transplanted neural stem cells and axon myelination after spinal cord injury in rats," Brain Res, 1575:87-100 (PMID: 24887643), (2014).
Wu et al., "Cell delivery in cardiac regenerative therapy.", 2012, Aging Research reviews, vol. 11, p. 32-40.
Zwang, Homeostatic expansion as a barrier to lymphocyte depletion strategies, Curr Opin Organ Transplant. 19(4): 357-362 (2014).
Yan et al., "Prednisone treatment inhibits the differentiation of B lymphocytes into plasma cells in MRL/MpSlac-lpr mice", Acta Pharmacologica Sinica (2015) 36: 1367-1376.
Zhang et al., "Repeated System Administration of Human Adipose-Derived Stem Cells Attenuates Overt Diabetic Nephropathy in Rats," Stem Cells Dev, 22:3074-86 (PMID: 23844841), (2013).
Kim, J. H., Jin, S.-M., Kim, H. S., Kim, K.-A. & Lee, M.-S. Immunotherapeutic treatment of autoimmune diabetes. Crit. Rev. Immunol. 33, 245-281 (2013).
Klingemann et al., "Autologous Stem Cell Transplant Recipients Tolerate Haploidentical Related-Donor Natural Killer Cell Enriched Infusions", Transfusion. Feb. 2013; 53(2): 412-418. doi:10.1111/j.1537-2995.2012.03764.x.
Kolf et al., "Mesenchymal stromal cells. Biology of adult mesenchymal stem cells: regulation of niche, self-renewal and dlifferentiation", 2007, Arthritis Research & Therapy, vol. 9, p. 204, 10 pages.
Kreisel et al. "Complete remission of Crohn's disease after high-dose cyclophosphamide and autologous stem cell transplantation." Bone Marrow Transplantation, 2003, vol. 32, pp. 337-340.
Kunder et al., "A Comprehensive Antibody Panel for Immunohistochemical Analysis of Formalin-Fixed, Paraffin-Embedded Hematopoietic Neoplasms of Mice: Analysis of Mouse Specific and Human Antibodies Cross-Reactive with Murine Tissue", Toxicologic Pathology, 35:366-375, 2007.
Li et al., "Xenotransplantation: role of natural immunity.", 2009, Transplant Immunology, vol. 21, p. 70-74 (Abstract).
Lin et al., Pharmacological Mobilization of Endogenous Stem Cells Significantly Promotes Skin Regeneration after Full Thickness Excision: The Synergistic Activity of AMD3100 and Tacrolimus, J Invest Dermatol, 134(9):2458-2468 (2014).
Liu et al., "Calcineurin Is a Common Target of Cyclophilin-Cyclosporin A and FKBP-FK506 Complexes", Cell, vol. 66, 807-815, Aug. 23, 1991.

Loh, Y. et al. Development of a secondary autoimmune disorder after hematopoietic stem cell transplantation for autoimmune diseases: role of conditioning regimen used. Blood 109, 2643-2648 (2007).
Lu, Y., Suzuki, J., Guillioli, M., Umland, O., & Chen, Z. Induction of self-antigen-specific Foxp3+ regulatory T cells in the periphery by lymphodepletion treatment with anti-mouse thymocyte globulin in mice. Immunology 134, 50-59 (2011).
Magdalena, W. et al. Lack of persistent remission following initial recovery in patients with type 1 diabetes treated with autologous peripheral blood stem cell transplantation. Diabetes Res. Clin. Pract. 143, 357-363 (2018). doi:10.1016/j.diabres.2018.07.020.
Malmegrim, K. C. R. et al. Immunological Balance Is Associated with Clinical Outcome after Autologous Hematopoietic Stem Cell Transplantation in Type 1 Diabetes. Front. Immunol. 8, 167 (2017).
Mathian et al., "Regulatory T Cell Responses to High-Dose Methylprednisolone in Active Systemic Lupus Erythematosus". 2015, PLoS ONE 10(12): e0143689. doi:10.1371/journal.pone.0143689.
Matsumoto et al., "Role of Lymphotoxin and the Type I TNF Receptor in the Formation of Germinal Centers," Science Reports, 271:1289-91 (1996).
Menke, A. et al. The prevalence of type 1 diabetes in the United States. Epidemiology 24, 773-774 (2013).
Miller et al., "Resistance of Long-Lived Lymphocytes and Plasma Cells in Rat Lymph Nodes to Treatment with Prednisone, Cyclophosphamide, 6-Mercaptopurine, and Actinomycin D," J Exp Med, 126:109-25 (PMID: 6027642) (1967).
Moriyama et al., "Pathological Effects in Lymphoid Tissues of the Spleen, Lymph Nodes, and Peyer's Patches in Cyclosporin-Treated Cynomolgus Monkeys", J. Vet. Med. Sci. 74(11): 1487-1491, 2012.
Muranski et al., "Increased intensity lymphodepletion and adoptive immunotherapy—how far can we go?", Nat Clin Pract Oncol. Dec. 2006;3(12):668-81.
Murray et al., "Overproduction of corticotropin-releasing hormone blocks germinal center formation: role of corticosterone and impaired follicular dendritic cell networks," J Neuroimmunol, 156:31-41 (PMID: 15465594) (2004).
Wulffraat et al., "Prolonged remission without treatment after autologous stem cell transplantation for refractory childhood systemic lupus erythematosus". Arthritis & Rheumatism, 2001, vol. 44, pp. 728-731.
Orem, J., et al. Burkitt's Lymphoma in Africa, a Review of the Epidemiology and Etiology, African Health Sciences, vols. 7.3: 166-175 (2007).
Pallera, A. M. & Schwartzberg, L. S. Managing the toxicity of hematopoietic stem cell transplant. J. Support. Oncol. 2, 223-228-247 (2004) (Abstract).
Pasparakis et al., "Immune and Inflammatory Responses in TNFα-deficient Mice: A Critical Requirement for TNFα in the Formation of Primary B Cell Follicles, Follicular Dendritic Cell Networks and Germinal Centers, and in the Maturation of the Humoral Immune Response," J Exp Med, 184:1397-411 (PMID: 8879212), (1996).
Pasricha, J. Current regimen of pulse therapy for pemphigus: Minor modifications, improved results. Indian J Dermatol Venereol Leprol 74;3, pp. 217-221 (2008).
Peng, B.-Y. et al. Addressing Stem Cell Therapeutic Approaches in Pathobiology of Diabetes and Its Complications. J. Diabetes Res. 2018, 7806435 (2018).
Petranyi et al., The Effect of Single Large Dose Hydrocortisone Treatment on IgM Antibody Production, Morphological Distribution of Antibody Producing Cells and Immunological Memory, Immunology, 21:151-8 (PMID: 4934137) (1971).
Ponchel et al., "Interleukin-7 deficiency in rheumatoid arthritis: consequences for therapy-induced lymphopenia. Arthritis Res Ther, 7:R80-R92 (DOI 10.1186/ar1452) (2005).
Patt et al., Management issues with exogenous steroid therapy. Indian Journal of Endocrinology and Metabolism. 17 (Suppl 3):S612-S617. doi:10.4103/2230-8210.123548 (2013).
Ren et al., "Insulin-producing cells from embryonic stem cells rescues hyperglycemia via intra-spleen migration," Sci Rep, 4:7586 (PMID: 25533571), (2014).

(56) References Cited

OTHER PUBLICATIONS

Ritchie et al., "Persistence and Efficacy of Second Generation CART Cell Against the LeY Antigen in Acute Myeloid Leukemia", The American Society of Gene & Cell Therapy, vol. 21, No. 11, 2122-2129, Nov. 2013.
Rooman et al., "The effect of dexamethasone on body and organ growth of normal and IGF-II-transgenic mice," J Endocrinol, 163:543-52 (PMID: 10588828), (1999).
Rosenberg et al., "Durable complete responses in heavily pretreated patients with metastatic melanoma using T-cell transfer immunotherapy." Clin Cancer Res. Jul. 1, 2011 ;17(13):4550-7. doi: 10.1158/1078-0432.CCR-11-0116.
Rytel and Kilbourne, "The Influence of Cortisone on Experimental Viral Infection VIII: Suppression by Cortisone of Interferon Formation in Mice Injected with Newcastle Disease Virus," J Exp Med, 123:767-75 (1966).
Savage et al., Urinary levels of triclosan and parabens are associated with aeroallergen and food sensitization. J. Allergy Clin. Immunol. 130, 453-60.e7 (2012).
Schleimer et al., "An assessment of the effects of glucocorticoids on degranulation, chemotaxis, binding to vascular endothelium and formation of leukotriene B4 by purified human neutrophils.", J Pharmacol Exp Ther. 1989; 250(2):598-605.
Secord et al., "The Eμ-bcl-2 Transgene Enhances Antigen-Induced Germinal Center Formation in Both BALB/c and SJL Mice but Causes Age-Dependent Germinal Center Hyperplasia Only in the Lymphoma-Prone SJL Strain," Am J Pathol, 147:422-33 (PMID: 7639335), (1995).
Serafin et al., Glucocorticoid resistance is reverted by LCK inhibition in pediatric T-cell acute lymphoblastic leukemia. Blood, 130(25), 2750-2761 (2017).
Shi et al., "Infusion of haplo-identical killer immunoglobulin-like receptor ligand mismatched NK cells for relapsed myeloma in the setting of autologous stem cell transplantation", Br J Haematol. Dec. 2008; 143(5): 641-653. doi:10.1111/j.1365-2141.2008.07340.x.
Shlomchik et al., From T to B and back again: positive feedback in systemic autoimmune disease. Nat Rev Immunol; 1:147-153 (2001).
Snarski E. et al. Immunoablation and autologous hematopoietic stem cell transplantation in the treatment of new-onset type 1 diabetes mellitus: long-term observations. Bone Marrow Transplant. 51, 398-402 (2016).
Spain et al., "Effect of Cortisone on Inflammation in Mice, Minimum Dose Required to Affect Eosinophil Count, Inflammation, Wound Healing and Size of Spleen," Am J Clin Pathol, 22:944-7 (1952).
Spanier et al., The associations of triclosan and paraben exposure with allergen sensitization and wheeze in children. Allergy asthma Proc. 35, 475-481 (2014).
Sprangers et al., "Xenotransplantation: where are we in 2008?", 2008, Kidney International, vol. 74, p. 14-21.
Steinert et al., "Major biological obstacles for persistent cell-based regeneration of articular cartilage", 2007, Arthritis Research & Therapy, vol. 9, No. 3, 213 (15 pages).
Sullivan et al., Hematopoietic cell transplantation for Autoimmune disease: Updates from Europe and the United States. Biol Blood Marrow Transplant; 16(1 Suppl): S48-S56. doi:10.1016/j.bbmt.2009.10.034 (2010).
Suzuki et al., "Neutrophil infiltration as an important factor in liver ischemia and reperfusion injury. Modulating effects of FK506 and cyclosporine." Transplantation. Jun. 1993;55{6):1265-72.
Swart et al. Haematopoietic stem cell transplantation for autoimmune diseases. Nat. Rev. Rheumatol. 13, 244-256 (2017).
Thangavelu et al., Programmed death-1 is required for systemic self-tolerance in newly generated T cells during the establishment of immune homeostasis. J. Autoimmunity, 36, 301-312 (2011).
Thomas et al., Burden of Mortality Associated With Autoimmune Diseases Among Females in the United Kingdom. American Journal of Public Health. 100(11):2279-2287. doi:10.2105/AJPH.2009.180273 (2010).
U.S Department of Health and Human Services Food and Drug Administration Center for Drug Evaluation and Research (CDER) Guidance for Industry: Estimating the Maximum Safe Starting Dose in Initial Clinical Trials for Therapeutics in Adult Healthy Volunteers. Pharmacology and Toxicology Jul. 2005.
International Search Report and Written Opinion issued in International Application No. PCT/US2019/054395, dated Dec. 18, 2019, 12 pages.
Leussink et al., "High-dose methylprednisolone therapy in multiple sclerosis induces apoptosis in peripheral blood leukocytes", Archives of Neurology 58(1):91-97 (2001).
Van Winsen et al., "Suppressive effect of glucocorticoids on TNF-[alpha] production is associated with their clinical effect in multiple sclerosis", Multiple Sclerosis Journal (MSJ) 16(4):500-502 (2010).
Zhu et al., "High-Dose Dexamethasone Inhibits BAFF Expression in Patients with Immune Thrombocytopenia," J. Clin. Immun. 29(5):603-610 (2009).
Agarwal, S K and Marshall Jr, G D, "Dexamethasone promotes type 2 cytokine production primarily through inhibition of type 1 cytokines", J Interferon Cytokine Res, 21(3): 147-155 (2001).
Anderson, M S and Bluestone, J A, "The NOD mouse: a model of immune dysregulation", Annu Rev Immunol, 23: 447-485 (2005).
Annane, et al, "Corticosteroids for severe sepsis and septic shock: a systematic review and meta-analysis", BMJ, 329(7464): 480 (2004).
Arbuckle, et al, "Development of autoantibodies before the clinical onset of systemic lupus erythematosus", N Engl J Med, 349(16): 1526-1533, doi: 10.1056/NEJMoa021933 (2003).
Ashwell, et al, "Glucocorticoids in T cell development and function", Annu Rev Immunol, 18: 309-345 (2000).
Ayache, et al, "Relapses in multiple sclerosis: effects of high-dose steroids on cortical excitability", Eur J Neurol, 21(4): 630-636 (2014).
Ayala, et al, "Standard operating procedures for describing and performing metabolic tests of glucose homeostasis in mice", Dis Model Mech, 3(9-10): 525-534 (2010).
BCC Research, Global Markets for Drug Repurposing (2016). Available at: https://www.prnewswire.com/news-releases/global-markets-for-drug-repurposing-300245817.html. (Accessed: Jul. 31, 2018).
Burkitt, D, "A sarcoma involving the jaws in African children", The British Journal of Surgery, 46(197): 218-223, doi: 10.1002/bjs.18004619704 (1958).
Burkitt's Lymphoma National Treatment Guidelines, Health, IMA World (2009).
Burkitts Lymphoma Fund for Africa, Seattle, Foundation (2016).
Byrd et al, "Ibrutinib in relapsed chronic lymphocytic leukemia", N Engl J Med, 369(13): 1278-1279, doi: 10.1056/NEJMc1309710 (2013).
Communication pursuant to Rule 114(2) EPC in European Application No. 18198491.5, dated May 26, 2020, 210 pages.
Communication pursuant to Rule 114(2) EPC in European Application No. 19201254.0, dated May 26, 2020, 9 pages.
Domeier, et al., "Spontaneous Germinal Centers and Autoimmunity", Autoimmunity 50(1): 4-18 (2017).
European Extended Search Report dated Mar. 27, 2019 in European Application No. 18198491.5.
European Medicines Agency, "Benzyl alcohol and benzoic acid group used as excipients" (2017).
FDA—US: Food & Drug Administration, "Generally Recognized as Safe (GRAS)" (2018). Available at: https://www.fda.gov/food/ingredientspackaginglabeling/gras/.
Ferris, H A and Kahn, C R, "New mechanisms of glucocorticoid-induced insulin resistance: make no bones about it", J Clin Invest, 122(11): 3854-3857 (2012).
Franchimont, et al, "Effects of dexamethasone on the profile of cytokine secretion in human whole blood cell cultures", Regul Pept, 73(1): 59-65 (1998).
Freidberg, et al, "Inhibition of Syk with fostamatinib disodium has significant clinical activity in non-Hodgkin lymphoma and chronic lymphocytic leukemia", Blood, 115(13): 2578-2585, doi: 10.1182/blood-2009-08-236471 (2010).

(56) References Cited

OTHER PUBLICATIONS

Gopalakrishnapillai, et al, "Disruption of Annexin II /p11 Interaction Suppresses Leukemia Cell Binding, Homing and Engraftment, and Sensitizes the Leukemia Cells to Chemotherapy",. PLoS One, 10(10):e0140564 doi: 10.1371/journal.pone.0140564. eCollection 2015 (2015).
Han, et al, "Changes in Choroidal Thickness After Systemic Administration of High-Dose Corticosteroids: A Pilot Study", Invest Ophthalmol Vis Sci, 55(1): 440-445 (2014).
Hiepe, F, et al, "Long-lived autoreactive plasma cells drive persistent autoimmune inflammation", Nat Rev Rheumatol, 7(3): 170-178, doi: 10.1038/nrrheum.2011.1 (2011).
Hugle, T and van Laar, J M, "Stem cell transplantation for rheumatic autoimmune diseases", Arthritis Res Ther, 10(5): 217 (2008).
U.S. Appl. No. 17/281,016, filed Mar. 29, 2021.
Imperatore, et al, "Projections of type 1 and type 2 diabetes burden in the U.S. population aged <20 years through 2050: dynamic modeling of incidence, mortality, and population growth", Diabetes Care, 35(12): 2515-2520, doi: 10.2337/dc12-0669 (2012).
IPRP dated Apr. 15, 2021 issued in PCT/US2019/054395.
Kadmiel, M and Cidlowski, J A, "Glucocorticoid receptor signaling in health and disease", Trends Pharmacol Sci, 34(9): 518-530 (2013).
Knutson, et al, "Synergistic Anti-Tumor Activity of EZH2 Inhibitors and Glucocorticoid Receptor Agonists in Models of Germinal Center Non-Hodgkin Lymphomas", PLoS One, 9(12): e111840 (2014).
Liang, et al, "Donor CD8+ T cells facilitate induction of chimerism and tolerance without GVHD in autoimmune NOD mice conditioned with anti-CD3 mAb", Blood, 105(5): 2180-2188 (2005).
Maxwell et al., "Contrasting impact of corticosteroids on anti-PD-1 immunotherapy efficacy for tumor histologies located within or outside the central nervous system," Oncoimmunology, 2018, vol. 7, No. 12, e1500108, (14 pages).
Molyneux, et al, "Burkitt's lymphoma", Lancet, 31;379(9822): 1234-1244, doi: 10.1016/S0140-6736(11)61177-X (2012).
Nair, A and Jacob, S, "A simple practice guide for dose conversion between animals and human", J Basic Clin Pharm, 7(2): 27-31 (2016).
Sabbele, N R, et al, "The effect of corticosteroids upon murine B cells in vivo and in vitro as determined in the LPS-culture system", Immunology, 62: 285-290 (1987).
Sandoval-Montes, C and Santos-Argumedo, L, "CD38 is expressed selectively during the activation of a subset of mature T cells with reduced proliferation but improved potential to produce cytokines", J Leukoc Biol, 77(4): 513-521 (2005).
Sinha, A and Bagga, A, "Pulse steroid therapy", Indian J Pediatr, 75(10): 1057-1066 (2008).
Smith, L K and Cidlowski, J A, "Glucocorticoid-induced apoptosis of healthy and malignant lymphocytes", Prog Brain Res, 182: 1-30 (2010).
Snarski, E, et al, "Independence of exogenous insulin following immunoablation and stem cell reconstitution in newly diagnosed diabetes type I", Bone Marrow Transplantation, 46(4): 562-566 (2011).
Sprung, et al, "The effects of high-dose corticosteroids in patients with septic shock. A prospective, controlled study.", N Engl J Med, 311(18): 1137-1143 (1984).
Togashi, et al, "Evaluation of the appropriateness of using glucometers for measuring the blood glucose levels in mice", Sci Rep, 6(6): 25465 (2016).
Walker, N, "Accelerating Drug Development Through Repurposing, Repositioning and Rescue", Pharmaceutical Outsourcing, Available at: https://www.pharmoutsourcing.com/Featured-Articles/345076-Accelerating-Drug-Development-Through-Repurposing-Repositioning-and-Rescue/ (2017).
Wrzesinski, "Less is more: lymphodepletion followed by hematopoietic stem cell transplant augments adoptive T-cell-based anti-tumour immunotherapy" Curr Opin Immunol. Apr. 2005; 17(2): 195-201.
Wu, et al, "Double positive CD4+CD8+ T cells: key suppressive role in the production of autoantibodies in systemic lupus erythematosus", Indian J Med Res, 140(4): 513-519 (2014).
Zhang, et al, "Elimination of insulitis and augmentation of islet β cell regeneration via induction of chimerism in overtly diabetic NOD mice", PNAS, 104(7): 2337-2342 (2007).
Zhang, et al, "MHC-mismatched mixed chimerism restores peripheral tolerance of noncross-reactive autoreactive T cells in NOD mice", PNAS, 115(10): E2329-E2337 (2018).
Sabbele et al "The effect of corticosteroids upon the number and organ distribution of 'background' immunoglobulin-secreting cells in mice", Cellular Immunology, 77: 307-317 (1983).
Kunicka et al. "Immunosuppression by glucocorticoids: inhibition of production of multiple lymphkines by in vivo adminsitration of dexamethasone." Cellular immunology 149.1 (1993): 39-49.†
Sbiera et al. "Influence of short-term glucocorticoid therapy on regulatory T cells in vivo." PloS One 6.9 (2011).†
Wust et al. "Peripheral T cells are the therapeutic targets of glucocorticoids in experimental autoimmune encephalomyelitis." The Journal of Immunology 180.12 (2008): 8434-8443.†
No Author. "Dexa-ratiopharm 4 mg/8 mg Injektionslosung." Fact Information Sheet. Nov. 2018, Version 3. 12 pages (with translation).†
Theiss Suennemann et al. "Glucocorticoids attenuate acute graft-versus-host disease by suppressing the cytotoxic capacity of CD8+T cells." The Journal of Pathology 235.4 (2015): 646-655.†
No Author. "Safety Data Sheet for Dexamethasone Base USP MIC." Letco Medical and prepared by S. Smith. Revised Sep. 4, 2018. 4 pages.†
Schwartz et al. "Improved response with higher corticosteroid dose in children with acute lymphoblastic leukemia." Jornal of Clinical Oncology 19.4 (2001): 1040-1046.†
No Author. "Fortecortin Inject 100 mg." Information Sheet. Merck. No Date. 3 pages (with translation).†

\* cited by examiner
† cited by third party

IMMUNOABLATIVE THERAPIES

CROSS-REFERENCE TO RELATED APPLICATIONS

This application claims the benefit of priority of European Patent Application No. 18198491.5, filed Oct. 3, 2018, which is incorporated by reference herein in its entirety for any purpose.

FIELD OF THE INVENTION

This invention pertains to compositions for use in the treatment of diseases by immunoablation. In particular, the compositions of the invention may be for use in the treatment of diseases that are mediated by immune cells such as lymphocytes.

BACKGROUND OF THE INVENTION

The present inventors had previously found that high concentrations of glucocorticoids could be used to condition patients to enhance the efficacy of cellular immunotherapies such as adoptive T cell therapy; described in currently unpublished International patent application PCT/US2018/025517 (filed 30 Mar. 2018). In that application, the inventors had noted the toxicities associated with chemotherapy and radiation mediated preconditioning, which is believed to non-selectively destroy the cellularity of the spleen. The inventors had provided glucocorticoids (a subclass of steroids) and other non-toxic lymphodepleting agents, at acute doses, to benefit cancer patients who receive cellular immunotherapies.

International patent application PCT/US2018/025517 notes that high dose glucocorticoids can cause ablation of lymphoid tissues to reduce the binding of cellular immunotherapies to lymphoid tissue, in particular to germinal centers and marginal zones in lymph nodes and germinal centers and marginal zones in the spleen. International patent application PCT/US2018/025517 further notes that the high dose glucocorticoids also lymphodeplete peripheral blood lymphocytes via a biologic mechanism (in contrast to the cytotoxic mechanism underpinning preconditioning with chemotherapeutic agents or radiotherapy).

Prior studies into the use of steroids to precondition a patient prior to ACT had shown this approach to be ineffective. Hinrichs (J Immunother. 2005 November-December; 28(6):517-24) had evaluated dexamethasone as a preconditioning treatment prior to ACT. In comparison to total body irradiation (TBI), Hinrichs demonstrated that an HED of 0.8 mg/kg administered on day −6, day −4, and day −2 lymphodepleted equivalently to 5Gy TBI. Hinrichs demonstrate that pretreatment with systemic intraperitoneal dexamethasone at 10 mg/kg (HED 0.81 mg/kg) on day −6, −4, and −2 before ACT induced equivalent lymphodepletion compared to radiation, but this pretreatment did not enhance ACT tumor killing. In contrast, Hinrichs discloses that pretreatment with radiation did enhance ACT tumor killing. In the Hinrichs paper, the dexamethasone reportedly caused splenic lymphodepletion as demonstrated by 99% reduced spleen cellularity. However, while Hinrichs reported 99% lymphodepletion, no enhancement of ACT tumor killing was observed. In contrast, Hinrichs observed that radiation does enhance ACT tumor killing. Experiments to repeat Hinrichs reported lymphodepletion, however, demonstrate that the Hinrichs doses of intraperitoneal dexamethasone at 10 mg/kg (HED 0.81 mg/kg) on day −6, day −4, and day −2, do not effectively lymphodeplete peripheral blood lymphocytes. With Hinrichs dosing, only B lymphocytes in the peripheral blood were significantly lymphodepleted, from 10680 (vehicle control) to 3733 live events measured by flow cytometry of CD3−CD19+ cells, a 65% reduction. In contrast, CD3+T lymphocytes were reduced from 3370 to 2441 live events, only a non-significant 33% reduction. CD3+CD4+T lymphocytes were reduced from 1779 to 902 live events, only a non-significant 50% reduction. CD3+CD8_T lymphocytes were reduced from 1318 to 1277 live events, only a non-significant 3% reduction. CD3+CD4+CD25+FoxP3+Tregs were reduced from 198 to 70 live events, only a non-significant 65% reduction. And natural killer (NK) cells were reduced from 1153 to 958 live events, only a non-significant 17% reduction.

Autoimmunity is the phenomena of the immune system aberrantly mounting an attack on a subject's own constituents. (In healthy subjects, the immune system avoids damaging autoimmune reactions by establishing tolerance to the subject's own constituents.) Diseases that result from damaging autoimmune reactions are termed autoimmune diseases. Different autoimmune diseases affect different parts of the body; these can be debilitating (e.g. in the case of rheumatoid arthritis, which affects the joints) neurodegenerative/neurodestructive (e.g. in the case of multiple sclerosis) and are in some cases, such as diabetes mellitus, associated with substantial mortality rates (Thomas et al., 2010).

The pathogenesis of autoimmune disorders is widely attributed to a crucial role to T and B lymphocytes inappropriately recognizing self antigens and initiating a cell-mediated or humoral reaction, or both, resulting in inflammatory tissue and vascular damage (Sullivan et al, 2010; Shlomchik et al., 2001).

Autoimmune diseases are very often treated by prolonged administration of immunosuppressives such as steroids. For instance, pemphigus patients have been treated with 100 mgs dexamethasone by 2 hour IV infusion daily for 3 days (Pasricha et al., 2008). This dose is not lymphoablating. The pemphigus patients were treated in this way every 28 days until cure. It took between 3 and 12 months to cure them. The relapse rate was 15% and all patients went in to remission with another Dexa treatment. This dose of Dexa is between about 1-2 mg/kg. While helping to manage the autoimmune disease and reducing symptoms, such treatment regimens are not curative, involve several long term side effects and the increased risk of infection (Patt et al., 2013).

Lymphodepletion therapies are increasingly tested for controlling immune damage. One appealing premise for such a therapy is that it may 'reboot' the immune system and restore immune tolerance (Lu et al., 2011). However, the tolerogenic potential of lymphodepletion therapies remains controversial. The debate is exemplified by conflicting evidence from the studies of anti-thymocyte globulin (ATG), a prototype of immunodepleting drugs, in particular on whether it induces CD4+CD25+Foxp3+ regulatory T (Treg) cells (Lu et al., 2011). To understand the impact of ATG on T cells at a clonal level in vivo, Lu et al studied the effect of anti-mouse thymocyte globulin (mATG) in a reductionist model in which the T-lymphocyte repertoire consists of a single clone of pathogenic T effector (Teff) cells specific to a physiological self-antigen. The mATG treatment led to peripheral induction of antigen-specific Treg cells from an otherwise monoclonal Teff repertoire, independent of thymic involvement. The de novo induction of Treg cells occurred consistently in local draining lymph nodes, and persistence of induced Treg cells in blood correlated with long-term protection from autoimmune destruction. (Lu et al., 2011) thus provides in vivo evidence for clonal conversion from a pathogenic self-antigen-specific Teff cell to a Treg cell in the setting of immunodepletion therapies.

Type 1 diabetes mellitus (T1D) is an autoimmune disease that progressively results in the depletion of insulin-secreting β-cells that eventually culminates in clinically significant hyperglycemia and metabolic instability (Atkinson et al., 2014). Overall, T1D accounts for approximately 5% of diabetes and affects about 20 million individuals worldwide (Menke et al., 2013). About 1.25 million Americans have T1D and an estimated 40,000 people will be newly diagnosed each year in the U.S (American Diabetes Association, *Diabetes Care* 37, 2014). TD1 is associated with an annual economic burden in U.S. of $14.4 billion, considering medical expenses and indirect costs such as lost income.

Therapeutic insulin and other treatment based on external hypoglycemic agents do not cure T1D, but simply offer solutions to control glucose level in blood. Patients remain susceptible to labile blood glucose levels and the development of microvascular and macrovascular diabetic complications (Peng et al., 2018).

Safe interventions to remove autoimmune substrates from diabetes patients are missing. Autoimmunity in TD1 includes many arms of the immune response (Snarski et al 2016; Cantu-Rodriguez et al., 2016). As a consequence, antigen-specific immunotherapies based on the use of antibodies, fusion proteins, cytokines, regulatory T cells, and small-molecule inhibitors lead only to some degrees of β-cells preservation and reduction of blood glucose level in patients with T1D (Kim et al., 2013). Even in combinations, immunotherapies targeting specific components of autoimmunity repertoire failed to guarantee restoration of insulin independence (Bone et al., 2017).

*Autologous hematopoietic stem cell transplantation (HSCT)* is so far the only proven strategy for T1D cure (Voltarelli et al., 2007). Autologous HSCT has been performed for twelve years as a therapeutic option for autoimmune diseases (ADs) such as multiple sclerosis, systemic sclerosis, rheumatoid arthritis, systemic lupus erythematous, Crohn's disease and others (Swart et al., 2017). This more intense and wider immunologic approach consists in an "immunologic reset" performed with high-dose immunosuppression which comprises non-specific abrogation of autoreactive T- and B-cell responses followed by hematopoietic stem cell transplantation for reconstitution of a tolerant immune system. Remarkably, in clinical trials, this approach has enabled up to 80% of T1D patients to experience periods of insulin independence in parallel with relevant increments in C-peptide levels during mixed meal tolerance test (Couri et al., 2018). However, serious concerns are preventing the adoption of immunologic reset as a therapeutic approach for T1D.

Risks associated with the HSCT procedure exceed the positive effects offered for T1D: HSCT is still associated with significant toxicities and up to 3% mortality (Alexander et al., 2018; Pallera et al., 2004; Henig et al., 2014). Moreover, current protocols for immunologic reset are based on cytotoxic immunosuppressive regimens (e.g. chemotherapy, radiotherapy) that expose patients to a series of safety issues including short-term risks of infection, acute organ dysfunction and death, and long-term risks of malignancies and secondary autoimmune diseases (Daikeler et al., 2012).

Almost all T1D patients treated with HSCT resumed exogenous insulin use, with a subsequent decrease in C peptide levels (Magdalena et al., 2018) as the effect of incomplete ablation of autoimmune pathophysiologic substrates after preconditioning (PC) (Loh et al., 2007). Increasing the intensity of transplant conditioning regimens or repeating the procedure to improve treatment outcomes would expose patients to excessive risks and toxicities (Couri et al., 2018).

HSCT is associated with high costs, which range from approximately $80,000 to $300,000, depending on conditioning regimens given before HSCT, transplant type, and inpatient costs associated with hospitalization (Broder et al., 2017).

A need exists for further treatments of autoimmune disorders and other diseases that are mediated by lymphocytes. Further treatments that are simpler and less costly than HSCT would be desired.

SUMMARY OF THE INVENTION

The present invention is based on the surprising finding that high doses of glucocorticoids can act to cause lymphodepletion of peripheral blood lymphocytes without substantially affecting the cell count of other cells. Further actions such as the ablation of germinal centers also underpins certain aspects of this invention. The present invention provides medical applications of these actions of high dose glucocorticoid agonists; for use in the treatment of lymphocyte mediated diseases.

Accordingly, in a first aspect, the invention provides a pharmaceutical composition comprising a glucocorticoid, for use in the treatment of a lymphocyte mediated disease in a subject, wherein the treatment comprises administering a dose of the pharmaceutical composition to the patient to deliver the glucocorticoid at a dose equivalent to about 15 to about 26 mg/kg human equivalent dose (HED) of dexamethasone base. The dose of glucocorticoid may be termed an 'acute high dose'. The pharmaceutical composition may (or may not) comprise a pharmaceutically acceptable carrier as defined herein. The pharmaceutical composition may (or may not) comprise a pharmaceutically acceptable preservative as defined herein. The pharmaceutical composition may (or may not) comprise a pharmaceutically acceptable chelating agent as defined herein. However, in all embodiments of this aspect, the pharmaceutical composition does comprise one or more ingredients selected from the group consisting of: a pharmaceutically acceptable carrier, a preservative, and/or a chelating agent. The pharmaceutical composition may also include excipients, in some embodiments. In some embodiments, the pharmaceutical composition comprises more than one pharmaceutically acceptable carriers. In some embodiments, the pharmaceutical composition comprises more than one pharmaceutically acceptable preservatives. In some embodiments, the pharmaceutical composition comprises more than one pharmaceutically acceptable chelating agents. Embodiments of this invention can be defined as acting to achieve systemic lymphodepletion in the subject. Lymphodepletion involves the removal of B and T cells.

In some embodiments, the lymphocyte mediated disease is an autoimmune disease, for instance an autoimmune disease selected from the group consisting of Type 1 diabetes, multiple sclerosis, amyotrophic lateral sclerosis, scleroderma, pemphigus and lupus. The lymphodepletive action of the invention underpins the efficacy of these embodiments.

Despite glucocorticoids having a well-established use in many autoimmune conditions (Flammer et al., 2011) they have never been considered for immunologic reset. In addition, studies based on the use of pharmaceutical low doses to precondition patients prior to autologous cell transplant showed this approach to be ineffective (Medicines Agency; 2017). The complex mode of action based on multiple in vivo effects of the pharmaceutical composition of the present invention provides the first effective replacement of chemotherapy that can be used as safe immunologic reset regimen for treatment of autoimmune conditions such as diabetes mellitus.

Several advantages are associated with the present invention, relating to the actions of the pharmaceutical composition, including (i) Non-myeloablative immunologic reset: The pharmaceutical composition can deplete all peripheral blood lymphocyte types, for example, including islet-specific autoreactive T-cells responsible for diabetes autoimmunity, but spare neutrophils, platelets, RBCs and stem cells (both HSCs and MSCs) based on the specific receptor-mediated mode of action. The invention therefore reduces risks of infection and removes the need of HSCT to recover blood cells after immune-reset. The result is a non-myeloablative regimen that can perform a safe immunologic reset with efficacy comparable to chemotherapy. (ii) Reduction of germinal centers (GCs) and marginal zones in secondary lymphatics. The pharmaceutical composition transiently ablates germinal centers in the secondary lymphoid organs that give rise to high-affinity antibodies and long-lived plasma cells (DeFranco et al., 2016) for increased efficacy over autoimmune pathophysiologic substrates. (iii) Simple modes of administration. The pharmaceutical composition can be formulated for oral or intravenous administration routes, making it effective within hours with lymphocyte and GC recovery within 7-14 days. For the first time, complete lymphodepletion will not require hospitalization. (iv) Reduced chances of relapse. Unlike chemotherapy or radiation, the pharmaceutical composition of the invention can be safely administered at completely lymphoablating doses to remove memory T and B cell responsible of relapse. (v) Acceptable re-administration. In case of relapse of autoimmune pathophysiologic substrates, the safety profile of high dose glucocorticoids will allow repetitive dosing of the pharmaceutical compositions of the invention.

These actions and advantages associated with the present invention, disclosed herein, mean that the skilled person will understand that the invention provides an effective strategy for treating autoimmune diseases as well as the other lymphocyte mediated diseases discussed herein.

In some embodiments, the lymphocyte mediated disease is residual HIV disease. In these embodiments, as described herein, a reduced number of germinal centers in the subject's lymphoid organs can force residual HIV infected T cells, which bind to niches in these centers, into the circulation where they can be eliminated by the immune system or standard therapies. Within the context of this disclosure, the skilled person will understand that HIV is a lymphocyte mediated disease in the sense that the virus infects T lymphocytes. The lymphodepletive action of the invention also contributes to the efficacy of these embodiments.

In other embodiments, the lymphocyte mediated disease is a lymphoma, e.g. a germinal centre lymphoma (GC lymphoma) or marginal zone lymphoma. In these embodiments, as described herein, a reduced number of germinal centers in the subject's lymphoid organs can force cancer cells (for example germinal center lymphomas), which bind to niches in these centers, into the circulation where they can be eliminated by the immune system or standard therapies. The lymphodepletive action of the invention also contributes to the efficacy of these embodiments. In particular embodiments, treatment of Burkitt's Lymphoma (BL) is specifically envisaged. In Africa, BL treatment revolves around a combination of three chemotherapy drugs, Cyclophosphamide, Vincristine, and Methotrexate (systemic and intrathecal). This combination is repeated at 2-week intervals for a total of six cycles over 12 weeks (*Burkitt's Lymphoma National Treatment Guidelines*. 2009). Lower doses of dexamethasone are currently on the WHO List of Essential Medicines, however, the existing WHO listed dexamethasone products are not suitable for BL treatment, as the higher dose of the present invention would require compounding vials that could lead to contamination and serious or fatal infections in patients as well as to excipients such as benzyl alcohol or parabens that reach toxic levels with compounding.

In yet further embodiments, the lymphocyte mediated disease is graft versus host disease (GvHD). GvHD is a medical complication following the receipt of transplanted tissue from a genetically different person. GvHD can occur even with autologous transplant, most likely caused by the processing and storage of the autologous cells such that the transplanted cells then recognize the body as foreign. In GvHD, the white blood cells of the donor's immune system which remain within the donated tissue (the graft) recognize the recipient (the host) as foreign (non-self). The white blood cells present within the transplanted tissue then attack the recipient's body's cells, which leads to this condition. GvHD is commonly associated with stem cell transplants such as those that occur with bone marrow transplants. GvHD also applies to other forms of transplanted tissues such as solid organ transplants. The lymphodepletive action of the invention also contributes to the efficacy of these embodiments.

In other embodiments, the lymphocyte mediated disease is an allergic disorder. This includes chronic and acute allergies. For instance, the pharmaceutical composition of the invention could be used in the treatment of asthma. The lymphodepletive action of the invention also contributes to the efficacy of these embodiments.

In some embodiments, the pharmaceutical composition comprises a pharmaceutically acceptable carrier. In some embodiments, the pharmaceutical composition comprises a preservative and/or a chelating agent. In some embodiments, the pharmaceutical composition comprises a preservative. Preferably, the preservative is a sulfite. In some embodiments, the pharmaceutical composition comprises a chelating agent, which may be EDTA.

In preferred embodiments, the glucocorticoid of the pharmaceutical composition comprises dexamethasone. This may be in the form of dexamethasone base, dexamethasone sodium phosphate or dexamethasone acetate. Most preferably, the glucocorticoid is dexamethasone sodium phosphate.

As noted above, and as defined by the claims, the pharmaceutical composition of the invention is for use in the treatment of a lymphocyte mediated disease. The treatment may comprise administering the dose of the pharmaceutical composition as a single acute dose.

Alternatively, the treatment comprises administering the dose of the pharmaceutical composition as a total dose given over about a 72 hour period.

The treatment of lymphocyte mediated diseases include administration of the compositions to patients in need of anti-inflammatory, immunosuppressive, lymphoablation, germinal center elimination, IL-2 IL-7 IL-12 and/or IL-15 elevation, mesenchymal stem cell elevation, G-CSF increase, or neutrophil increase. Moreover, the treatment of lymphocyte mediated disease may result in detectable changes in PD-1 or PD-L1 or CTLA-4 expression.

As noted above, and as defined by the claims, the pharmaceutical composition of the invention is for use in the treatment of a lymphocyte mediated disease, wherein the treatment comprises administering a dose of the pharmaceutical composition to the patient. The pharmaceutical composition may be administered intravenously (IV) or orally. When intravenous administration is performed, preferably, the dose is administered as a single IV infusion over 0.25-2 hours. The infused composition may be in normal or half-normal saline or Lactated Ringer's or 5% Dextrose or another standard IV fluid solution. For oral administration, the composition may be given as a single oral dose mixed with a small amount of juice or sweetener.

In preferred embodiments, the pharmaceutical composition is provided as an aqueous glucocorticoid solution. The skilled person will appreciate that this means that water is used as a solvent in the pharmaceutical compositions of these embodiments.

The pharmaceutical composition for the use according to the invention is administered to deliver the glucocorticoid at a dose equivalent to at least about 15 mg/kg, or at least about 16 mg/kg, or at least about 17 mg/kg, or at least about 18 mg/kg, or at least about 19 mg/kg, or at least about 20 mg/kg, or at least about 21 mg/kg, or at least about 22 mg/kg, or at least about 23 mg/kg, or at least about 24 mg/kg, or at least about 25 mg/kg, or at least about 26 mg/kg of a human equivalent dose (HED) of dexamethasone base. The dose of the pharmaceutical composition can be defined as delivering the glucocorticoid at a dose equivalent to a value taken from a range of doses equivalent to HED of dexamethasone base, where the range is defined by endpoints selected from the above list of values, e.g. about 15 mg/kg-26 mg/kg, or about 18 mg/kg-25 mg/kg (or any two values from the above list). In preferred embodiments, the subject is human, the glucocorticoid contains dexamethasone base, and the pharmaceutical composition is administered to the human subject at a dose of between about 15.0 and about 21.0 mg/kg of dexamethasone base.

The skilled person will understand that conventional methodology can be employed to measure the lymphodepletion achieved by the invention. For instance, CD4+, CD8+, Tregs and/or B cells populations can be measured after the pharmaceutical composition has been administered, for instance 48 hours after its administration. Flow cytometry is one exemplary method that may be used to perform the cell counts.

The skilled person will understand that this invention can be used in conjunction with other therapeutic approaches as described herein, for instance chemotherapy and/or cell based therapies. In these embodiments, the subject may be administered chemotherapy. In these embodiments, the subject may be administered a cell based therapy. However, most embodiments of the invention do not involve chemotherapy or cell based therapies. Thus, in some embodiments, the subject is not administered chemotherapy. In some embodiments, the subject is not administered cell based therapies.

The mechanism of action of the invention is discussed in detail herein and these mechanisms can form part of the distinctive features of the invention in some instances, particularly where the mechanism opens up a new clinical situation (e.g. by allowing patient subgroups to be selected as the subjects).

SUMMARY OF THE FIGURES

Embodiments and experiments illustrating the principles of the invention will now be discussed with reference to the accompanying figures in which:

FIG. 14, FIG. 15, FIG. 16 and FIG. 17 show data from the same four human patients.

DETAILED DESCRIPTION

Figure 1:
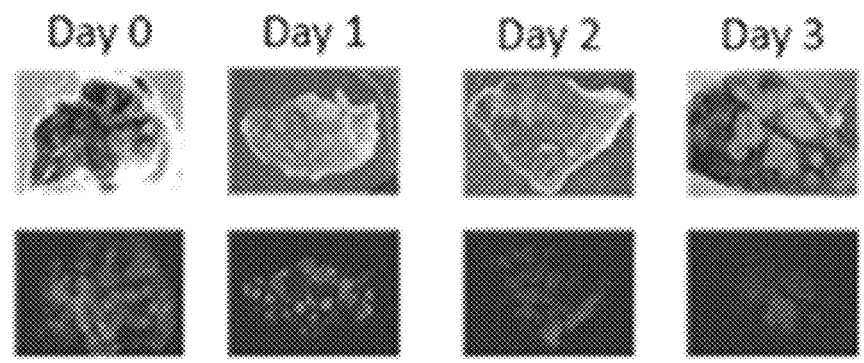
FIG. 1. Acute high dose dexamethasone eliminates binding niches in the mouse spleen and secondary lymphatics. Shown are black and white scale bright field (top) and immunofluorescent (bottom) images of fresh thick spleen sections stained with FITC-PNA to quantitate germinal centers from mice administered IP human equivalent dose (HED) 9.3 mg kg dexamethasone base 96 hours before spleen harvest. The graph shows column plots of average germinal cell count per spleen area plus standard area of the mean (SEM) for mice administered IP placebo control and IP HED 9.3 mg kg dexamethasone base 96 hours before spleen harvest. Control mice have significant FITC-PNA immunofluorescence, while mice who were injected with dexamethasone have almost no immunofluorescent signal.
Figure 1:
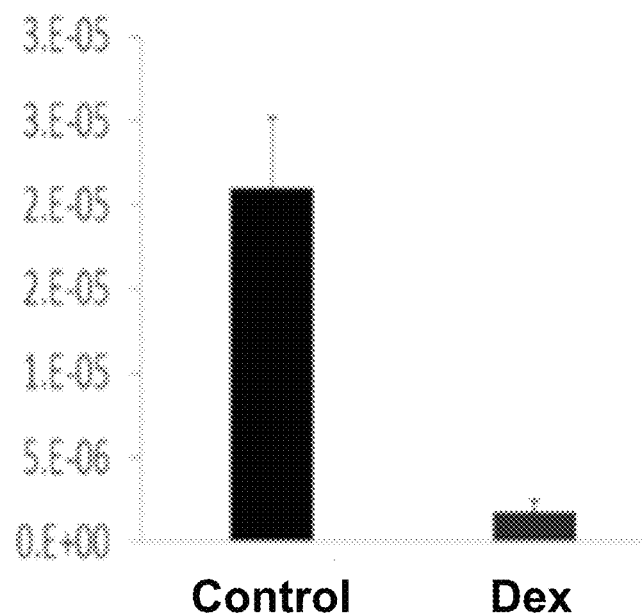

Cytotoxic chemotherapeutic agents trigger cell death via mechanisms or means that are not receptor mediated. Cytotoxic chemotherapeutic agents trigger cell death by interfering with functions that are necessary for cell division, metabolism, or cell survival. Because of this mechanism of action, cells that are growing rapidly (which means proliferating or dividing) or are active metabolically will be killed preferentially over cells that are not. The status of the different cells in the body as dividing or as using energy (which is metabolic activity to support function of the cell) determines the dose of the chemotherapeutic agent that triggers cell death. The skilled person will appreciate that the glucocorticoid that is utilized in this invention is not a cytotoxic chemotherapeutic. Cytotoxic chemotherapeutic agents non-exclusively relates to alkylating agents, antimetabolites, plant alkaloids, topoisomerase inhibitors, antineoplastics and arsenic trioxide, carmustine, fludarabine, IDA ara-C, myalotang, GO, mustargen, cyclophosphamide, gemcitabine, bendamustine, total body irradiation, cytarabine, etoposide, melphalan, pentostatin and radiation.

The present invention pertains to pharmaceutical compositions comprising a glucocorticoid for use in the treatment of diseases by immunoablation. In particular, the compositions of the invention may be for use in the treatment of diseases that are mediated by immune cells such as lymphocytes. The treatment comprises administering a dose of the pharmaceutical composition to the patient to deliver the glucocorticoid at a dose equivalent to about 15 to about 26 mg/kg human equivalent dose (HED) of dexamethasone base.

As used herein, the term glucocorticoid includes glucocorticoid receptor agonists and any compound that binds to the glucocorticoid receptor. Such compounds relate to, but are not limited to, dexamethasone, dexamethasone containing agents, hydrocortisone, methyl predisone, prednisone, corticone, budesonide, betamethasone and beclomethasone. Other glucocorticoids include prednisolone, mometasone furoate, Triamcinolone Acetonide and methylprednisolone. Glucocorticoids further include glucocorticoid receptor modulating agonists. Additionally, selective glucocorticoid receptor agonists may be used in the pharmaceutical compositions disclosed herein. Such agonists or modulators include for example, selective glucocorticoid receptor modulators (SEGRMs) and selective glucocorticoid receptor agonists (SEGRAs). Glucocorticoids, glucocorticoid receptor modulators and selective glucocorticoid receptor agonists (SEGRAs) that may be utilized in the herein disclosed methods and compositions are well know to those skilled in the art.

Glucocorticoids and glucocorticoid-receptor (GR) modulating agents exert their effects through both membrane glucocorticoid receptors and cytoplasmic GRs which activate or repress gene expression. Some of the desirable lymphodepletion effects of the glucocorticoids and GR modulating agents appear to be mediated via membrane GRs or other non-genomic effects in addition to their genomic effects. Interestingly, co-treatment with dexamethasone has been shown to be able to reduce glucocorticoid resistance (Serafin et al., 2017).

The effects of glucocorticoids are complex and depend on each specific glucocorticoid's affinity for the GR and mineralocorticoid receptor (MR). Additionally, there are now 9 known isoforms of the cytosolic GR and additional membrane expressed GR receptors that have been identified but which are not fully characterized. Glucocorticoids have been reported to have varied effects on lymphocyte levels, depending on the concentration of the glucocorticoid administered and the duration of treatment. In general, at low doses typically used for chronic therapy, glucocorticoids have been reported to redistribute lymphocytes from the peripheral blood into the bone marrow, at medium doses glucocorticoids have been reported to cause leukocytosis thought to be a redistribution of leukocytes from the bone marrow, spleen and thymus into the peripheral blood, and at high doses glucocorticoids have a lymphotoxic action on lymphocytes by triggering apoptosis and necroptosis. The duration of effect also depends on the dose level, for instance Fauci et al (1976) reports a single oral 0.24 mg/kg dexamethasone dose suppresses peripheral blood T and B lymphocytes 80% with recovery beginning at 12 hours and normal levels by 24 hours. However, the present invention demonstrates that acute oral doses of 3 mg/kg or greater are necessary to reduce peripheral blood T and B cells 24-48 hours after administration, with return to baseline levels occurring around 5 to 14 days after dosing.

Figure 14:
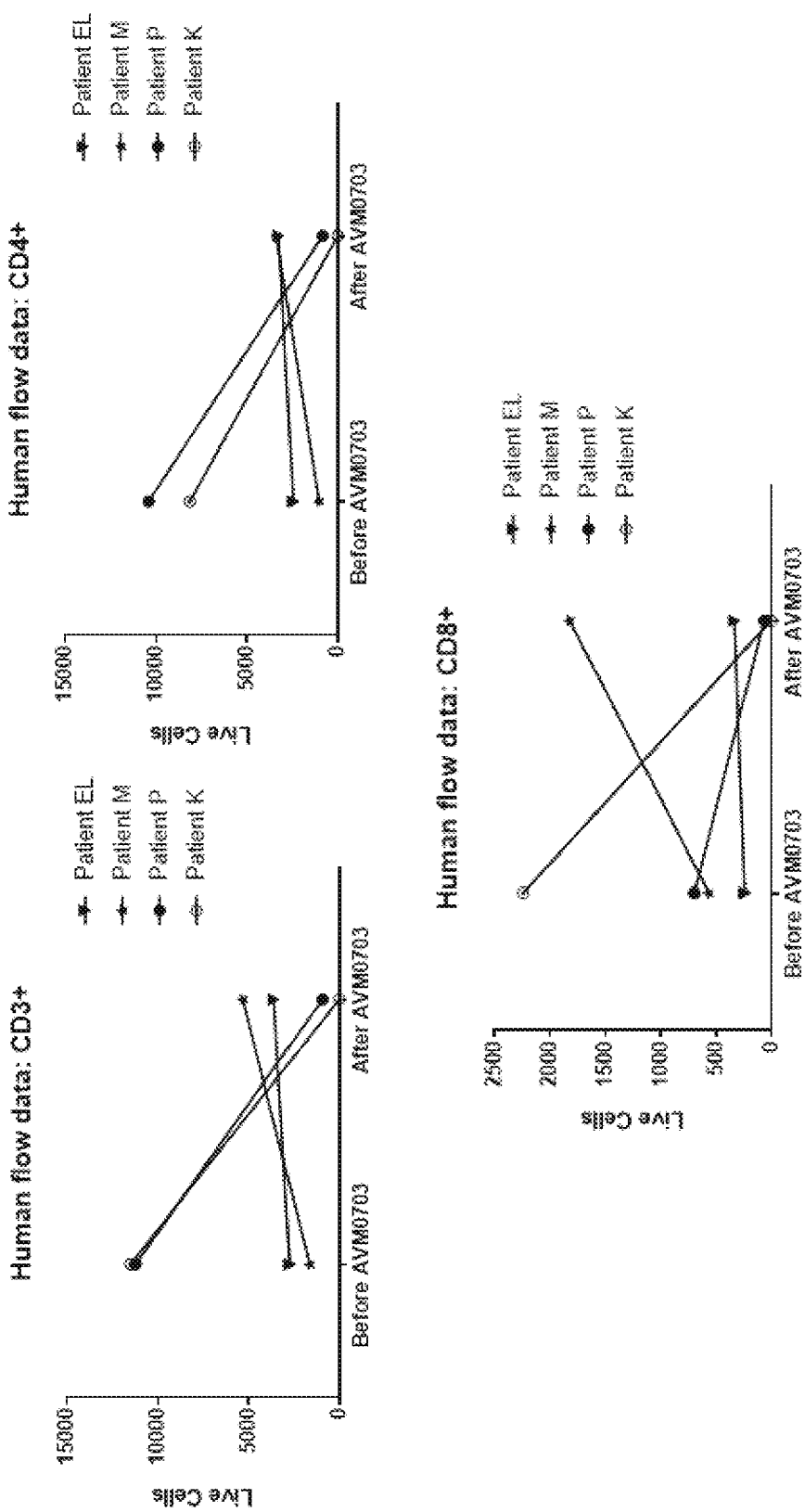
FIG. 14. Fifty percent (2 of 4) of human patients treated with 3 mg/kg dexamethasone base depleted CD3, CD4 and CD8 positive lymphocytes. Individual pre- and post-treatment, 48 hours after oral administration of 3 mg/kg dexamethasone base to four human patients, values and line plots of CD3+, CD4+, and CD8+ lymphocytes measured by flow cytometry are shown. Each patient's pre-treatment values are connected to post-treatment values by a connecting line. CD4+ cells are also CD3+. CD8+ cells are also CD3+.
Figure 17:
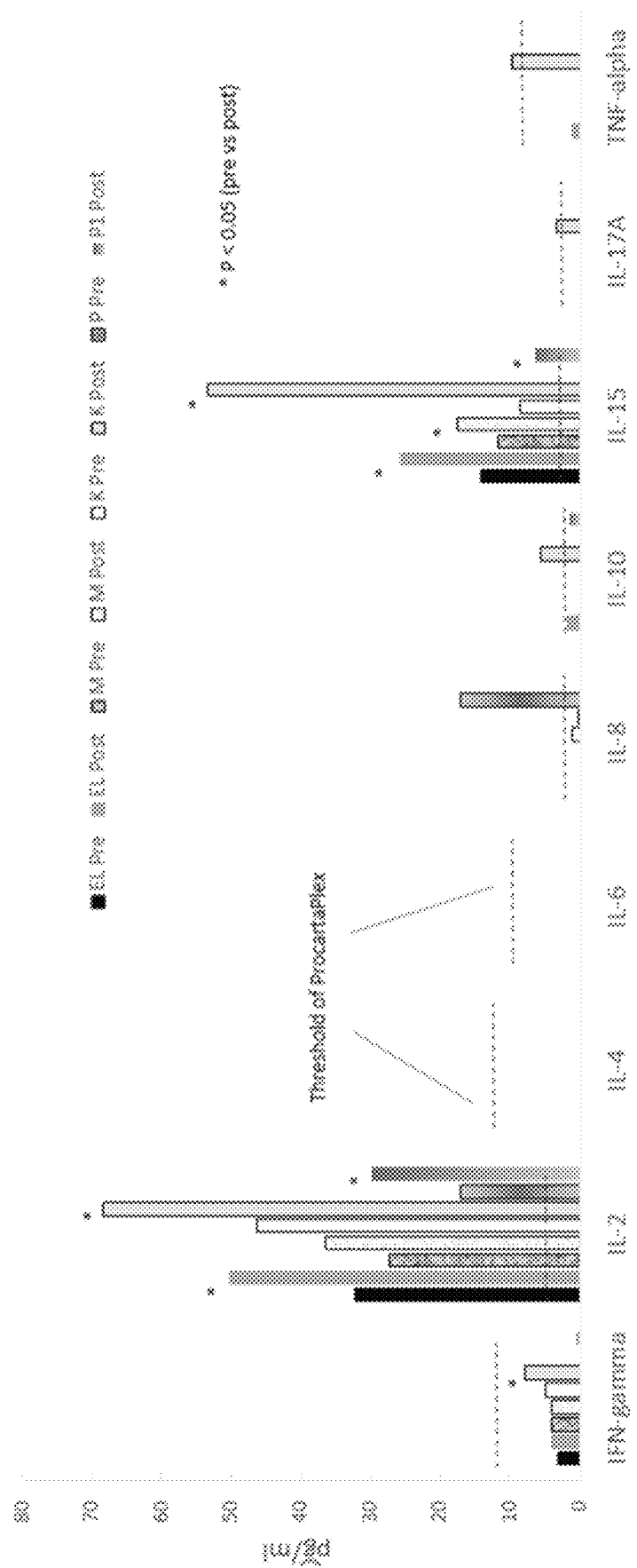
FIG. 17. 100% of human patients treated with 3 mg/kg dexamethasone base showed increased serum IL-2 and/or IL-15 levels, but no elevation in IL-6. Column plots of each patients pre- and post-treatment, 48 hours after oral administration of 3 mg/kg dexamethasone base to four human patients, plasma levels of interleukin 2 and interleukin 15 measured by ProCartaPlex-9 plx Luminex assay.

The desired in vivo effects of exemplary glucocorticoids would include reductions in germinal center and marginal zones in secondary lymphatics, direct tumor killing of some cancers particularly; multiple myeloma, renal cell carcinoma, leukemia and lymphoma, non-small cell lung cancer (NSCLC), prostate and breast cancer; depletion of all peripheral blood lymphocyte types, lack of lymphocyte redistribution to the BM or other organs, and elevation of plasma cytokines including IL-2, and/or IL-7, and/or IL-12, and/or IL-15 to levels preferably of 20 pg/ml or greater, among others. Exemplary glucocorticoids do not elevate plasma levels of IL-6, one of the major contributors to ACT induced cytokine release syndrome (CRS). Exemplary glucocorticoids do not elevate plasma levels of GM-CSF, one of the major contributors to ACT induced neuroedema. Acute doses of dexamethasone of about HED 6 mg/kg and above reduce germinal centers and marginal zones in secondary lymphatics; acute doses of dexamethasone of about 1.6 mg/kg HED in a 48 hour period have about 50% direct tumor killing against multiple myeloma and other cancer cell lines which is maintained but not increased with doses up to about 12 mg/kg HED; acute doses of dexamethasone of greater than about HED 3 mg/kg are required for lymphodepletion demonstrated by the observation that 50% of patients treated with 3 mg/kg HED showed lymphocytosis (FIG. 14); plasma IL-2 and IL-15 cytokine elevations are observed at doses of dexamethasone base of about HED 3 mg/kg or higher (FIG. 17). Based on the desired in vivo effects in the indications disclosed in this application, the most preferred acute dexamethasone base doses, which can be converted to equivalent doses of other glucocorticoids based on known calculators or as disclosed in this description, will be most likely about HED 9 mg/kg and above.

A single high dose of glucocorticoid can be given as an oral administration or about a one hour IV infusion. A total dose may be given as repetitive IV or oral doses in any quantity such that the total dose, e.g. of dexamethasone, is about 15 mg/kg to about 26 mg/kg within about a 24 to about a 72 hour period.

Equivalent doses of another glucocorticoid or glucocorticoid receptor modulating agent can be readily and easily calculated using publicly available corticoid conversion algorithms, preferably http://www.medcalc.com. For instance, 3 to 12 mg/kg dexamethasone converts to 19 to 75 mg/kg prednisone. Since prednisone's biologic half-life is about 20 hours, while dexamethasone's biologic half-life is about 36 to 54 hours. Therefore, prednisone would be dosed between 19 to 75 mg/kg every 24 hours for equivalent biologic dosing. More specifically, a 12 mg/kg dose of dexamethasone corresponds to 1) a 75 mg/kg dose of prednisolone that would require repeat dosing of about two to about three doses every 24 hours. A 10 mg/kg dose of betamethasone is about 12 mg/kg dexamethasone and has a pharmacodynamic (biologic) half-life similar to dexamethasone. However, betamethasone reduces RBC at doses of about 24 mg/50 kg (Gaur 2017).

DEX (dexamethasone base) doses in the examples in the present application are given as human equivalent doses (HED). AVM0703 (also referred to as AugmenStem™ or PlenaStem™) in the examples given is Dex (dexamethasone base) as dexamethasone sodium phosphate in a proprietary buffer.

Methods for calculating the human equivalent dose (HED) are known in the art. For example the FDA's Centre for Drug Evaluation and Research (CDER) issued a highly-cited guidance document in 2005 (U.S Department of Health CDER, 2005), which sets out the established algorithm for converting animal doses to HED based on body surface area (the generally accepted method for extrapolating doses between species) at Table 1 on page 7 of that document. For reference, Table 1 is reproduced below. The skilled person understands that the animal dose in mg/kg, explained below, the HED is calculated easily using the standard conversion factors in the right hand columns of Table 1:

TABLE 1

Conversion of Animal Doses to Human Equivalent Doses Based on Body Surface Area

| Species | To Convert Animal Dose in mg/kg to Dose in mg/m², Multiply by $k_m$ | To Convert Animal Dose in mg/kg to HED[a] in mg/kg, Either: | |
|---|---|---|---|
| | | Divide Animal Dose By | Multiply Animal Dose By |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a] Assumes 60 kg human. For species not listed or for weights outside the standard ranges, HED can be calculated from the following formula: HED = animal dose in mg/kg × (animal weight in kg/human weight in kg)$^{0.33}$.
[b] This $k_m$ value is provided for reference only since healthy children will rarely be volunteers for phase 1 trials.
[c] For example, cynomolgus, rhesus, and stumptail.

Doses described herein can be presented as a "weight based dose" or as a "body surface area (BSA) based dose." A weight based dose is a dose that is administered to a patient that is calculated based on the weight of the patient, e.g., mg/kg. A BSA based dose is a dose that is administered to a patient that is calculated based on the surface area of the patient, e.g., mg/m2. The two forms of dose measurement can be converted within the context of human dosing by multiplying the weight based dose by 37 or dividing the BSA based dose by 37 as shown in Table 1 above.

The terms "subject" and "patient" are used interchangeably herein, and refer to a human or animal.

Dexamethasone, like the other glucocorticoid steroids at equivalent doses, inhibits the formation and proliferation of germinal centers in the lymph tissues and lymphodepletes peripheral blood. The doses of glucocorticoid, particularly dexamethasone, preferably achieve greater than 75% lymphodepletion. More preferably, the doses of glucocorticoid, particularly dexamethasone, achieve greater than 80% lymphodepletion. Most preferably, the dose of glucocorticoid, particularly dexamethasone, achieves greater than 95% lymphodepletion. The skilled person will understand that lymphodepletion can be measured readily by measuring complete blood counts (CBCs).

Dexamethasone and other preferred glucocorticoids spare neutrophils and do not inhibit neutrophil function (Schleimer R P, J Pharmacol Exp Ther 1989; 250:598-605), and spare red blood cells (RBCs), platelets, mesenchymal stem cells (MSC) and hematopoietic stem cells (HSC). Neutrophil sparing in humans is an absolute neutrophil count (ANC) greater than 500 per $mm^3$. By sparing neutrophils, RBCs and platelets, lymphoablating glucocorticoids would reduce or eliminate the need for transfusions. Lymphoablating glucocorticoids also spare bone marrow mesenchymal stem cells (MSCs) and do not affect the capacity of bone marrow MSCs to differentiate towards chondrocytes, osteocytes or adipocytes. Lymphoablating glucocorticoids also increase the endogenous number of BM MSCs or their ex vivo survival in both humans and horses. Lymphoablating glucocorticoids increase plasma IL-2, IL-7, IL-12 and IL-15 levels, but not IL-6 or GM-CSF levels. In some embodiments of the invention, the subject is selected before treatment and/or assessed after treatment, based on measurements of the plasma levels of one or more of these cytokines.

Dexamethasone is approved for use with an initial dosage of dexamethasone sodium phosphate injection that varies from 0.5 to 9 mg a day depending on the disease being treated, which is a daily dose of 0.01 to 0.18 mg/kg based on a 50 kg BW. In less severe diseases doses lower than 0.5 mg may suffice, while in severe diseases doses higher than 9 mg may be required. There is a tendency in current medical practice to use high (pharmacologic) doses of corticosteroids for the treatment of unresponsive shock. For cerebral edema Dexamethasone sodium phosphate injection is generally administered initially in a dosage of 10 mg intravenously followed by four mg every six hours intramuscularly until the symptoms of cerebral edema subside. This total dose would correspond to a total 24 hour dose of about 0.34 to 0.48 mg/kg and a total 72 hour dose of 0.8 to 1.12 mg/kg in 72 hours, which is not an effective dose according to the present invention, which uses doses between about 15 mg/kg and about 26 mg/kg.

For acute allergic disorders, dexamethasone sodium phosphate injection, USP 4 mg/mL; is recommended: first day, 1 or 2 mL (4 or 8 mg), intramuscularly, then Dexamethasone sodium phosphate tablets, 0.75 mg; second and third days, 4 tablets in two divided doses each day; fourth day, 2 tablets in two divided doses; fifth and sixth days, 1 tablet each day; seventh day, no treatment; eighth day, follow-up visit. Dexamethasone has been used in the emergency room for severe acute pediatric asthma at 2 mg/kg, a dose which is below the glucocorticoid doses as defined in this invention. Dexamethasone has also been used at 6 mg/kg to treat pediatric acute lymphoblastic leukemia, a dose which is below the glucocorticoid doses as defined in this invention.

Conventional formulations of glucocorticoids such as dexamethasone may be unsuitable for use in the therapeutic applications of the present invention. For instance, dexamethasone sodium phosphate (DSP) is currently available in low dose (2-4 mg/ml) and low volume formulations (e.g. APP Pharmaceuticals, Mylan), which contain antimicrobial preservatives such as benzyl alcohol (BA) and propyl paraben (PP). The target dose of DSP required for performing complete lymphoablation would entail the use of multiple vials resulting in overdoses of excipients. Exceeding WHO acceptable daily intake (ADI) of both benzyl alcohol and propyl paraben has been associated with genotoxicity and increased risk of cancer (Darbre et al., 2014), reproductive toxicity (Aker et al., 2016), increased risks of allergic disease (Savage et al., 2012; Spanier et al., 2014), and neonatal CNS dysfunctions (Medicines Agency, 2017). Moreover, with commercially available DSP package inserts, serious neuropsychiatric effects occur in about 6% of patients who receive steroids (Malmegrim et al., 2017). As the present invention involves the administration of high doses of glucocorticoids, formulations with low levels of potentially toxic preservatives, or formulations without toxic preservatives, should be used. Preferably, the preservative is an antioxidant.

The pharmaceutical composition of the invention may include a preservative (e.g. an antioxidant) additive such as sodium sulfite to maintain the stability of the composition. Sulfites are also widely used as preservative and antioxidant additives in the pharmaceutical industries. Exposure to such sulfites has been reported to induce a range of adverse clinical effects in sensitive individuals, ranging from dermatitis, urticaria, flushing, hypotension and abdominal pain to life-threatening anaphylactic and asthmatic reactions. Sulfite-inducing symptoms range from mild in some individuals, to severe in others, and in some individuals the reactions can be life threatening. In preferred embodiments, where sodium sulfite is included as an antioxidant, the concentration is between 0-70 ppm Sodium Sulfite (Anhydrous).

Antioxidants may be added in amounts that are reduced from those levels typically employed in glucocorticoid containing compositions thereby reducing the toxicity and adverse side effects associated with the use of such antioxidants. In some instances, the formulations of the invention may lack the addition of antioxidants.

As used herein, antioxidants are those excipients that delay or inhibit the oxidation process of molecules thereby increasing the stability of the composition. Antioxidants that may be used include, for example, ascorbic acid, acetylcysteine, butylhydroxyanisol, cysteine hydrochloride, dithionite sodium, gentisic acid, glutamate monosodium, glutathione, formaldehyde sulfoxylate sodium, methionine, monothioglycerol, propyl gallate, sulfites, sodium thioglycolate, α-thioglycerol, tocopherol alpha, alpha tocopherol hydrogen succinate and thioglycolate sodium.

In addition to an active glucocorticoid and antioxidant, additional components well known to those of skill in the art may be included in the pharmaceutical compostions disclosed herein. Pharmaceutical compositions may be prepared using a pharmaceutically acceptable "carrier" composed of materials that are considered safe and effective. "Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In some embodiments, this term refers to molecular entities and compositions approved by a regulatory agency of the US federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

The term "carrier" refers to diluents, binders, lubricants and disintegrants. Those with skill in the art are familiar with such pharmaceutical carriers and methods of compounding pharmaceutical compositions using such carriers.

The pharmaceutical compositions provided herein may include one or more excipients, e.g., solvents, solubility enhancers, suspending agents, buffering agents, isotonicity agents, antioxidants or antimicrobial preservatives. When used, the excipients of the compositions will not adversely affect the stability, bioavailability, safety, and/or efficacy of the active ingredients, ie., glucocorticoids, used in the composition. Thus, the skilled person will appreciate that compositions are provided wherein there is no incompatibility between any of the components of the dosage form. Excipients may be selected from the group consisting of buffering agents, solubilizing agents, tonicity agents, chelating agents, antioxidants, antimicrobial agents, and preservatives.

The pharmaceutical composition of the invention may include a chelating agent which is used to sequester and decrease the reactivity of metal ions that may be present in the compositions. Possible chelators are calcium disodium EDTA 0.01-0.1% (EDTA=Ethylenediaminetetra acetic acid or Edetate), Disodium EDTA 0.01-0.11%, Sodium EDTA 0.20%, Calcium Versetamide Sodium 2.84%, Calteridol 0.023%, DTPA 0.04-1.2% (Diethylenetriaminepenta acetic acid). In a preferred embodiment the concentration of Disodium EDTA (Edetate) is between 0 and 500 ppm.

As noted in International patent application PCT/US2018/025517 (filed 30 Mar. 2018), glucocorticoids can also be used as a preconditioning agent, in conjunction with adoptive cell therapies (ACT). Glucocorticoids, particularly dexamethasone dosed between about 3 mg/kg and about 26 mg/kg single acute dose about 12 to about 72 hours prior to cell immunotherapy administration or total dose of about 15 mg/kg to about 26 mg/kg given between about 12 to about 72 hours of cell therapy administration increases plasma IL-2 and IL-15 levels.

Glucocorticoids, particularly dexamethasone dosed between about 15 mg/kg and about 26 mg/kg single acute dose or total dose of about 15 mg/kg to about 26 mg/kg given over about a 72 hour period, either alone, or in combination with reduced intensity cytotoxic preconditioning can be useful for the treatment of autoimmune diseases. For the treatment of autoimmune disease an ACT could be targeted to the immune cells driving the disease in an effort to eradicate the autoimmune recognizing cells. Additionally, for autoimmune diseases the ACT could be a Treg targeted by a CAR or TCR or expressed antibody for an antigen expressed specifically or selectively by the region or organ of the body where the autoimmune attack goes on. The Tregs could non-exclusively relate to CD4+Tregs, CD4+CD45RA+Tregs, CD4+CD25+CD45RA+Tregs, FoxP3+Tregs, CD4+CD25+FoxP3+CD152+Tregs, CD4+CD25+CD152+Tregs, CD8+Tregs, CD8+CD28−Tregs, CD4+CD25int/high, CD127low, CTLA4+, GITR+, FoxP3+, CD127low, CD4+CD25−⁻ induced Tregs, or Type I T regs.

"Natural" regulatory T cells originally recognised by their constitutive expression of CD4 and CD25 can be further defined by expression of the transcription factor foxP3 and surface CD152. Their generation and some of their suppressive activity is dependent on TGF-beta, and it has been shown that they can induce IDO in appropriate DCs by CD152 mediated ligation of CD80/86. Anergic CD4+ T cells generated by antigen stimulation in the absence of costimulation seem to be characterised by an intrinsic raising of their threshold for antigen stimulation that may be maintained by expression of E3 ubiquitin ligases such as GRAIL, c-cbl and Itch. Anergic cells can act as regulatory T cells by competing at the sites of antigen presentation and adsorbing out stimulatory cytokines such as IL-2. Tr1 cells represent an induced subset of CD4 helper T cells that are dependent on IL-10 for their differentiation and for some of their regulatory properties. They do not express foxP3 but may express markers associated with Th2 cells and repressor of GATA (ROG). Like natural Tregs, they express high levels of surface CD152 and can induce IDO and trypophan catabolism in appropriate DCs. CD8+CD28− suppressor T (Ts) cells were first characterised in human, but have recently also been demonstrated in rodents. Like Tr1 cells, they are induced in the presence of IL-10, and IL-10 may be involved in the downregulation of dendritic cell costimulation and the upregulation of ILT-3 and ILT-4 (in human DC) that seem to play an important role in presenting antigen to tolerise further cohorts of T cells.

Regulatory T cells (Tregs) play an important role in maintaining immune homeostasisl. Tregs suppress the function of other T cells to limit the immune response. Alterations in the number and function of Tregs has been implicated in several autoimmune diseases including multiple sclerosis, active rheumatoid arthritis, and type 1 diabetes. High levels of Tregs have been found in many malignant disorders including lung, pancreas, and breast cancers. Tregs may also prevent antitumor immune responses, leading to increased mortality.

Two major classes of Tregs have been identified to date: CD4 and CD8 Tregs. CD4 Tregs consist of two types, "natural" Tregs (nTregs) that constitutively express CD25 and FoxP3, and so-called adaptive or inducible Tregs (iTregs).

Natural Tregs (nTregs) originate from the thymus as $CD4^+$ cells expressing high levels of CD25 together with the transcription factor (and lineage marker) FoxP3. nTregs represent approximately 5-10% of the total $CD4^+$ T cell population, and can first be seen at the single-positive stage of T lymphocyte development. They are positively selected thymocytes with a relatively high avidity for self-antigens. (Fehérvari Z, Sakaguchi S. Development and function of $CD25^+CD4^+$ regulatory T cells. *Curr Opin Immunol.* 2004; 16:203-208.)

The signal to develop into Treg cells is thought to come from interactions between the T cell receptor and the complex of MHC II with self peptide expressed on the thymic stroma. nTregs are essentially cytokine independent.

Adaptive or inducible Tregs originate from the thymus as single-positive CD4 cells. They differentiate into CD25 and FoxP3 expressing Tregs (iTregs) following adequate antigenic stimulation in the presence of cognate antigen and specialized immunoregulatory cytokines such as TGF-β, IL-10, and IL-4. (Chatenoud L, Bach J F. Adaptive human regulatory T cells: myth or reality? *J Clin Invest.* 2006; 116:2325-2327.)

FoxP3 is currently the most accepted marker for Tregs, although there have been reports of small populations of FoxP3⁻ Tregs. The discovery of transcription factor FoxP3 as a marker for Tregs has allowed scientists to better define Treg populations leading to the discovery of additional Treg markers including CD127.

Glucocorticoids, particularly dexamethasone dosed between about 15 mg/kg and about 26 mg/kg single acute dose or total dose of about 15 mg/kg to about 26 mg/kg given over about a 72 hour period, either alone or in combination with reduced intensity cytotoxic chemotherapy or radiation can be useful for the treatment of residual HIV disease, and for the treatment of germinal center lymphomas such as Burkitt's Lymphoma.

Follicular helper CD4 T cells, $T_{FH}$, residing in B-cell follicles within secondary lymphoid tissues, are readily infected by AIDS viruses and are a major source of persistent virus despite relative control of viral replication. This persistence is due at least in part to a relative exclusion of effective antiviral CD8 T cells from B-cell follicles. AIDS virus persistence in individuals under effective drug therapy or those who spontaneously control viremia remains an obstacle to definitive treatment. Infected follicular helper CD4 T cells, $T_{FH}$, present inside B-cell follicles represent a major source of this residual virus. While effective CD8 T-cell responses can control viral replication in conjunction with drug therapy or in rare cases spontaneously, most antiviral CD8 T cells do not enter B-cell follicles, and those that do fail to robustly control viral replication in the $T_{FH}$ population. Thus, these sites are a sanctuary and a reservoir for replicating AIDS viruses. Lymphodepletion and reduction of germinal centers and marginal zones in the spleen would force residual HIV infected cells into the blood stream where they could be killed by existing therapies. Latently infected resting CD4 T cells have been detected in the peripheral blood, gastrointestinal (GI) tract, and lymph nodes of HIV-1-infected individuals and are also likely to exist in other organs containing lymphoid tissue.

Highly active antiretroviral therapy (HAART) enables long-term suppression of plasma HIV-1 loads in infected persons, but low-level virus persists and rebounds following cessation of therapy. During HAART, this virus resides in latently infected cells, such as resting CD4 T cells, and in other cell types that may support residual virus replication. Therapeutic eradication will require elimination of virus from all reservoirs.

Burkitt's Lymphoma is a germinal center lymphoma originating and growing within the secondary lymphatic system, always associated with a c-Myc activating chromosomal translocation. It is one of the fastest growing cancers and can double in size every 14-18 hours. BL is an aggressive B-cell lymphoma found in germinal centers of the spleen and secondary lymphatics. BL is named after Dr. Denis Parsons Burkitt, a surgeon who first described the disease in 1958 while working in equatorial Africa (Burket, D., 1958). BL is most commonly found in children living in sub-Saharan Africa, with the highest incidence and mortality rates found in East Africa (Orem, J., et al.). Boys are more susceptible to BL than girls. Outside of Africa, BL is most likely to occur in people who have a compromised immune system.

Among B-cell malignancies, CLL is the most responsive to ibrutinib, and thus unfortunately ibrutinib is not likely to significantly benefit people afflicted with Burkitt's Lymphoma and other germinal center lymphomas. However, the same result to redistribute B-cell cancers into the circulation where they are more susceptible to chemotherapy and less proliferative can be achieved for germinal center lymphomas such as Burkitt's lymphoma with the use of agents that ablate secondary lymphatic germinal centers.

Clinical observations on the ability of a Bruton's Tyrosine Kinase inhibitor ibrutinib for treatment of chronic lymphocytic leukemia has demonstrated that redistribution of CLL cells from the lymphatics into the bloodstream is a contributing mechanism of action to its benefit in CLL. Circulating CLL cells are not proliferative, with proliferation of the clone limited to the lymphatic microenvironment. Therefore, redistribution into the blood stream reduces cancerous proliferation. Similarly, redistribution of ALL from the bone marrow to the bloodstream, has also been reported to enhance sensitivity to standard chemotherapy (Chang B Y, Blood 2013 122: 2412-24).

Glucocorticoids have been reported to have multiple and contradictory actions on lymphocytes, depending on the dose, the duration of dosing and the species investigated. Glucocorticoids have been investigated as lymphocytosis inducing agents, agents which increase circulating lymphocyte numbers, since 1943 (for review see Burger et al., 2013), typically with the use of prednisone between 0.5 and 1 mg/kg, which would be an equivalent 0.1-0.2 mg/kg dexamethasone dose. High dose methylprednisone (HDMP) used for refractory CLL, in contrast, does not appear to induce lymphocytosis at the methylprednisone equivalent to the 0.5-1.0 mg/kg dose at which prednisone did. Lymphotoxic high-dose steroids are typically considered to be approximately 100 mg daily of prednisone equivalent, which would be a dexamethasone equivalent dose of 16 mg which is approximately 0.23 to 0.32 mg/kg, and which we have demonstrated is not an effective preconditioning dose. Dexamethasone does not reduce germinal centers in mice until an HED of about 3 mg/kg or greater is administered. Prednisone does not significantly impact spleen weights or germinal centers until used at doses in mice over 2.5 mg/kg po daily for 13 weeks (Yan et al., 2015), a human dose which would have unacceptable mineralocorticoid activity as a dose of 30 mgs per day (~0.48-0.72 mg/kg) is considered a high dose in human lupus patients.

For Burkitt's lymphoma (BL) treatment with standard chemotherapy regimens such as COPADM, prednisone is included in various cycles typically at 60 mg/m$^2$, which converts to 1.62 mg/kg prednisone and an equivalent 0.3 mg/kg dexamethasone dose, which is not an effective preconditioning dose. Dexamethasone is also used clinically for the treatment of B-cell cancers, typically in an oral four-five day 40 mg daily regimen or 6 mg/m$^2$ for 5 days. In some indications such as ALL, dexamethasone is given daily for weeks and can be associated with osteonecrosis, particularly in adolescent boys. Risk of osteonecrosis can be substantially eliminated by alternate week dosing of dexamethasone and may be particularly present in ALL because of the asparaginase regimen that is part of the treatment for ALL (Chang B Y, Blood 2013 122: 2412-24).

Epstein-Barr virus (EBV) infection is found in nearly all African BL patients, and chronic malaria is believed to reduce resistance to EBV, allowing it to take hold. The disease characteristically involves the jaw or other facial bone, distal ileum, cecum, ovaries, kidney, or breast. Additionally, BL strikes immunocompromised people, such as those with HIV.

BL is classified into three main clinical variants: Endemic, Sporadic, and the Immunodeficiency-associated variants, with the Endemic variant (also called the "African variant") most commonly occurring in children living in malaria endemic regions of the world.

One effect of the present invention can be to ablate germinal centers and/or marginal zones to selectively drive BL and other germinal center cancer cells or marginal zone cancer cells from the germinal centers or marginal zones into circulation where they can be more easily killed with chemotherapy or other agents. This could dramatically, safely and cost-effectively advance BL treatment outcomes. Asthma is a chronic inflammation characterized by an increased number of CD8+ Type-1 T-lymphocytes and macrophages in the lung tissue and neutrophils in the airway lumen. Lymphocytes, which are markedly different in the two inflammatory conditions, play a crucial role in the pathogenesis of asthma and COPD. There is now overwhelming evidence to support a major role for T cells in asthma, in particular the involvement of T helper type 2 (Th2) cells in atopic allergic asthma as well as nonatopic and occupational asthma. There may also be a minor contribution from T cytotoxic type 2 CD8+ T cells. Several Th2 cytokines have potential to modulate airway inflammation, in particular interleukin-13 which induces airway hyperresponsiveness independently of IgE and eosinophilia in animal models. Asthma and chronic obstructive pulmonary disease (COPD) are two different inflammatory disorders of the lungs which share a common functional abnormality, i.e. airflow limitation (Baraldo et al., 2007).

In asthma, airflow limitation is largely reversible, either spontaneously or with treatment, and does not progress in most cases. On the other hand, airflow limitation in COPD is usually progressive and poorly reversible. In asthma, the chronic inflammation causes an associated increase in airway responsiveness to a variety of stimuli, leading to recurrent episodes of wheezing, breathlessness, chest tightness and cough, particularly at night and in the early morning. Many cells are involved in the inflammatory response in asthma and, among these, CD4+ Type-2 lymphocytes, mast cells and eosinophils are thought to play a crucial role. In COPD, the poorly reversible airflow limitation is associated with an abnormal inflammatory response of the lungs to noxious particles or gases. This chronic inflammation is characterized by an increased number of CD8+ Type-1 T-lymphocytes and macrophages in the lung tissue and neutrophils in the airway lumen. Lymphocytes, which are markedly different in the two inflammatory conditions, play a crucial role in the pathogenesis of asthma and COPD (Baraldo et al., 2007).

Definitions

Definitions used to describe the embodiments of the invention:

Biologic mechanism of lymphodepletion means induction of programmed cell death via apoptosis or necroptosis or pyroptosis or autophagy or oncosis. Various stimuli can engage a non-apoptotic form of cell death called necroptosis, which occurs when caspases required for apoptosis are inhibited. Pyroptosis is a caspase-dependent form of programmed cell death that differs in many respects from apoptosis. Unlike apoptosis, it depends on the activation of caspase-1 or caspase-11 (caspase-5 in humans). Autophagy is a lysosome-dependent process.

Apoptosis: A form of cell death in which a programmed sequence of events leads to the elimination of cells without releasing harmful substances into the surrounding area. Apoptosis plays a crucial role in developing and maintaining the health of the body by eliminating old cells, unnecessary cells, and unhealthy cells.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about' when referring to a measurable value such as an amount or a temporal duration and the like refers to variations of +/−20% or +/−10%.

Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically.

A pharmacologic dose is a dose far in excess of normal levels in the body.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A therapeutic agent is an agent that enhances the efficacy of cellular immunotherapies compared to the cellular immunotherapies without said therapeutic agent.

The term "autologous" refers to any material derived from the same individual to which it is later to be re-introduced, whether the individual is a human or other animal.

The term "allogeneic" refers to any material derived from one individual which is then introduced to another individual of the same species, whether the individual is a human or other animal.

The term dexamethasone (also referred to as Dex) non-exclusively relates to any formulation whether a liquid solution, liquid suspension, oral solution, tablet form, tablet form dissolved in a liquid containing the active ingredient of dexamethasone, injectable form, gel formulation, patch formulation or any formulation containing the active ingredient dexamethasone.

The term glucocorticoid-receptor modulating agents non-exclusively relates to glucocorticoid receptor agonists or glucocorticoid receptor modulators including but not limited to: compound A [CpdA; (2-((4-acetophenyl)-2-chloro-N-methyl)ethylammonium-chloride)] and N-(4-methyl-1-oxo-1H-2,3-benzoxazine-6-yl)-4-(2,3-dihydrobenzofuran-7-yl)-2-hydroxy-2-(trifluoromethyl)-4-methylpentanamide (ZK216348), AL-438, Mapracorat, LGD-5552, RU-24858, Fosdagrocorat, PF-802, Compound 10, MK5932, C108297, LGD5552, and ORG 214007-0.

Immunotoxins are proteins that contain a toxin along with an antibody or growth factor that binds specifically to target cells. Immunotoxins are created by chemically conjugating an antibody to a whole protein toxin, devoid of its natural binding domain. Immunologic proteins that are smaller than monoclonal antibodies (MoAbs), like growth factors and cytokines, have also been chemically conjugated and genetically fused to protein toxins. Toxins used in immunotoxin constructs are derived from bacteria, fungi, and plants, and most function by inhibiting protein synthesis. Bacterial toxins commonly used in immunotoxins include Diphtheria toxin (DT) and the toxin from *Pseudomonas* exotoxin (PE). Plant toxins utilized in immunotoxins include the A chain of ricin (RTA), and the ribosome inactivating proteins (RIPs)

gelonin, pokeweed antiviral protein, and dodecandron. Because it is an enzyme, one toxin molecule can work on many substrate molecules, having a devastating effect on the cell. Toxins such as diphtheria toxin (DT) and *Pseudomonas* exotoxin (PE) prevent protein synthesis by an effect on elongation factor 2 (EF-2).

The term systemic injection as used herein non-exclusively relates to a route of administration that rapidly, within seconds or a few hours, leads to circulating levels of cellular immunotherapies, and non-exclusively relates to intravenous, intraperitoneally, subcutaneous, via nasal submucosa, lingual, via bronchoscopy, intravenous, intra-arterial, intramuscular, intro-ocular, intra-striatal, subcutaneous, intradermal, by dermal patch, by skin patch, by patch, into the cerebrospinal fluid, into the portal vein, into the brain, into the lymphatic system, intra-pleural, retro-orbital, intra-dermal, into the spleen, intra-lymphatic, among others.

The term 'site of injection' as used herein non-exclusively relates to intra-tumor, or intra-organ such as the kidney or liver or pancreas or heart or lung or brain or spleen or eye, intra-muscular, intro-ocular, intra-striatal, intradermal, by dermal patch, by skin patch, by patch, into the cerebrospinal fluid, into the brain, among others.

The term lymphodepletion as used herein non-exclusively relates to the reduction of lymphocyte number in the peripheral blood without causing redistribution of lymphocytes to another organ such as the bone marrow, thymus, lymph nodes, lung or spleen or another organ.

The term lymphoablation as used herein non-exclusively relates to reduction of lymphocyte number in the peripheral blood to below 200 per microliter, preferably to below 100 per microliter, without causing redistribution of lymphocytes to another organ such as the bone marrow, thymus, lymph nodes, lung or spleen or another organ.

The term cytotoxic lymphodepletion as used herein relates to the reduction of lymphocyte number in the peripheral blood by a mechanism of ADCC, cell-mediated cytotoxicity or direct lysis or cytotoxic elimination of lymphocytes, chemotherapy or radiation.

The antibody-dependent cell-mediated cytotoxicity (ADCC), also referred to as antibody-dependent cellular cytotoxicity, is a mechanism of cell-mediated immune defense where an effector cell of the immune system actively lyses a target cell, whose membrane-surface antigens have been bound by specific antibodies.

The term 'cellular immunotherapy', 'adoptive cellular immunotherapy', 'adoptive cellular therapy' (ACT) or cell immunotherapy or cell therapy as used herein non-exclusively relates to treatments that contain a cell used to help the immune system fight diseases or a cell from the immune lineage which directly fights diseases such as cancer, autoimmune diseases and infections with certain viruses. The cellular immunotherapy can be from either an autologous or allogeneic source. In preferred embodiments, the adoptive immunotherapy used in the methods disclosed herein may be an adoptive T cell immunotherapy, i.e. 'T cell therapy'.

The term preconditioning as used herein relates to the preparation of a patient with a cytotoxic lymphodepleting agent or a non-toxic lymphodepleting agent prior to ACT.

The term immunotherapy, also called biologic therapy, as used herein non-exclusively relates to a type of treatment for cancer, autoimmune disease or infection treatment designed to boost the body's natural defenses to fight the cancer, autoimmune disease or infection. It uses substances either made by the body or in a laboratory to improve or restore immune system function. The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The term 'immune modulation' as used herein non-exclusively relates to, in cancer, autoimmune disease or infection, a range of treatments aimed at harnessing a patient's immune system to achieve tumour, autoimmune causing cell or viral control, stabilization, and potential eradication of disease.

The term immunomodulator as used herein non-exclusively relates to a chemical agent (such as dexamethasone) or biologic agent (such as HUMIRA® and rituximab) that modifies the immune response or the functioning of the immune system (as by the stimulation of antibody formation or the inhibition of white blood cell activity). Traditional immune modulating drugs that are immunesuppressants non-exclusively relates to glucocorticoids, calcineurin inhibitors, antimetabolites, and alkylating agents. Antimetabolites non-exclusively relates topurine analogues (e.g., azathioprine and mycophenolate mofetil), and folate antagonists (e.g., methotrexate and dapsone).

Immunesuppressants (also termed immunosuppressants) can be chemical or biologic agents that can suppress or prevent the immune response. For instance, antagonists to CD26 and dexamethasone are immunesuppressants. The NTLAs used in this invention may be NTLA immunesuppressants.

The terms "conditioning" and "pre-conditioning" are used interchangeably herein and indicate preparing a patient or animal in need of a T cell therapy for a suitable condition. Conditioning as used herein includes, but is not limited to, reducing the number of germinal centers and marginal zones, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy.

The term 'adoptive immunotherapy' or 'cellular adoptive immunotherapy' as used herein non-exclusively relates to immune cells that are collected from a patient (autologous or autogenic) or a donor (allogeneic), either related or unrelated, and grown in the laboratory. This increases the number of immune cells that are able to kill cancer cells, autoimmune causing cells or fight infections. These immune cells are given back to the patient to help the immune system fight disease. This is also called cellular adoptive immunotherapy. The immune cell can be a T cell and/or other cell of the immune system non-exclusively relating to macrophages, monocytes, dendritic cells, neutrophils, granulocytes, phagocytes, mast cells, basophils, thymocytes, or innate lymphoid cells, or any combination thereof.

The term agonist as used herein non-exclusively relates to any entity that activates a specific receptor or downstream signaling pathway essential to mediate the receptor's effect(s). Agonists may non-exclusively relates to but are not limited to antibodies, antibody fragments, soluble ligands, small molecules, cyclic peptides, cross-linking agents.

The term antagonist as used herein non-exclusively relates to any entity that interferes with the binding of a receptor's counter structure(s), or with the activation of a specific receptor or downstream signaling pathway essential to mediate the receptor's effect(s). Antagonists may non-exclusively relates to but are not limited to antibodies, antibody fragments, soluble ligands, Fc fusion receptors, chimeric receptors, small molecules, cyclic peptides, peptides.

The term inhibitor as used herein non-exclusively relates to any entity that diminishes the target effect of a specific receptor. Inhibitors may be small molecules, antisense agents, nucleic acids including siRNA and microRNA.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CDS+ T-cells or killer T cell), Memory T-cells ((i) stem memory T scM cells, like naive cells, are CD45RO−, CCR 7+, CD45RA+, CD62L+(L-selectin), CD27+, CD28+ and IL-7Ra+, but they also express large amounts of CD95, IL-2R~, CXCR3, and LFA-1, and show numerous functional attributes distinctive of memory cells); (ii) central memory TcM cells express L-selectin and the CCR7, they secrete IL-2, but not IFNy or IL-4, and (iii) effector memory T EM cells, however, do not express L-selectin or CCR 7 but produce effector cytokines like IFNy and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen presenting cells (APCs) and turns into memory B-cells after activation by antigen interaction. In manmials, immatureB-cells are formed in the bone marrow, where its name is derived from.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" is assessed by measurement of malignant lesions on radiographs or other methods should not be reported as adverse events. Death due to disease progression in the absence of signs and symptoms should be reported as the primary tumor type (e.g., DLBCL).

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20% (i.e., ±20%). For example, about 3 mg can include any number between 2.3 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Ranges: Various aspects of the invention are presented in range format. The description in range format is for convenience and brevity and should not be construed as an inflexible limitation on the scope of the invention. Accordingly, the description of a range should be considered to have specifically disclosed all the possible subranges as well as individual numerical values within that range. For example, a range from 3 to 12 includes 3.1, 3.2, 3.3 etc.

Autoimmune disorders and other diseases that are mediated by lymphocytes and which are in need of treatments that are simpler and less costly than HSCT are related to, but not limited by the following list; allergies, asthma, residual HIV, residual malaria, germinal center lymphomas such as Burkitts Lymphoma and Diffuse Large B cell Lymphoma, marginal zone lymphoma graft versus host disease (GvHD), steroid-resistant GvHD, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optic), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease In certain embodiments of this invention one might want to exclude diseases such as allergies, asthma, residual HIV, residual malaria, germinal center lymphomas such as Burkitts Lymphoma and Diffuse Large B cell Lymphoma, marginal zone lymphoma, graft versus host disease (GvHD), steroid-resistant GvHD, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optic), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease.

Further Discussion of the Immune Setting of the Invention

The spleen contains both a white pulp and a red pulp. The red pulp of the spleen holds macrophages that normally filter and remove senescent or defective red blood cells (RBCs) and antibody-coated bacteria or red blood cells from the circulation. The white pulp of the spleen contains the lymphoid compartments and is crucial for immune surveillance and response: it synthesizes antibodies against invading pathogens and releases platelets and neutrophils in response to bleeding or infection. During development the spleen is believed to have multiple roles including being the first site of hematopoiesis (at six weeks of gestation). Preclinical and clinical trials have demonstrated that without cytotoxic chemotherapy preconditioning, cellular immunotherapies are cleared from the circulation, largely within one hour after administration, and accumulate in the spleen. The cytotoxic chemotherapy preconditioning must be immediate to administration of the cellular immunotherapies in order to maintain the cellular immunotherapies in the circulation, typically 48 hours before administration of the cellular immunotherapies. When cytotoxic chemotherapy preconditioning is given 4 weeks before or at a pretreatment time which allows bone marrow recovery, it is not effective to keep the cellular immunotherapies in the circulation Ritchie D S et al. Mol Ther. November; 21(11): 2122-9 (2013)

The periarterial lymphoid sheaths (PALS) of the white pulp of the spleen are populated mainly by T cells, while the lymphoid portions are populated mainly by B cells. Germinal centers (GC) are sites within lymph nodes or lymph nodules in peripheral lymph tissues, and in the white pulp of the spleen where intense mature B lymphocytes, otherwise known as Centrocytes rapidly proliferate, differentiate, mutate through somatic hypermutation and class switch during antibody responses. Germinal centers are an important part of the B-cell humoral immune response. They develop dynamically after the activation of B-cells by T-dependent antigen. Histologically, the GCs describe microscopically distinguishable parts in lymphoid tissues. Activated B-cells migrate from the primary focus into the primary follicles follicular system and begin monoclonal expansion in the environment of follicular dendritic cells (FDC).

After several days of expansion the B cells mutate their antibody-encoding DNA and thus generate a diversity of clones in the germinal center. This involves random substitutions, deletions and insertions due to somatic hypermutation. Upon some unidentified stimulus from the FDC, the maturing B cells (Centroblasts) migrate from the dark zone to the light zone and start to expose their antibody to their surface and in this stage are referred to as Centrocytes. The Centrocytes are in a state of activated apoptosis and compete for survival signals from FDCs that present the antigen. This rescue process is believed to be dependent on the affinity of the antibody to the antigen. The functional B-cells have then to interact with helper T cells to get final differentiation signals. This also involves isotype switching for example from IgM to IgG. The interaction with T cells is believed to prevent the generation of autoreactive antibodies. The B cells become either a plasma cell spreading antibodies or a memory B cell that will be activated in subsequent contacts with the same antigen. They may also restart the whole process of proliferation, mutation and selection according to the recycling hypothesis.

The B cells contained within the white pulp region of the spleen can be further divided into specific areas, identified by staining with specific molecular markers. The marginal zone of the spleen contains noncirculating mature B cells that border on the white pulp creating a separation between the white and the red pulp and express high levels of CD21 and IgM and CD24 and CD79a, and measurable levels of CD9 and CD22. The mantle zone surrounds normal germinal center follicles and expresses CD21, CD23 and CD38. The follicular zone is contained within the germinal centers and expresses high levels of IgD and CD23, intermediate levels of CD21 and CD24, and can also be identified by PNA staining. The germinal center is best distinguished by PNA binding and expresses higher levels of CD54 than the follicular zone. Germinal centers have a special population of helper T cells that seem to distribute evenly in all germinal centers. Germinal centers are traditionally associated with immune responses that require T helper cells, although this is not absolute. Germinal centers are where hypervariable gene mutation occurs and high affinity IgG producing B cells are generated. Active germinal centers have tangible macrophages and CD21 expressing dendritic cells. Follicular centers can also be identified by the expression of CD45R (B220) (Cytotoxicologic Pathology, 35:366-375, 2007). CD45R follicular centers are found surrounding germinal centers expressing Bcl6 and Bcl2. BioEssays 29:166-177, 2007; Cytotoxicol Pathol 34(5): 648-655, (2006)]

The response to pathogens or cancer cells is orchestrated by the complex interactions and activities of the large number of diverse cell types involved in the immune response. The innate immune response is the first line of defense and occurs soon after pathogen exposure. It is carried out by phagocytic cells such as neutrophils and macrophages, cytocytotoxic natural killer (NK) cells, and granulocytes. The subsequent adaptive immune response elicits antigen-specific defense mechanisms and may take days to develop. Cell types with critical roles in adaptive immunity are antigen-presenting cells including macrophages and dendritic cells. Antigen-dependent stimulation of various cell types including T cell subsets, B cells, and macrophages all play critical roles in host defense. Immune cells non-exclusively relates to: B Cells, Dendritic Cells, Granulocytes, Innate Lymphoid Cells (ILCs), Megakaryocytes, Monocytes/Macrophages, Myeloid-derived Suppressor Cells (MDSC), Natural Killer (NK) Cells, Platelets, Red Blood Cells (RBCs), T Cells, Thymocytes.

Zwang et al (2014) have shown that, following lymphodepletion, lymphocytes repopulate the immune space both through enhanced thymopoiesis and proliferation of residual non-depleted peripheral lymphocytes. The term homeostatic proliferation (alternatively homeostatic expansion or lymphopenia-induced proliferation) refers to the latter process. Homeostatic proliferation is especially relevant to reconstitution of the lymphocyte compartment following immunodepletion therapy in transplantation. Repopulating lymphocytes can skew toward an effector memory type capable of inducing graft rejection, autoimmunity, or, in the case of allogeneic bone marrow transplantation, graft versus host disease.

Two immune-depleting agents, alemtuzumab and rabbit antithymocyte globulin, have been well-characterized in their abilities to induce an effector-memory phenotype in repopulating lymphocytes.

Early studies of homeostatic proliferation showed that T cells surviving lymphodepletion divided, developed memory phenotype and function, and then acted in a dominant fashion to render animals resistant to cardiac or renal allograft tolerance via costimulatory blockade.1,2 In line with these findings, recent studies have shown that lymphopenia itself is enough to break stable costimulatory blockade-based peripheral tolerance.3 In a mouse model of MHC-mimatched cardiac transplantation, lymphopenia (achieved either by irradiation or anti-CD4+/CD8+ monoclonal antibodies) induced acute T and B cell-mediated rejection, accompanied by a T cell shift toward a CD44hi effector-memory (EM) phenotype and the appearance of donor-specific antibodies. The process of homeostatic proliferation can be divided into "slow" (one cell division per 24-36 hours) or "fast" (one division per 6-8 h) kinetics. While slow proliferation occurs in response to a "sensing of empty space", rapid proliferation is primarily a gut antigen-driven process.4 Slow homeostatic proliferation predominates in homeostatic proliferation following lymphodepletion in mouse models. Furthermore, both T and B cells can undergo homeostatic proliferation.

Alemtuzumab (anti-CD52) is a potent lymphocyte depletional agent that has been used as induction therapy for transplantation and for treatment of multiple sclerosis. CD4+ cells and, to a lesser extent, naïve CD8+ cells, are most susceptible to alemtuzumab-induced lymphodepletion.5,6,7,8 A larger population of naïve T cells may remain undeleted, however, as peripheral lymph nodes may be a reservoir for these cells following alemtuzumab induction.9 Alemtuzumab therapy leads to skewing toward memory CD4+ and CD8+ phenotypes in renal transplant recipients; those with evidence of rejection (by biopsy, new or donor-specific antibodies) following alemtuzumab therapy have an increased proportion of CD8+ effector memory cells (CD45RO–CD62L–).10 These same patients further have decreased frequencies of regulatory T cells (Tregs) among CD4+ cells. While other work, in contrast, has suggested an increased frequency of Foxp3+ cells following alemtuzumab induction.11 It is possible that in this instance Foxp3 expression may be only a transient marker of T cell activation.12,13, 14 Among patients with multiple sclerosis, homeostatic proliferation following alemtuzumab therapy leads to recovery of a highly activated, proliferative, oligoclonal, and memory-like population of CD4+ and CD8+ cells.15 In particular, the CD8 pool is dominated by a terminally-differentiated, effector memory CD28–CD57+ CD8 population expressing perforin and Granzyme B. Such as population is known to be associated with autoimmunity, and indeed in this study of 87 patients, two thirds developed (primarily thyroid) autoimmunity.

Recent examination of the kinetics of lymphocyte depletion following rATG given as induction therapy in renal transplantation found that rATG durably depletes the T cell compartment to counts below 250 CD3+ cells/uL at six months, compared to minimal T cell depletion following basiliximab or no induction therapy.19 In contrast to prior studies, this recent investigation found no increase in thymopoiesis (i.e., CD31+ cells among CD4+ or CD8+ cells) one month following rATG induction. Rather, peripheral cytokine-mediated signaling by IL-7 and IL-15 via StatS increased in the first month following rATG therapy, particularly among memory T cell subsets. These studies indicate that T cell recovery following ATG comes from peripheral T cell pools rather than heightened thymopoiesis.

In humans, unlike mice, the majority of proliferating T cells derives from the periphery rather than the thymus.20 Therefore, peripheral cytokine signaling is essential to maintain the lymphoreplete state and repopulate the T cell compartment in lymphopenia. IL-7 is the primary cytokine responsible for T cell homeostatic proliferation. In young thymectomized and elderly adults, circulating IL-7 levels are higher than those of healthy controls.21 IL-7 in these patients with low or no thymic function appears to stimulate T cell proliferation via STAT5 signaling. IL-7 itself has been described as a "rheostat" to maintain the T cell compartment.22 In lymphopenia, excess IL-7 stimulates T cell proliferation. Proliferating T cells consume IL-7, and levels fall to the basal state as the T cell compartment repopulates. This mechanism prevents excess proliferation and preserves T cell homeostasis. A recent study found that IL-7-induced proliferation requires intermittent (rather than continuous) signaling and that TCR engagement provides this interruption.23 T cells with inadequate affinity for peripheral (self) TCR ligands die following prolonged IL-7 signaling; this mechanism maintains a population of T cells with appropriate affinity for self ligands. In addition to IL-7, IL-15 signaling is important for CD8+ T cell survival and proliferation.24,25,26 While IL-15 enhances homeostatic proliferation of memory CD8+ cells, IL-15 alone is not enough for homeostatic proliferation of naïve CD8 T cells. 27 In naïve CD8+ cells, MHC I engagement is also necessary for homeostatic proliferation.28 Emerging data show that memory CD4+ may also be responsive to IL-15.29,30,31 Finally, TGB-β may attenuate IL-15 signaling and act as a brake on homeostatic proliferation-driven autoimmunity.32, 33, 34,35,36,37

The protein tyrosine phosphatase gene product PTPN2, which dampens TCR signaling in CD4+ and CD8+ cells, is implicated in human autoimmunity.38,39 T cell knockout of PTPN2 in a mouse model resulted in more rapid lymphopenia-induced CD8+ proliferation compared to control animals. Adoptive transfer of PTPN2-deleted CD8+ cells into congenic hosts resulted in effector/memory differentiation and autoimmunity compared to adoptive transfer of control CD8+ cells.40 This response was IL-7-independent. miRNA-181a enhances TCR signaling, in part by suppressing expression of other protein phosphatases.41 Thus, miRNA-181 or another miRNA might inhibit PTPN2 expression and thereby dampen lymphopenia-induced proliferation. It has been suggested that transcription factors may regulate the ability of hematopoietic stem cells to repopulate the lymphocyte compartment. For example, Hoxb4 signaling may promote a hematopoietic stem cell CD4+ central memory (CD44hiCD62L+) phenotype in response to lymphopenia.42 In competitive adoptive transfer experiments, Hoxb4− overexpressing central memory cells contributed less than wild-type central memory cells to reconstitution of lymphoid organs. Finally, the integrin CD18 (lymphocyte function-associated antigen-1, or LFA-1) functions in naïve T cell trafficking between the gut and secondary lymphoid organs43,44 and is implicated in gut autoimmunity.45 Adoptive transfer of CD4+CD18−/− cells into Rag−/− hosts has shown the requirement of CD18 both for fast and slow lymphopenia-induced proliferation.46 The above studies have illustrated the importance of non-cytokine regulators of homeostatic proliferation that skew toward an effector memory phenotype in homeostatic proliferation.

Another potential approach to overcoming homeostatic proliferation as a barrier to transplantation is to delete potentially pathologic CD8+ cells specifically in transplant recipients. Yamada et al employed this approach with the use of anti-CD8 mAbs at the time of lymphodepletion in a mixed chimerism model of MHC mismatched renal transplantation in nonhuman primates; 54 their findings of decreased Tmem responses in CD8-depleted animals are encouraging. The same group subsequently studied alefacept, a fusion protein of the extracellular CD2-binding portion of the human leukocyte function antigen-3 (LFA-3) adhesion molecule.55 This agent is thought to interrupt cytotoxic effector memory T cell proliferation by blocking the interaction between effector-memory CD2+ cells and LFA-3. Alefacept therapy for psoriasis preferentially depleted CD4+CD45RO+ effector memory cells, which correlated with clinical improvement in skin lesions.56 Alefacept preferentially and reversibly depleted CD8+ effector memory (CD28−CD95+) cells in a nonhuman primate transplantation model57; CD28− cells in this model were CD2hi, helping to explain alefacept's ability to preferentially deplete CD8+ cells.

Post-transplant cyclophosphamide administration is an attractive approach to prevent GVHD by depleting alloreactive CD8+ cells that might otherwise survive induction therapy.58,59 Recent data suggest that post-transplant cyclophosphamide administration primarily targets rapidly-dividing allo-specific cells, relatively sparing naïve cells essential to maintenance of immunocompetence following HSCT.60 CD4+Foxp3+Tregs appear resistant to cyclophosphamide and recover quickly following cyclophosphamide induction for allogeneic bone marrow transplantation.61 Sparing of Tregs may partly underlie the mechanism by which cyclophosphamide prevents GVHD.

Thangavelu et al., (2005) demonstrated prolonged, profound CD4+T-lymphopenia in rheumatoid arthritis (RA) patients following lymphocyte-depleting therapy. Poor reconstitution could result either from reduced de novo T-cell production through the thymus or from poor peripheral expansion of residual T-cells. Interleukin-7 (IL-7) is known to stimulate the thymus to produce new T-cells and to allow circulating mature T-cells to expand, thereby playing a critical role in T-cell homeostasis. In the present study we demonstrated reduced levels of circulating IL-7 in a cross-section of RA patients. IL-7 production by bone marrow stromal cell cultures was also compromised in RA. To investigate whether such an IL-7 deficiency could account for the prolonged lymphopenia observed in RA following therapeutic lymphodepletion, we compared RA patients and patients with solid cancers treated with high-dose chemotherapy and autologous progenitor cell rescue. Chemotherapy rendered all patients similarly lymphopenic, but this was sustained in RA patients at 12 months, as compared with the reconstitution that occurred in cancer patients by 3-4 months. Both cohorts produced naive T-cells containing T-cell receptor excision circles. The main distinguishing feature between the groups was a failure to expand peripheral T-cells in RA, particularly memory cells during the first 3 months after treatment. Most importantly, there was no increase in serum IL-7 levels in RA, as compared with a fourfold rise in non-RA control individuals at the time of lymphopenia. Our data therefore suggest that RA patients are relatively IL-7 deficient and that this deficiency is likely to be an important contributing factor to poor early T-cell reconstitution in RA following therapeutic lymphodepletion. Furthermore, in RA patients with stable, well controlled disease, IL-7 levels were positively correlated with the T-cell receptor excision circle content of CD4+ T-cells, demonstrating a direct effect of IL-7 on thymic activity in this cohort.

EXAMPLES

The following examples demonstrate that high dose glucocorticoid receptor agonists can cause near complete lymphodepletion of peripheral blood lymphocytes as well as reduce the number of germinal centers in lymphoid organs and deplete thymus lymphocytes. These effects are achieved without substantially affecting cell counts of neutrophils, platelets, RBCs and stem cells (both HSCs and MSCs).

These examples also show that this lymphodepletion profile of high doses of glucocorticoid agonists is similar to that of standard chemotherapy regimens (based on Cyclophosphamide (Cy) and Fludarabine (Flu)), but does not elicit associated weight loss (a general measure of toxicity of such chemotherapeutic regimens).

High doses of glucocorticoid agonists thus represent a non-myeloablative regimen that can produce "immunologic reset" with efficacy comparable to chemotherapy but without associated toxicity. Accordingly, high dose glucocorticoid receptor agonists represent a promising therapy for use in the treatment of diseases mediated by immune cells such as lymphocytes.

Example 1—Immunosuppressant Reduction of Secondary and Primary Lymphatic Sites

Acute high dose dexamethasone may also be referred to herein as Dex, AugmenStem™, PlenaStem™ or AVM0703.

For mice, male mice were intraperitoneally injected with dexamethasone sodium phosphate for 114.6 mg/kg dexamethasone base (HED 9.32 mg/kg) day 0 and were sacrificed 96 hours after the dexamethasone injection. The mice were sacrificed by exsanguination and then residual blood cells flushed out with 5 U heparin/ml PBS via retrograde flush into the thoracic jugular vein. The spleens were removed, weighed wet, and then fixed in 10% formalin. Subsequently the spleens were sectioned via proprietary methods and then incubated with FITC-PNA at 4 degC for 24 hours, washed, placed on slides and immunofluorescent images were captured. Metamorph software was used to quantify the immunofluorescent signal. Sample images and the results, normalized to spleen area, are shown in FIG. 1.

Control mice have significant FITC-PNA immunofluorescence, while mice who were injected with dexamethasone sodium phosphate have almost no immunofluorescent signal. FITC-PNA labels germinal centers, which non-exclusively relates to the spleen and lymph nodes. This example demonstrates the ability of high dose dexamethasone to reduce the number of germinal centers (GCs) in lymphoid organs, which could eliminate autoreactive immunologic memory. Reducing the number of germinal centers in lymphoid organs can also force cancer cells (for example germinal center lymphomas) or residual HIV infected T cells, which bind to niches in these centers, into the circulation where they can be eliminated by the immune system or standard therapies.

Figure 2:
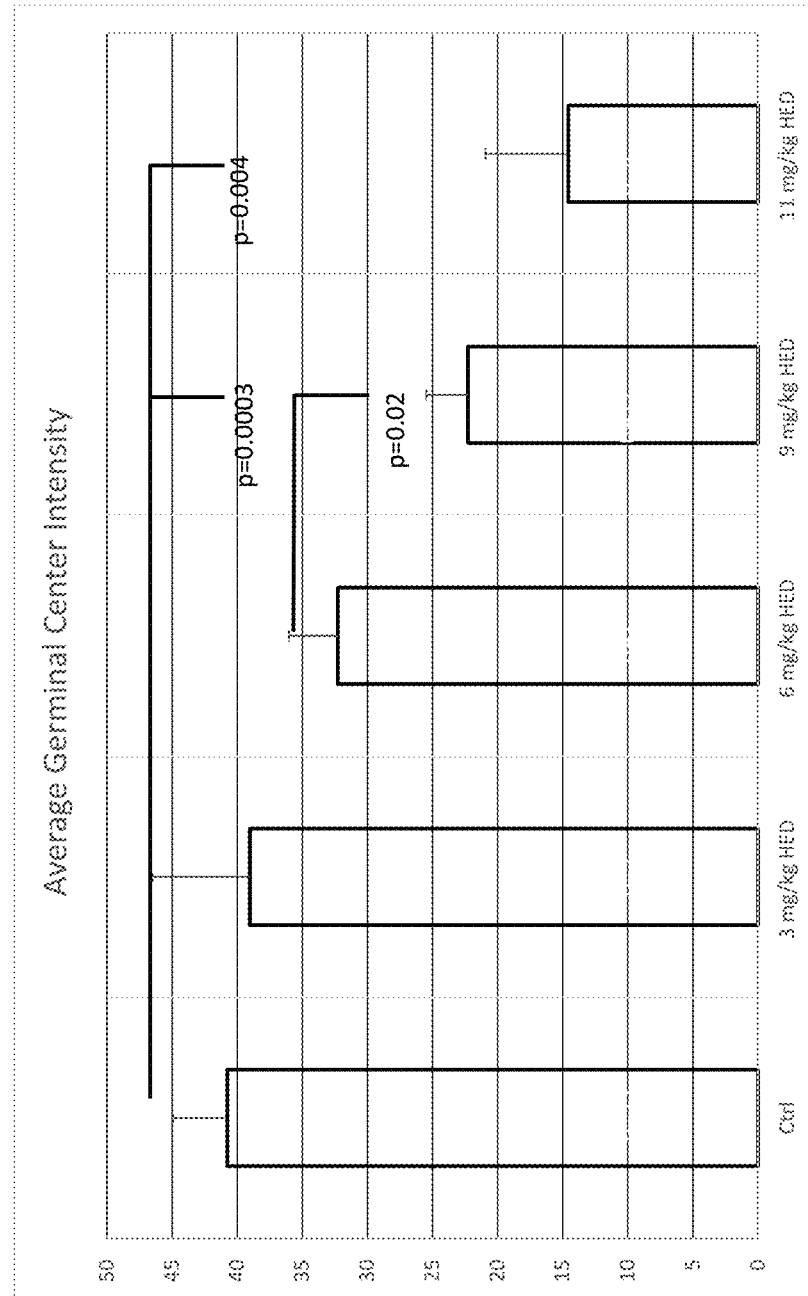
FIG. 2. Acute high dose dexamethasone dose-dependently eliminates binding niches in the mouse spleen. A graph of column plots of average Germinal Center staining intensity measured using immunofluorescent staining of fresh thick spleen sections stained with FITC-PNA is shown. Immunofluorescent intensity was calculated using thresholding and MetaMorph Image Analysis. Columns are average plus SEM. The mice were administered placebo, 3 mg/kg HED, 6 mg/kg HED, 9 mg/kg HED, or 12 mg/kg HED dexamethasone base 48 hours before spleen harvest. Germinal center reduction is apparent at HED 6 mg/kg and is significantly reduced at HED of 9 and 12 mg/kg doses.

FIG. 2 shows the dose response of acute high dose dexamethasone (in HED) effect on germinal center number in spleens of mice. Germinal center reduction is apparent at HED 6 mg/kg but not significantly reduced until HED of 9 and 12 mg/kg doses.

Figure 3:
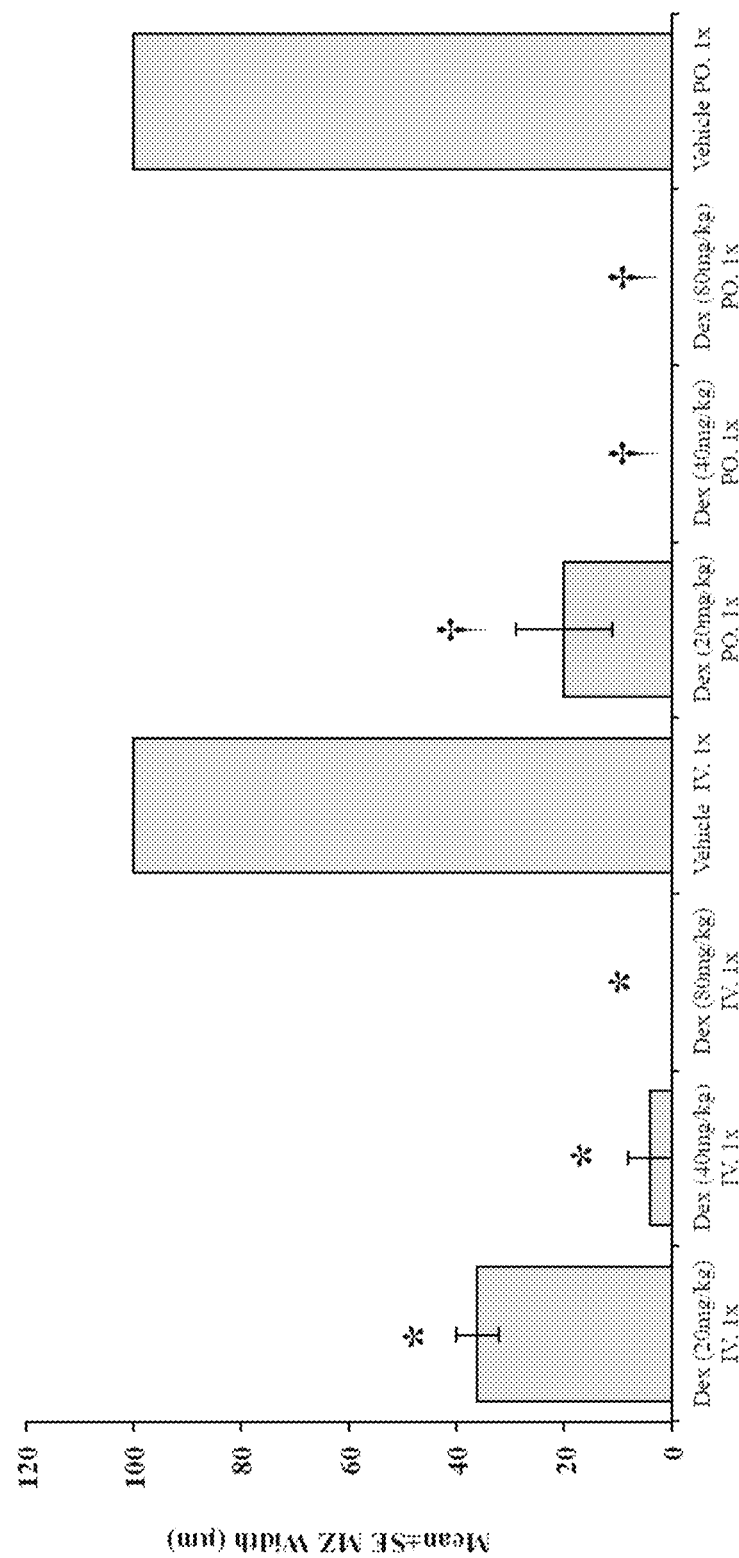
FIG. 3. Acute high dose dexamethasone eliminates binding niches in the rat spleen (MZ: marginal zone). Column plots of marginal zone widths measured on 5 micron spleen sections from rats treated IV or PO with placebo, 20 mg/kg (HED 3.23 mg/kg), 40 mg/kg (HED 6.45 mg/kg) or 80 mg/kg (HED 12.9 mg/kg) dexamethasone base 48 hours before spleen harvest are shown. Marginal zone area was reduced at all dexamethasone doses, and was maximally inhibited at 12.9 mg/kg HED. n=5 per group. * $p<0.05$ ANOVA (Dunnett's post-hoc) vs. Vehicle IV; † $p<0.05$ ANOVA (Dunnett's post-hoc) vs. Vehicle PO; $p<0.05$ Student's t-test vs. Vehicle IV.
Figure 4:
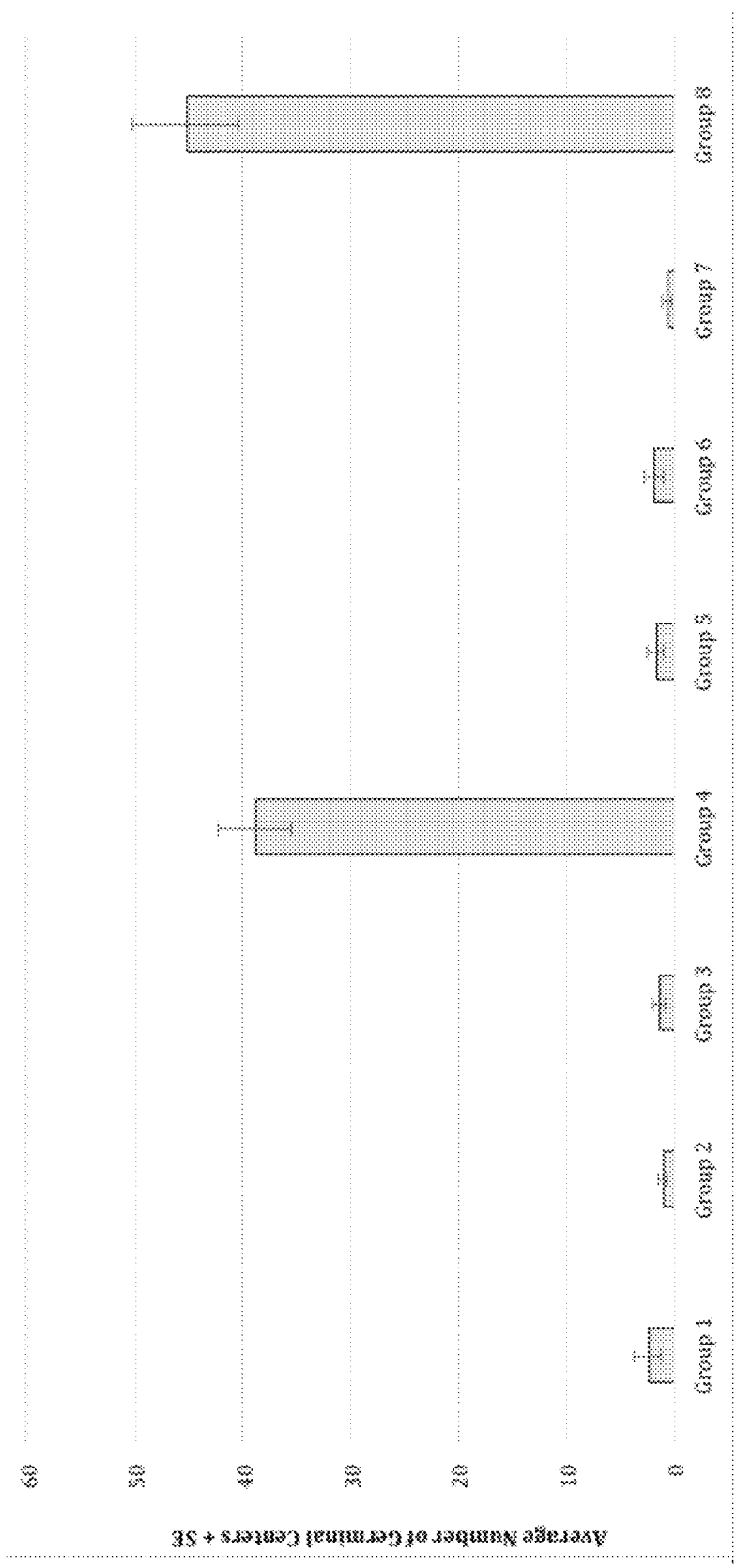
FIG. 4. Acute high dose dexamethasone eliminates binding niches in the rat spleen. Column plots of the area per spleen of BCL-6 staining of 5 micron fixed spleen sections as a measure of germinal center numbers given as average per section are shown. Rats were treated IV or PO with placebo, 20 mg/kg (HED 3.23 mg/kg), 40 mg/kg (HED 6.45) or 80 mg/kg (HED 12.9 mg/kg) dexamethasone base 48 hours before spleen harvest. Germinal center area was reduced at all dexamethasone doses, and was maximally inhibited at 12.9 mg/kg HED. Groups 1-4 IV: 1=20 mg/kg (HED 3.23 mg/kg), 2=40 mg/kg (HED 6.45 mg/kg), 3=80 mg/kg (HED 12.9 mg/kg), 4=Placebo. Groups 5-9 PO: 5=20 mg/kg (HED 3.23 mg/kg), 6=40 mg/kg (HED 6.45 mg/kg), 7=80 mg/kg (HED 12.9 mg/kg), 8=Placebo.

For rat, dexamethasone HED between 3.23, 6.45 and 12.9 mg/kg (rat doses 20, 40 and 80 mg/kg) was administered (IV or PO) to determine GC and marginal zone inhibition 48 hours later. In the rat, the HED Dex dose of 12.9 mg/kg maximally inhibited both GC and marginal zone number and area as shown in FIG. 3 and FIG. 4. Formalin-fixed spleens were cross-sectioned in 5 pieces, trimmed and embedded in paraffin, sectioned and stained with hematoxylin and eosin (H&E). Measurements of the periarteriolar lymphoid sheath (PAL) diameter and the width of the marginal zone (MZ) in areas of white pulp that had PAL with the greatest diameter were measured using an ocular micrometer. BCL-6 immunohistochemical staining in rat spleens was evaluated to determine GC area using automated image analysis methods.

Figure 5:
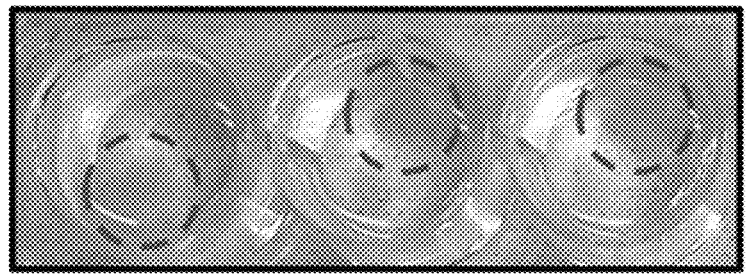
FIG. 5. Acute high dose dexamethasone reduces thymic mass. Photographs show size of thymus from placebo-treated murine subjects (top photograph) and of thymus of murine subjects treated with a 6 mg/kg HED dose of the pharmaceutical composition of the invention (lower photograph). The lower panel shows the thymus weight to body weight percentage of the thymus of placebo-treated subjects (control) and of subjects treated with the pharmaceutical composition of the invention at 3 mg/kg HED, 6 mg/kg HED, 9 mg/kg HED and 12 mg/kg HED.
Figure 5:
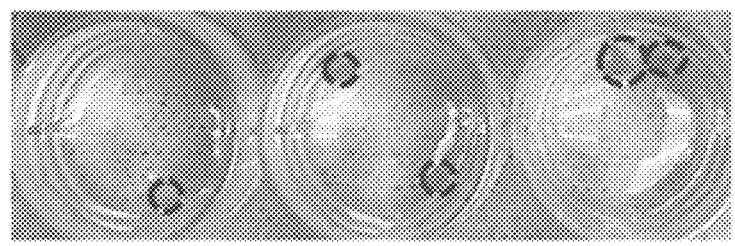
Figure 5:
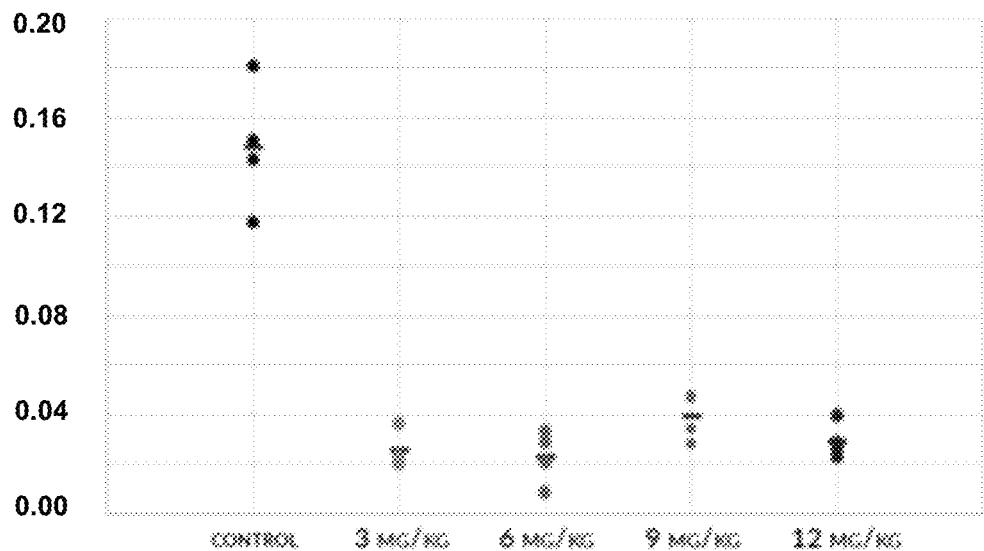

Acute high dose dexamethasone also reduces thymic mass and volume (FIG. 5). For mice, male mice were orally administered vehicle or dexamethasone sodium phosphate for 3, 6, 9 and 12 mg/kg HED dexamethasone base day 0 and were sacrificed 48 hours after the dexamethasone treatment. The mice were sacrificed by exsanguination and then residual blood cells flushed out with 5 U heparin/ml PBS via retrograde flush into the thoracic jugular vein. The thymus from each mouse were removed, weighed wet, graphed as thymus weight/body weight.

Figure 11:
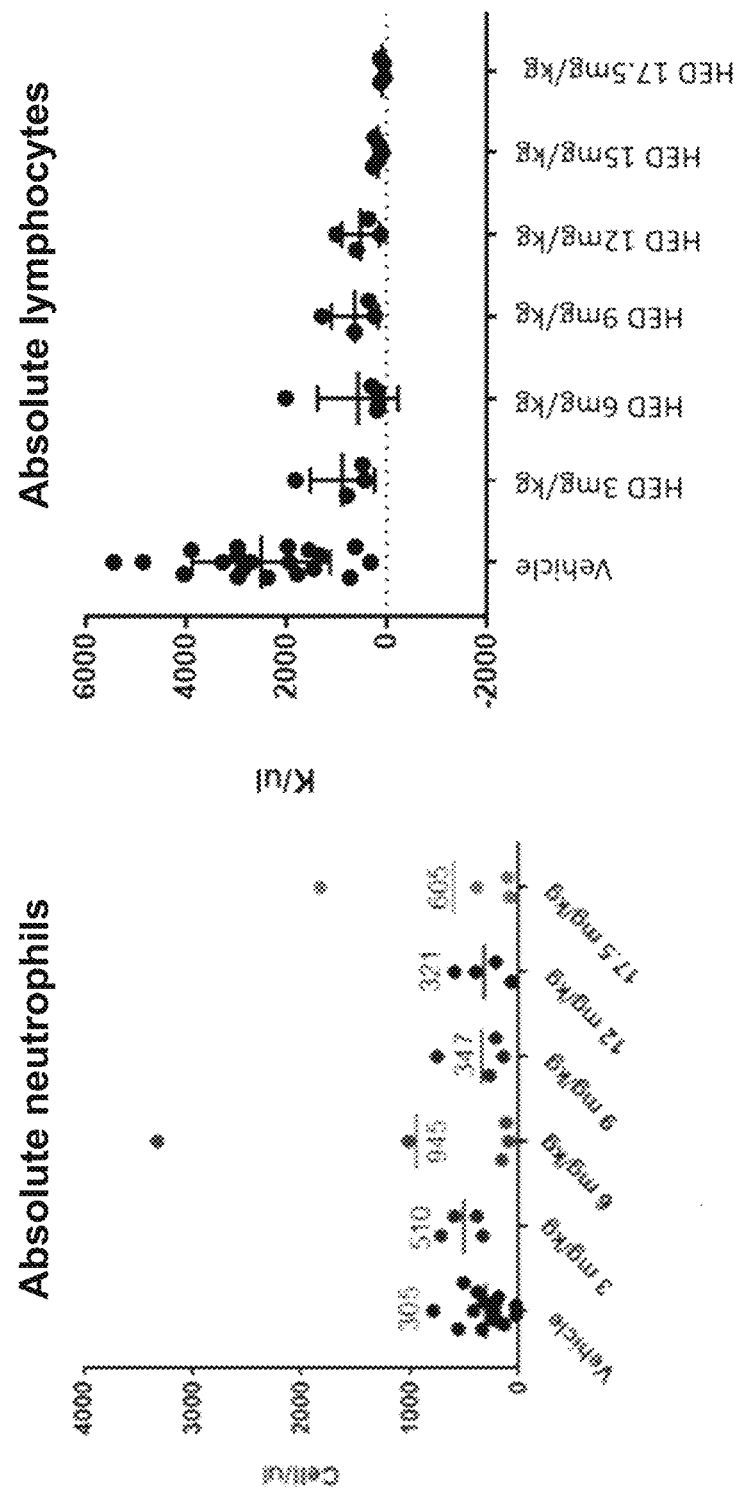
FIG. 11. Acute high dose dexamethasone reduces mouse absolute lymphocyte numbers while sparing neutrophils. Graphs of individual absolute neutrophils (left) and total lymphocytes (right) and averages measured by complete blood counts 24-48 hours after mice were treated PO with placebo, HED 3 mg/kg, HED 6 mg/kg, HED 9 mg/kg, HED 12.mg/kg, or HED 17.5 mg/kg dexamethasone base are shown. Cells/ul=absolute numbers obtained from complete blood counts (CBC). Acute high dose dexamethasone causes almost complete lymphoabalation at HED doses greater than 12 mg/kg, but does not affect neutrophils. Acute high dose dexamethasone therefore eliminates the need for transfusion, and provides a safer, non-toxic alternative to chemotherapeutic regimens. Doses are shown as HED (human equivalent dose).

Example 2—Immunosuppressant Lymphodepletion in Mice and Rats 24-48 Hours after Acute Administration of Dexamethasone, with Neutrophil, RBC, Platelet and Stem Cell Sparing Properties Preliminary dose escalation studies performed in naïve mouse and rat models showed that administration of high-dose dexamethasone results in complete lymphodepletion (FIG. 11, right side). High-doses of dexamethasone were able to induce ~98% reduction in CD4+, CD8+, Tregs and B cells population measured 48 hours after administration, supporting rapid ablation of autoimmune pathophysiologic substrates. Early stage validation showed that acute high dose dexamethasone has 2-3 hour half-life by pharmacokinetic and a pharmacodynamics half-life of 4-5 days, which exclude prolonged immune suppression. In addition, oral dosing of acute high dose dexamethasone has comparable effects to IV dosing, which supports the use of acute high dose dexamethasone as a single oral treatment.

Figure 6:
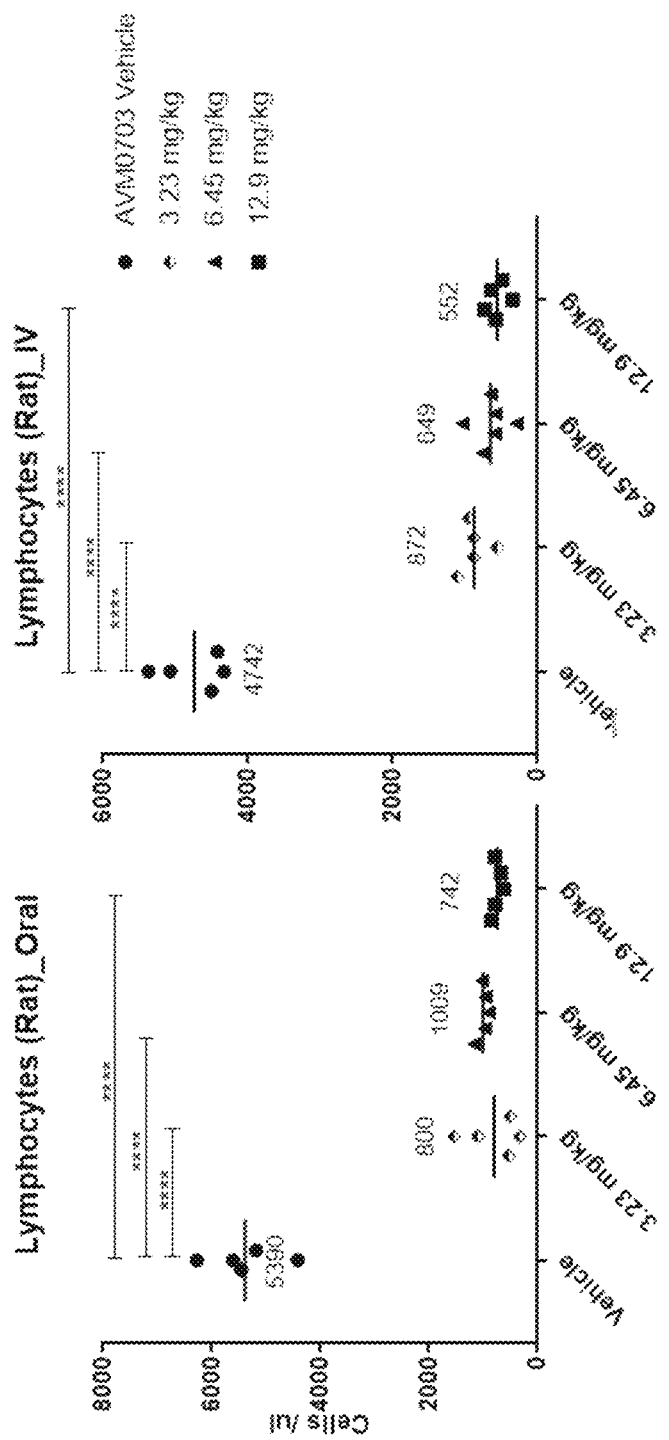
FIG. 6. Acute high dose dexamethasone reduces rat lymphocyte number. Graphs of individual absolute lymphocyte numbers and averages measured by complete blood count 48 hours after rats were treated IV (right) or PO (left) with placebo, 20 mg/kg (HED 3.23 mg/kg), 40 mg/kg (HED 6.45) or 80 mg/kg (HED 12.9 mg/kg) dexamethasone base are shown. Dexamethasone was administered 48 hours before blood withdrawal. Significant lymphodepletion was observed at all doses vs. controls in rats whether IV (right) or oral dosing (left). Doses are shown as HED (human equivalent dose).
Figure 7:
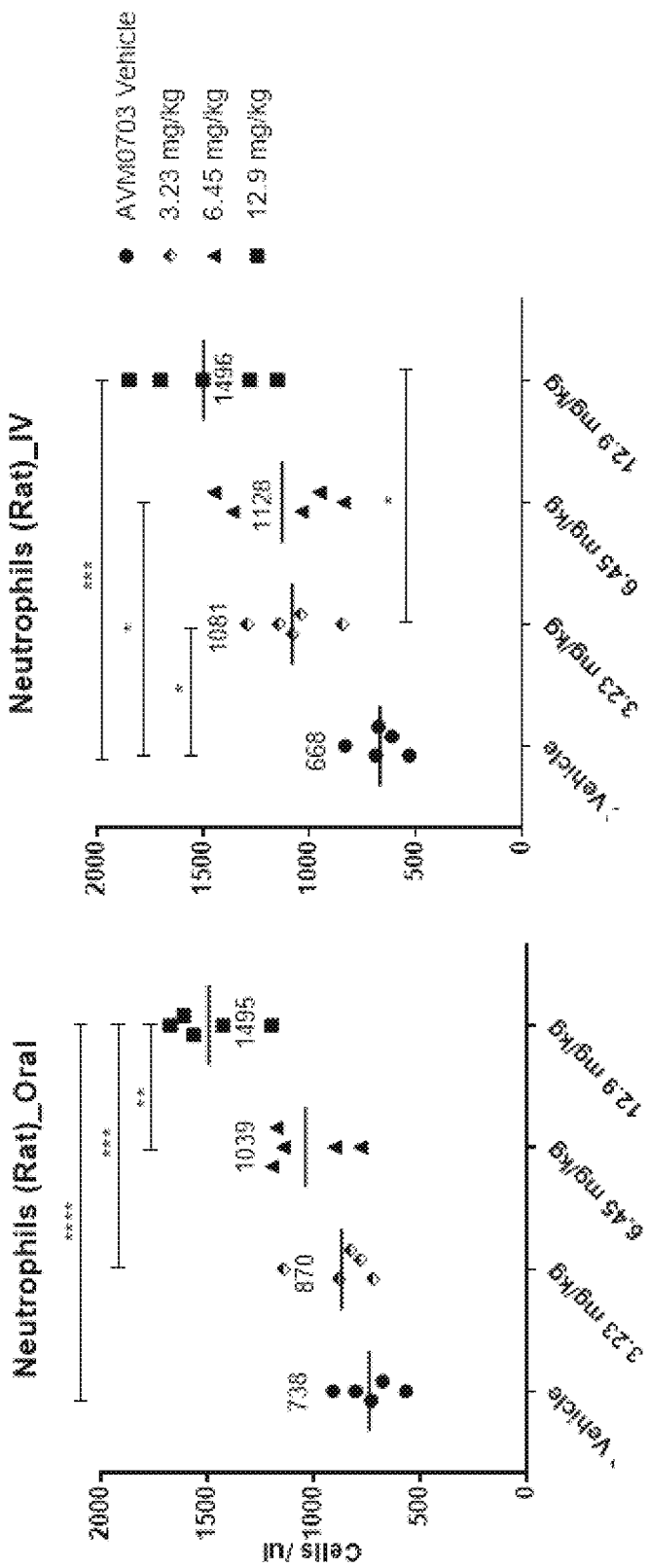
FIG. 7. Acute high dose dexamethasone does not reduce rat neutrophil number. Graphs of individual absolute neutrophil numbers and averages measured by complete blood count 48 hours after rats were treated IV (right) or PO (left) with placebo, 20 mg/kg (HED 3.23 mg/kg), 40 mg/kg (HED 6.45) or 80 mg/kg (HED 12.9 mg/kg) dexamethasone base are shown. Data in FIGS. 3, 4, and 6 are from the same rats. Acute high dose dexamethasone has a lymphodepletion profile that is neutrophil sparing. Oral (left) and IV (right) doses were administered 1×48 hours before blood withdrawal. Doses are shown as HED (human equivalent dose).

As shown in FIG. 6, IV or PO administration of dexamethasone at 20 (3.2 HED), 40 (6.5 HED) or 80 (12.9 HED) mg/kg to male Lewis rats weighing 250-300 grams significantly reduced lymphocyte count at all doses compared to Placebo 48 hours after administration. In contrast, as shown in FIG. 7, neutrophils were not reduced by acute high dose dexamethasone. Neutrophil number are actually increased by all doses of dexamethasone, likely via a demargination effect. RBCs, platelets, Hct, HgB were not affected by the dexamethasone treatment.

Figure 8:
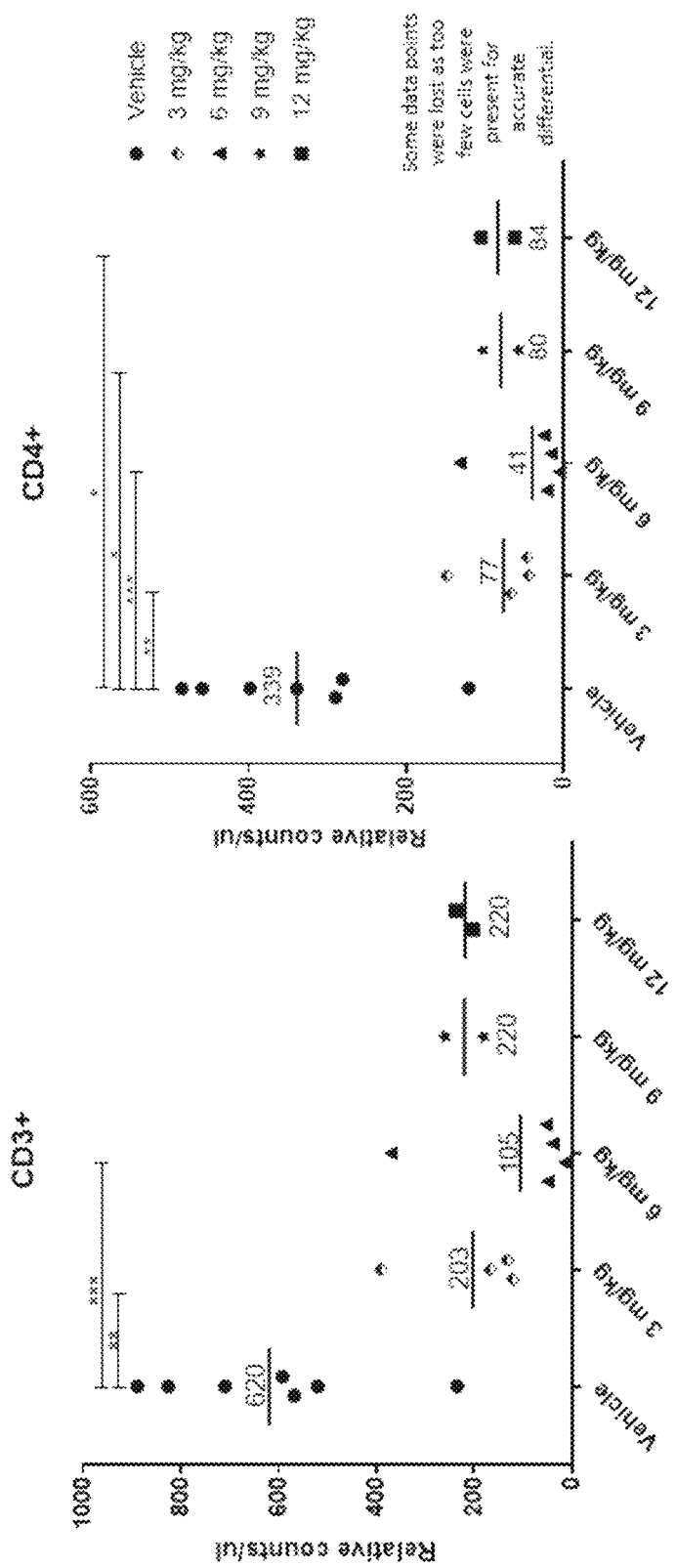
FIG. 8. CD3 and CD4 positive lymphocytes. Graphs of individual CD3+(left) and CD4+(right) lymphocytes and averages measured by flow cytometry as relative counts and normalized to relative absolute counts using complete blood counts 48 hours after mice were treated PO with placebo, HED 3 mg/kg, HED 6 mg/kg, HED 9 mg/kg or HED 12.mg/kg dexamethasone base. Relative counts/ul=flow cytometry and complete blood count combined. Compared to control, in the 12 mg/kg group: 65% reduction in CD3+ cells; 75% reduction in CD4+ cells. Doses are shown as HED (human equivalent dose). A one-way ANOVA followed by Tukey's test was incorporated to determine statistical significance between the treatment groups; * p<0.05,  p<0.01, * p<0.001.
Figure 9:
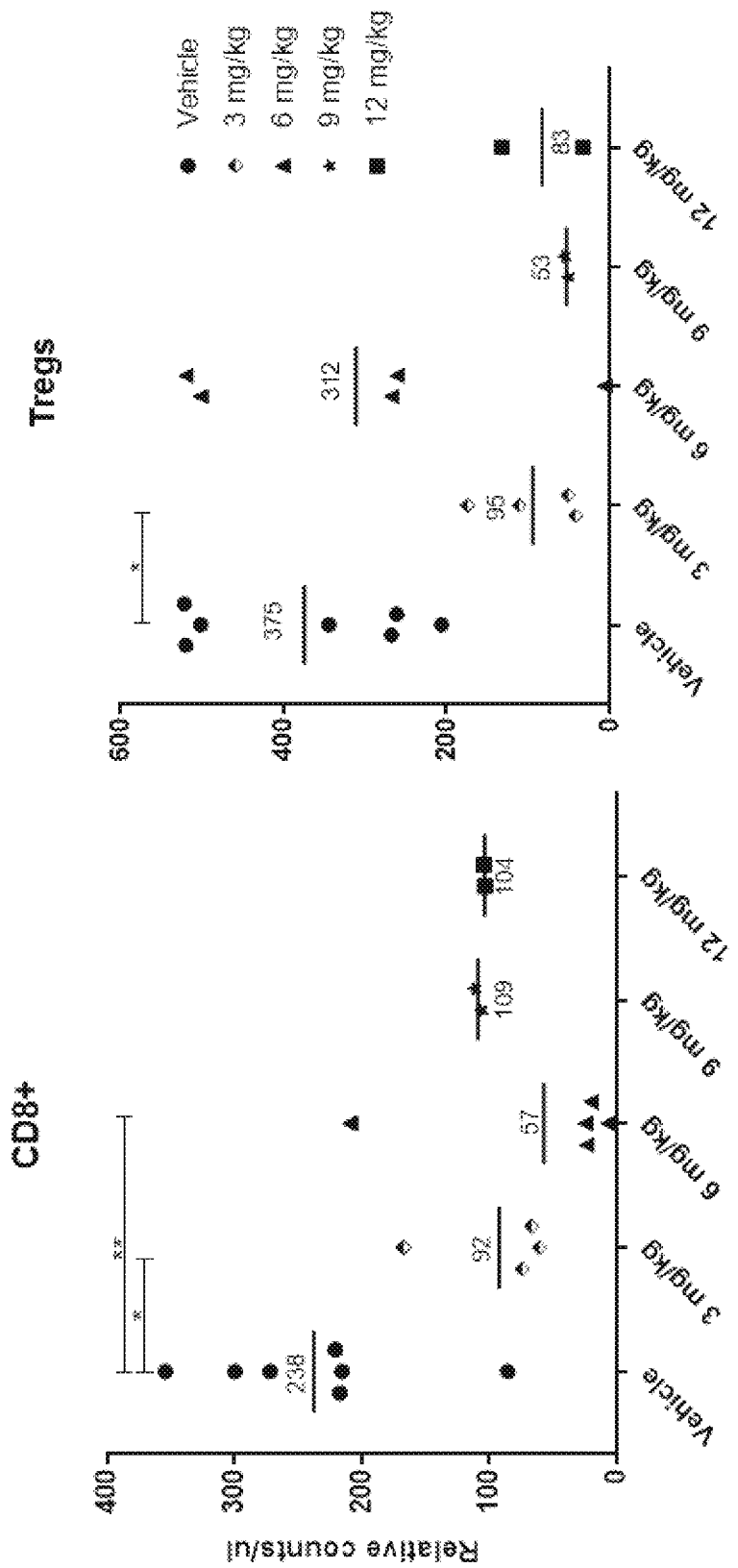
FIG. 9. Acute high dose dexamethasone reduces mouse CD8 positive lymphocytes and Tregs. Graphs of individual CD8+(left) and Treg (right) lymphocytes and averages measured by flow cytometry as relative counts and normalized to relative absolute counts using complete blood counts 48 hours after mice were treated PO with placebo, HED 3 mg/kg, HED 6 mg/kg, HED 9 mg/kg or HED 12.mg/kg dexamethasone base are shown. Treg lymphocytes were identified by being CD3+CD4+CD25+FoxP3+. Relative counts/ul=flow cytometry and complete blood counts combined. Compared to control, in the 12 mg/kg group: 56% reduction in CD8+ cells; 78% reduction in mouse Tregs. Doses are shown as HED (human equivalent dose). A one-way ANOVA followed by post-hoc Tukey's test was incorporated to determine statistical significance between the treatment groups; * p<0.05, ** p<0.01.
Figure 10:
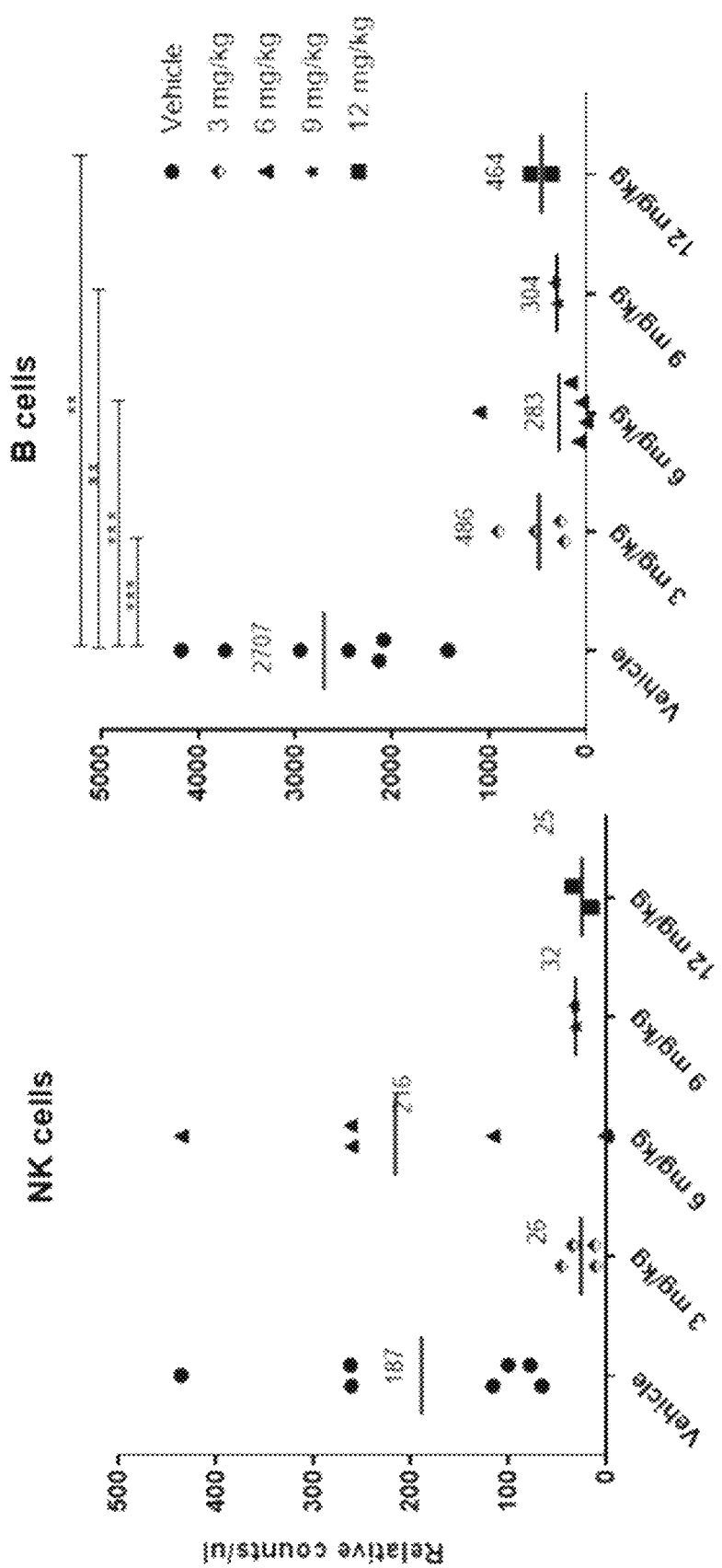
FIG. 10. Acute high dose dexamethasone reduces mouse NK cells and B lymphocytes. Graphs of individual natural killer (NK) cells (left) and B lymphocytes (right) and averages measured by flow cytometry as relative counts and normalized to relative absolute counts using complete blood counts 48 hours after mice were treated PO with placebo, HED 3 mg/kg, HED 6 mg/kg, HED 9 mg/kg or HED 12.mg/kg dexamethasone base are shown. NK cells were identified by being CD3−CD49b+. B lymphocytes were identified by being CD3-B220+. Relative counts/ul=flow cytometry and complete blood counts combined. Compared to control, in the 12 mg/kg group: 87% reduction in NK cells; 83% reduction B cells. Doses are shown as HED (human equivalent dose). A one-way ANOVA followed by post-hoc Tukey's test was incorporated to determine statistical significance between the treatment groups; * p<0.05,  p<0.01; * p<0.001.
Figure 12:
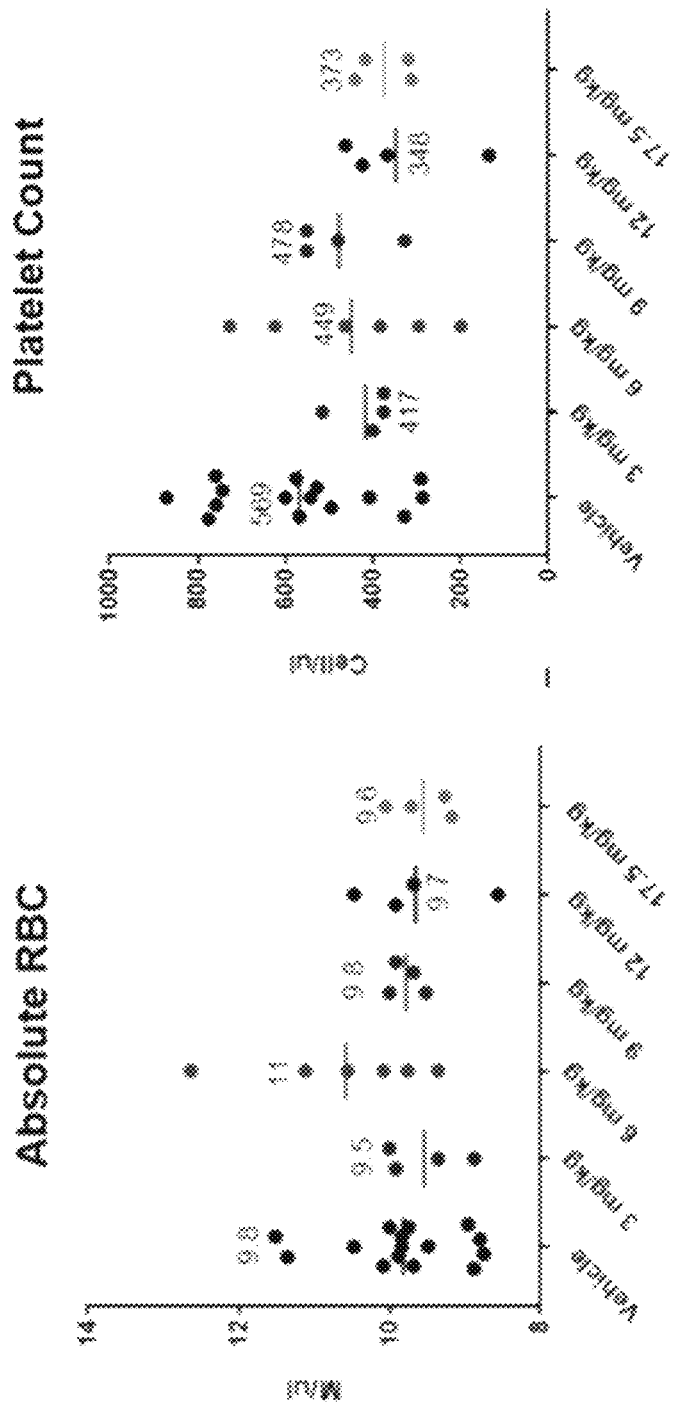
FIG. 12. Acute high dose dexamethasone spares mouse RBCs and Platelets. Graphs of individual absolute RBC (left) and platelet (right) and averages measured by complete blood counts 48 hours after mice were treated PO with placebo, HED 3 mg/kg, HED 6 mg/kg, HED 9 mg/kg, HED 12.mg/kg, or 17.5 mg/kg dexamethasone base are shown. Cells/ul=absolute numbers obtained from CBC. Acute high dose dexamethasone does not affect RBCs or platelets, eliminates the need for transfusion, and therefore provides a safer, non-toxic alternative to chemotherapeutic regimens. Doses are shown as HED (human equivalent dose).
Figure 13:
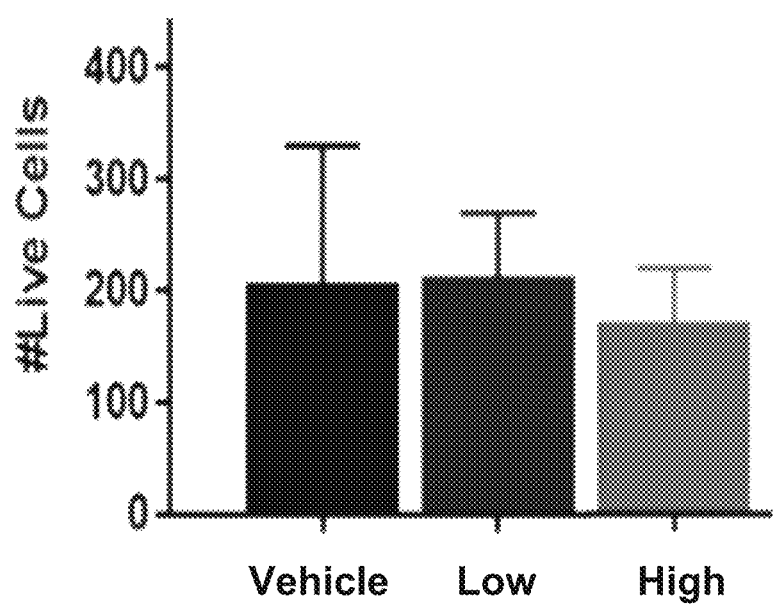
FIG. 13. Number of live hematopoietic stem cells measured 48 hours after treatment of naïve mice with placebo (vehicle), or low or high doses of acute high dose dexamethasone are shown. Even high doses of acute high dose dexamethasone did not significantly alter the number of live hematopoietic stem cells. The non-myeloablative regimen represented by acute high dose dexamethasone could, therefore, eliminate the need for transfusions of stem cells for hematopoietic recovery after immune-reset.

Oral acute administration of dexamethasone to C57B1 male mice at HED of 3 mg/kg (n=4), HED 6 mg/kg (n=6), 9 mg/kg (n=4), 12 mg/kg (n=4), 15 mg/kg (n=4) or 17.5 mg/kg (n=4) compared to placebo (n=7) reduced CD3+T lymphocytes by 65% and CD4+T lymphocytes by 75% (FIG. 8), reduced CD8+T lymphocytes by 56% and Tregs by 78% (FIG. 9), reduced natural killer cells (NK) by 87% and B lymphocytes by 83% (FIG. 10), reduced absolute lymphocyte count by 84% but spared neutrophils (FIG. 11), RBCs (FIG. 12) and platelets (FIG. 13). Blood was drawn for complete blood chemistry (CBC) and flow cytometry 24 to 48 hours after dexamethasone administration by oral gavage. At HED doses greater than 12 mg/kg almost complete lymphoabalation was observed in normal mice. In tumor bearing mice a near complete lymphoablating dose will be HED greater than 6 mg/kg.

Acute high dose dexamethasone activates receptor-mediated apoptosis via the caspase pathway and lympho-depletes or lympho-ablates all lymphocytes depending on the dose used. As expected from its receptor-mediated mode of action, dexamethasone induces lymphodepletion sparing neutrophils, platelets, and Red Blood Cells (RBCs) due to the lack of or due to different glucocorticoid receptors on these cells. A tendency to elevate neutrophil counts above placebo in both peripheral blood and bone marrow was observed with high doses of dexamethasone, supporting possible protection against infections during lymphodepletion treatments.

Remarkably, high doses of dexamethasone did not significantly alter the amount of hematopoietic stem cells in mice (FIG. 13). The non-myeloablative regimen represented by acute high dose dexamethasone could, therefore, eliminate the need for transfusions of stem cells for hematopoietic recovery after immune-reset.

Figure 15:
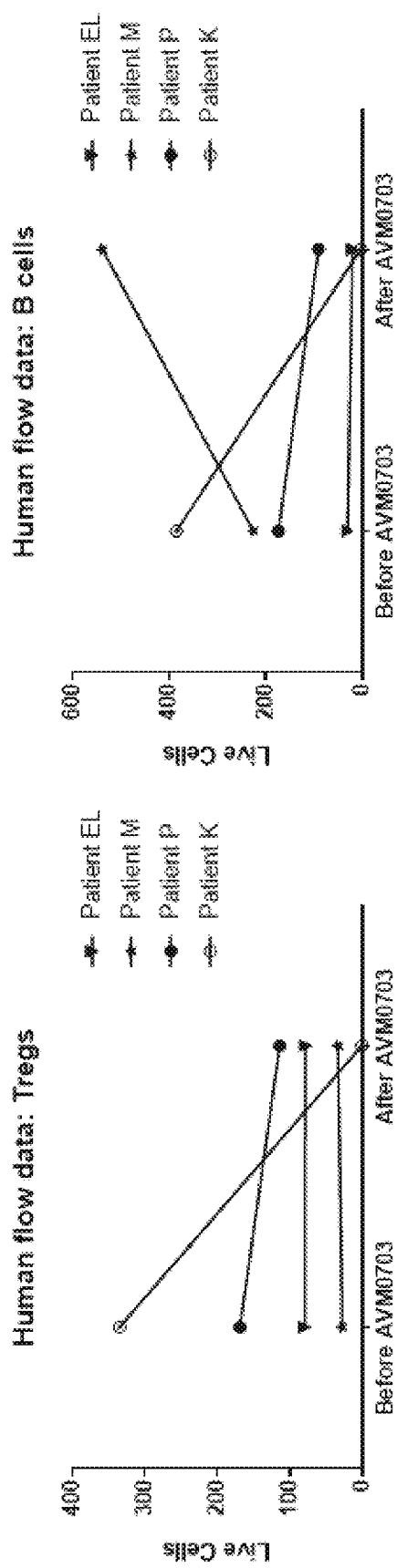
FIG. 15. Twenty-five percent (1 of 4) of human patients treated with 3 mg/kg dexamethasone base depleted Tregs and B lymphocytes. Line are individual pre- and post-, 48 hours after oral administration of 3 mg/kg dexamethasone base to four human patients, values and line plots of Treg and B lymphocytes measured by flow cytometry. Each patient's pre-treatment values are connected to post-treatment values by a connecting line. Tregs are identified by being CD3+CD4+CD25+FoxP3+. B lymphocytes are identified by being CD3−CD19+.
Figure 16:
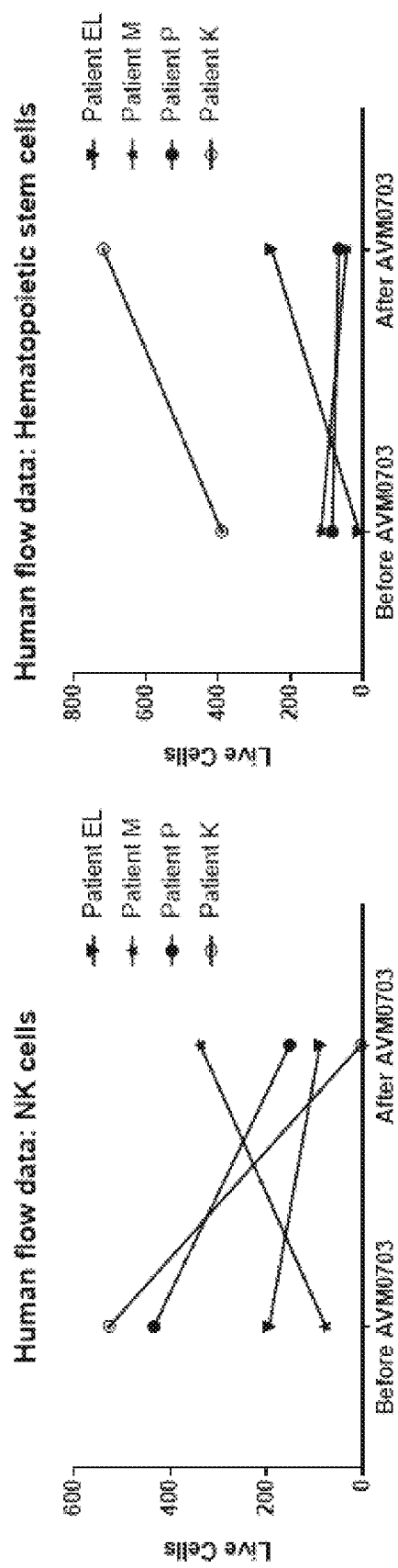
FIG. 16. Seventy-five percent (3 of 4) of human patients treated with 3 mg/kg dexamethasone base depleted NK cells while hematopoietic stem cells were spared. Line are individual pre- and post-treatment, 48 hours after oral administration of 3 mg/kg dexamethasone base to four human patients, values and line plots of NK cells and Hematopoietic Stem Cells (HSCs) measured by flow cytometry. Each patient's pre-treatment values are connected to post-treatment values by a connecting line. NK cells are identified by being CD3−CD16/56+. HSCs are identified by being CD34+CD38−.

Example 3—Immunosuppressant Lymphodepletion in Humans 36-48 Hours after Acute Administration of Dexamethasone, with Neutrophil, RBC, Platelet and Stem Cell Sparing Properties Oral acute administration of 3 mg/kg dexamethasone base equivalent (all doses given are dexamethasone base equivalent in these examples) to four human patients, three with knee osteoarthritis and one with aortic aneurysm, was administered. Blood was drawn before drug treatment and 48 hours post-treatment for CBC analysis and flow cytometry to determine lymphocyte and other blood cell populations. Serum was analyzed for cytokine levels. For one patient, pre-treatment CBCs were not drawn and thus normalized flow cytometry data is shown for only 3 patients. By un-normalized flow cytometry data only 2 of the 4 patients responded to the dexamethasone with lymphodepletion (FIGS. 14, 15, and 16), while 2 of 4 patients showed a lymphocytosis response in CD3 and CD4 lymphocytes and 1 of 4 patients showed a lymphocytosis response in CD8, B lymphocytes and NK cells, to this dose of dexamethasone. 3 of 4 patients showed elevated levels of IL-2 and 4 of 4 showed elevated levels of IL-15 48 hours after acute oral dexamethasone base (3 mg/kg) (FIG. 17). IL-6, a cytokine known to be the primary driver of potentially fatal cytokine release syndrome (CRS) was not elevated in any patient. Based on the lymphocytosis response observed in 2 of 4 non cancer patients at the 3 mg/kg dose, preferred lymphodepleting doses will be 3 mg/kg or higher based on the increased sensitivity of tumor bearing mice to dexamethasone where the lowest lethal dose was HED 43 mg/kg in tumor bearing mice compared to HED 114 mg/kg in healthy mice (Scorza Barcellona, 1984).

Figure 18:
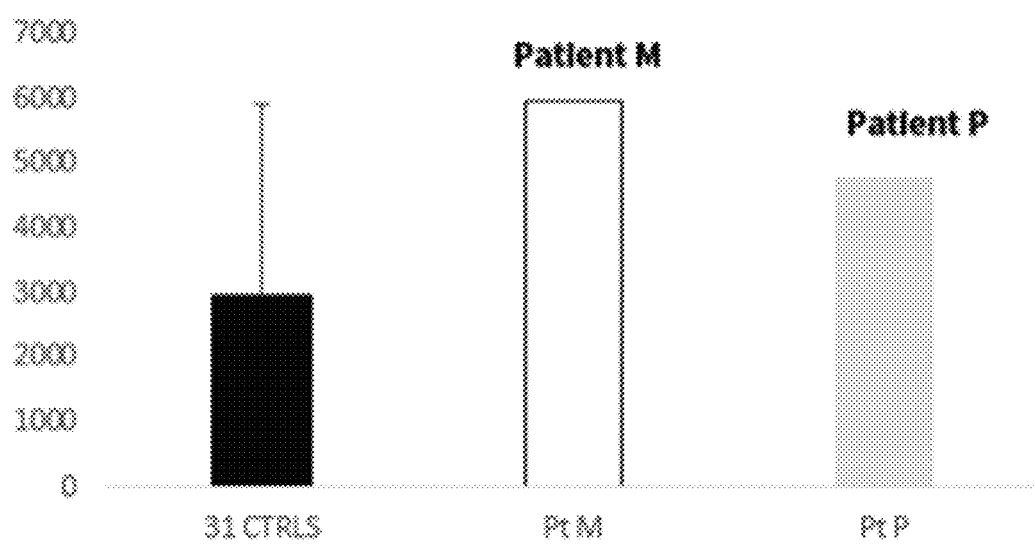
FIG. 18. Oral administration of 3 mg/kg dexamethasone base increased bone marrow MSC number 48 hours later. Column plots of data from 31 historical naïve control humans plus standard deviation, and two human patients treated with 3 mg/kg dexamethasone base 48 hours before aspiration of concentrated bone marrow from the ileac crest using a MarrowCellution™ needle. Plots show bone marrow CFU/ml+/− stdev. Bone marrow was added directly to colony forming unit assay fibroblast (CFU-F) media without further manipulation 24 hours after harvest and shipment at controlled room temperature. CFU-F colony number is a measure of mesenchymal stem cell (MSC) number in the starting material. 48 hours after oral administration of 3 mg/kg dexamethasone base, ileac crest bone marrow MSC numbers appear about twice as high as 31 historical controls. 3 mg/kg oral dexamethasone base increases human bone marrow CFU-F per ml 48 hours later compared to 31 historical controls aspirated using the same MarrowCellution™ needle as for patients M and P.
Figure 19:
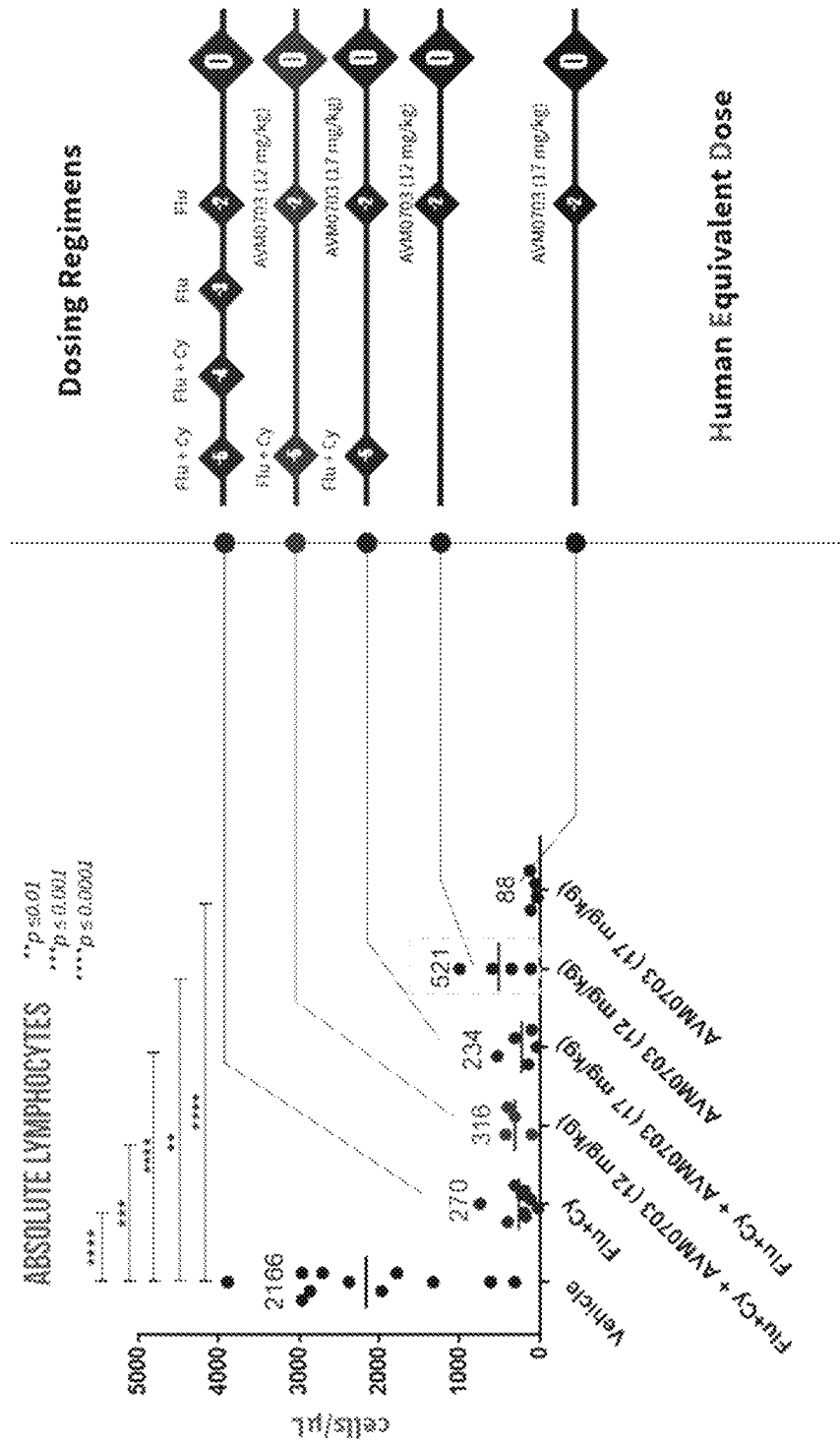
FIG. 19. Comparison of a 12 mg/kg and 17-18 mg/kg dexamethasone base oral dose on day −2 to a single dose of Cyclophosphamide 166 mg/kg (HED 500 mg/m2) and Fludarabine 10 mg/kg on day −5 combined with 12 mg/kg or 17-18 mg/kg dexamethasone base on day −2, and to 2 days of repeat Cyclophosphamide 166 mg/kg on day −5 and −4 and 4 days of Fludarabine 10 mg/kg (HED 30 mg/m2) on days −5, −4, −3, −2. Shown is a graph of individual absolute lymphocytes and averages (left) measured by complete blood counts 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)). Also shown (right) is a representation of the dosing schedules in mice of these regimens.
Figure 20:
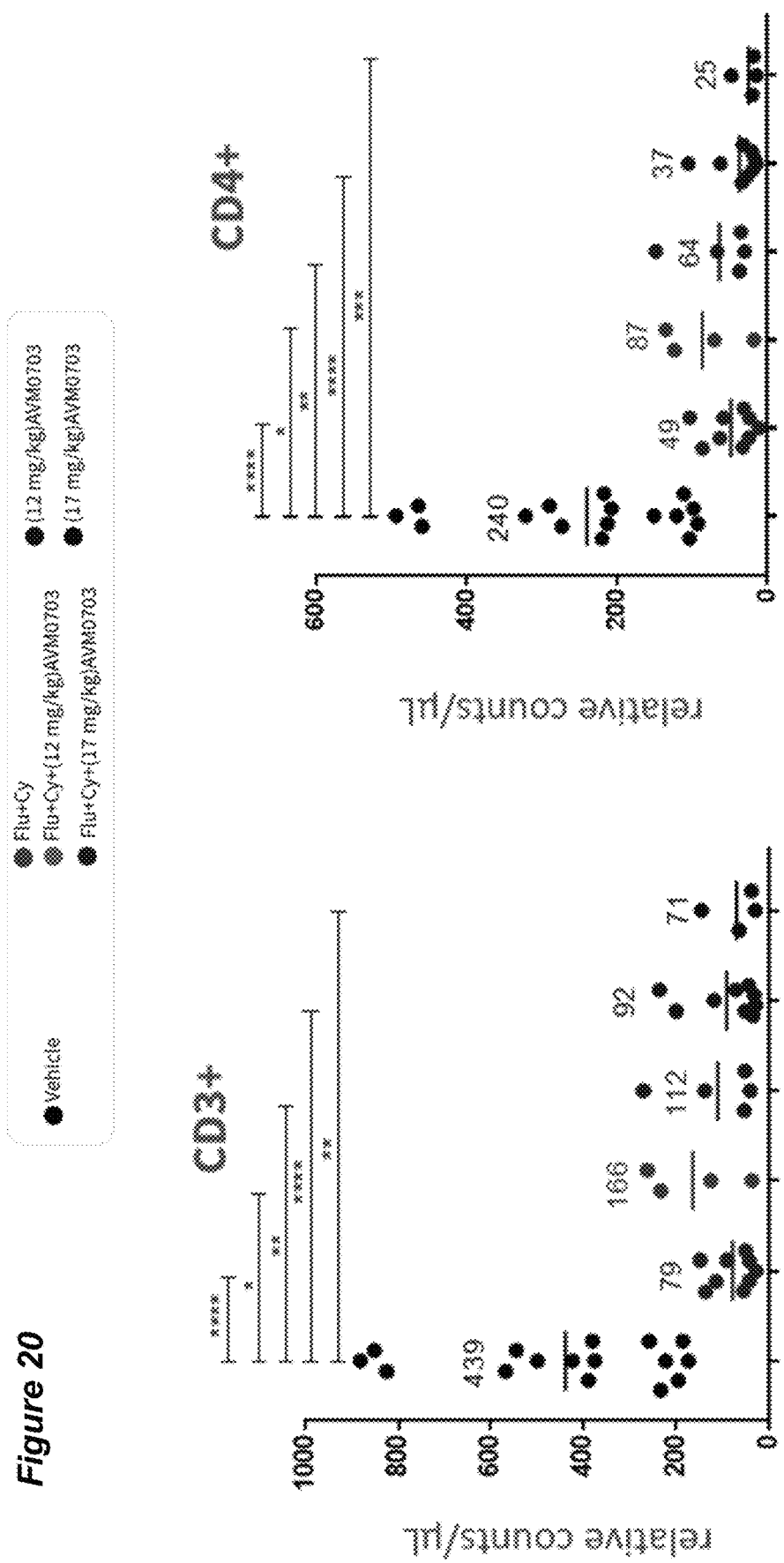
FIG. 20. A single dose of Cyclophosphamide 166 mg/kg (HED 500 mg/m2) and Fludarabine 10 mg/kg on day −5 combined with 12 mg/kg or 17-18 mg/kg dexamethasone base on day −2 equivalently lymphodepleted CD3+ and CD4+ lymphocytes compared to 2 days of repeat Cyclophosphamide 166 mg/kg on day −5 and −4 and 4 days of Fludarabine 10 mg/kg (HED 30 mg/m2) on days −5, −4, −3, −2. Shown are graphs of individual CD3+(left) and CD4+ (right) lymphocytes and averages measured by flow cytometry as relative counts and normalized to relative absolute counts using complete blood counts 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)). On both the CD3+ plot (left) and the CD4+ plot (right), the 12 mg/kg or 17-18 mg/kg dexamethasone base data are shown in the right-hand columns of each (relative counts are '92', '71', '37' and '25').
Figure 21:
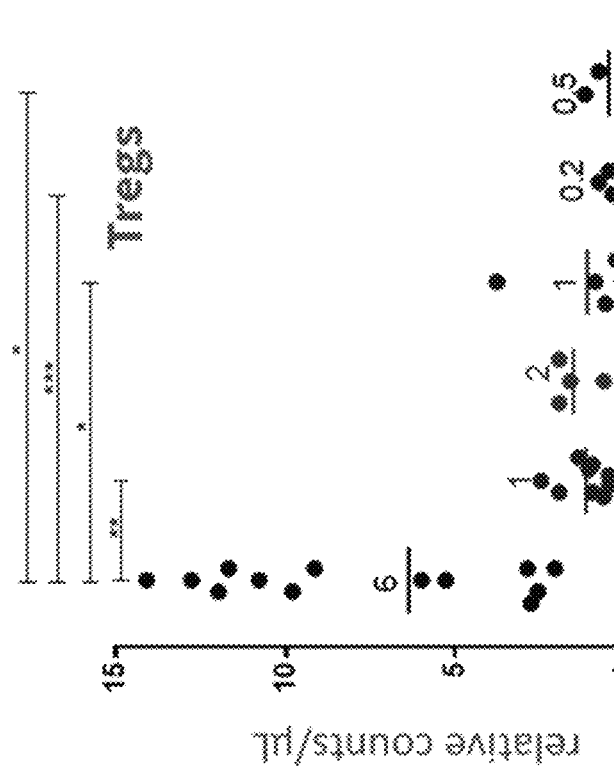
FIG. 21. A single dose of Cyclophosphamide 166 mg/kg (HED 500 mg/m2) and Fludarabine 10 mg/kg on day −5 combined with 12 mg/kg or 17-18 mg/kg dexamethasone base on day −2 equivalently lymphodepleted CD8+ lymphocytes and Tregs compared to 2 days of repeat Cyclophosphamide 166 mg/kg on day −5 and −4 and 4 days of Fludarabine 10 mg/kg (HED 30 mg/m2) on days −5, −4, −3, −2. Shown are graphs of individual Treg (right) and CD8+ lymphocytes (left) and averages measured by flow cytometry as relative counts and normalized to relative absolute counts using complete blood counts 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)). On both the CD8+ plot (left) and the CD4+ plot (right), the 12 mg/kg or 17-18 mg/kg dexamethasone base data are shown in the right-hand columns of each (relative counts are '33', '1.4', '0.2' and '0.5').
Figure 21:
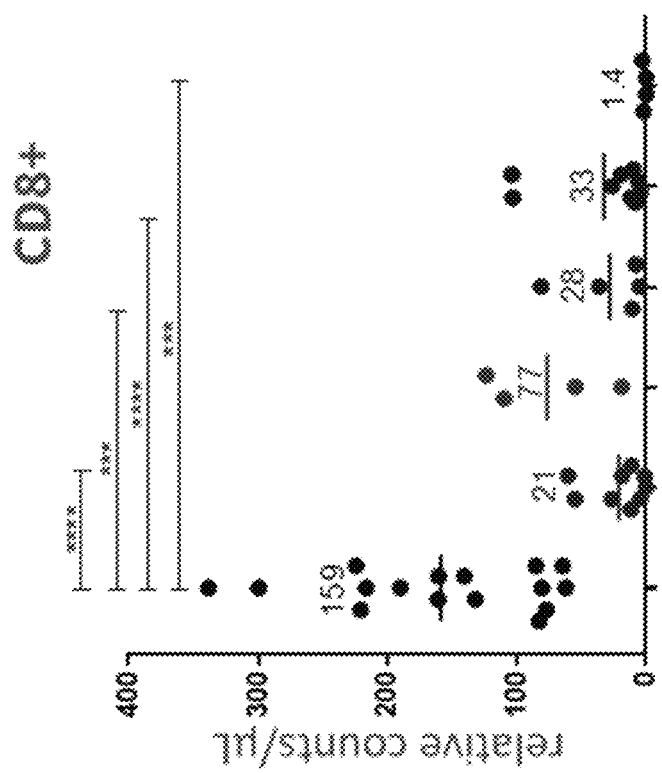
Figure 22:
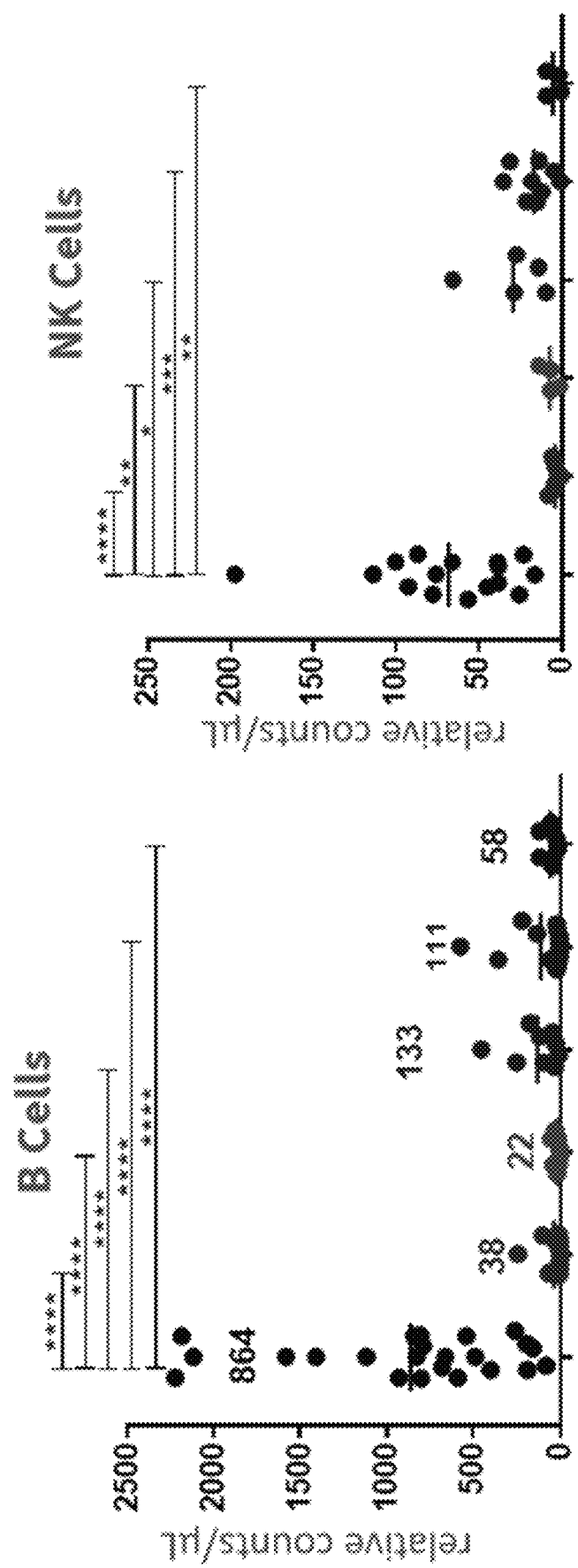
FIG. 22. A single dose of Cyclophosphamide 166 mg/kg (HED 500 mg/m2) and Fludarabine 10 mg/kg on day −5 combined with 12 mg/kg or 17-18 mg/kg dexamethasone base on day −2 equivalently lymphodepleted NK cells and B lymphocytes compared to 2 days of repeat Cyclophosphamide 166 mg/kg on day −5 and −4 and 4 days of Fludarabine 10 mg/kg (HED 30 mg/m2) on days −5, −4, −3, −2. Shown are graphs of individual B lymphocytes (left) and NK cell lymphocytes (right) and averages measured by flow cytometry as relative counts and normalized to relative absolute counts using complete blood counts 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)). On both the B cell plot (left) and the NK cell plot (right), the 12 mg/kg or 17-18 mg/kg dexamethasone base data are shown in the right-hand columns of each (relative counts are '111' and '58' for B cells; not shown for NK cells).

Bone marrow was drawn 48 hours after dexamethasone administration and mesenchymal stem cell (MSC) number was determined by colony-forming assay fibroblast (CFU-F). Oral administration of dexamethasone base 3 mg/kg increased ileac crest bone marrow (BM) MSC almost two fold (FIG. 18). Trilineage differentiation capacity of the BM MSC was also determined in a study in horses. A 6 mg/kg HED doubled sternal BM MSC stem cell number 48 hours after a one hour IV infusion administration to horses, but did not alter trilineage differentiation capacity of the MSC towards osteocytes, chondrocytes or adipocytes.

Figure 25:
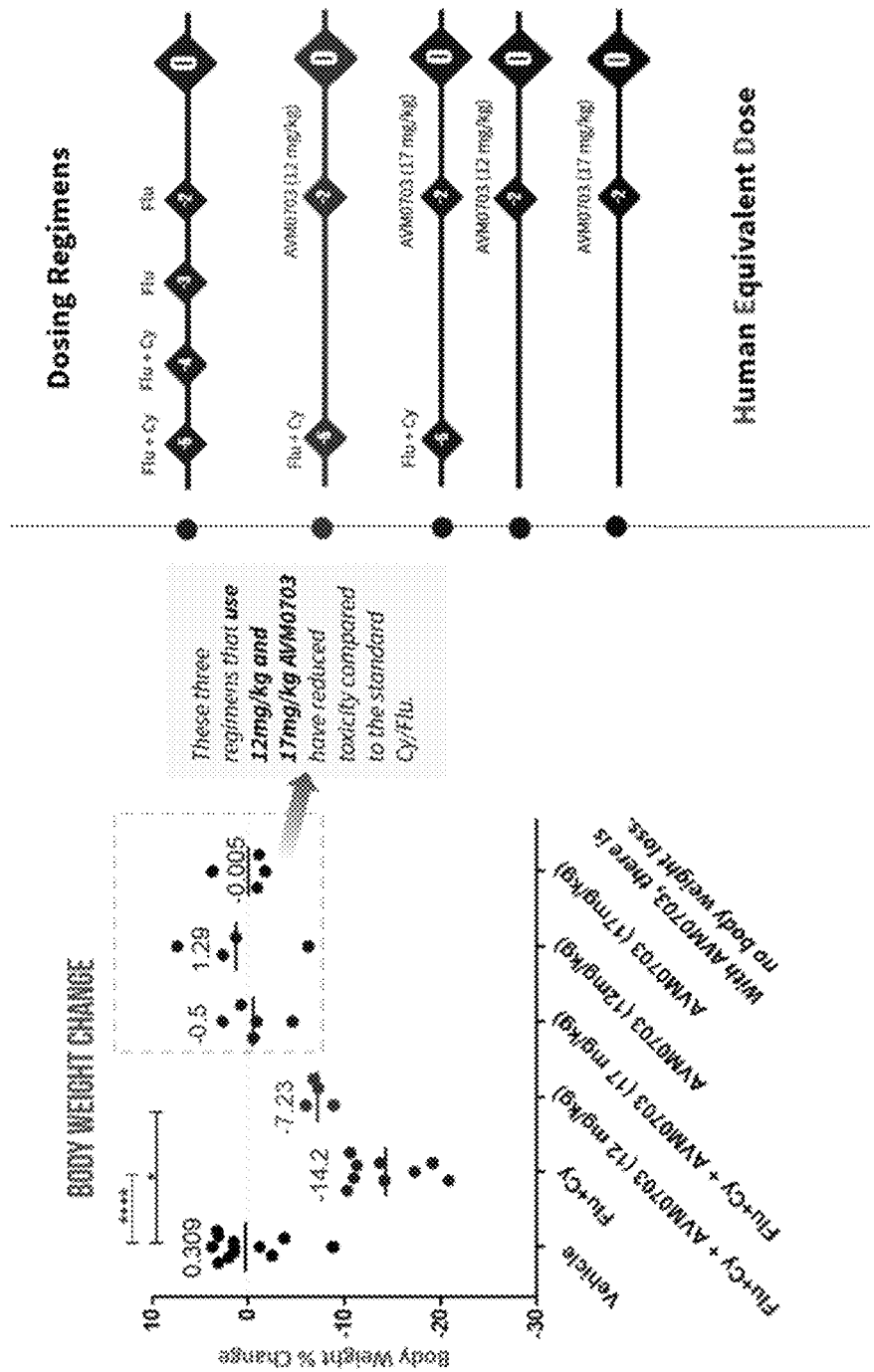
FIG. 25. A single dose of Cyclophosphamide 166 mg/kg (500 mg/m2) and Fludarabine 10 mg/kg on day −5 combined with 12 mg/kg or 17-18 mg/kg dexamethasone base on day −2 spared body weight, a measure of toxicity, compared to 2 days of repeat Cyclophosphamide 166 mg/kg on day −5 and −4 and 4 days of Fludarabine 10 mg/kg on days −5, −4, −3, −2. Shown (left) are graphs of individual body weight differences and averages calculated by subtracting body weight 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+ Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)) from pretreatment body weights. The acute high dose dexamethasone group is not associated with body weight loss unlike the chemotherapy groups. Acute high dose dexamethasone therefore provides a similar lymphodepletion effect as chemotherapy but with no associated toxicity. Also shown (right) is a representation of the dosing schedules in these regimens.

Example 4—Comparison of Acute 12 mg/kg and 17.5 mg/kg Dexamethasone Base HED to a Standard Cy (Cyclophosphamide) Flu (Fludarabine) Chemotherapy Regimen Dexamethasone base was administered by oral gavage to adult male mice at 12 mg/kg or 17.5 mg/kg HED on day −2. To another group of mice Cy was administered IP at 166 mg/kg (HED 500 mg/m2) on day −5 and day −4 and Fludarabine 10 mg/kg (HED 30 mg/m2) on days −5, −4, −3, −2. To a third group of mice Cy was administered IP at 166 mg/kg (HED 500 mg/m2) on day −5 and Fludarabine 10 mg/kg (HED 30 mg/m2) on days −5, then 12 mg/kg or 17.5 mg/kg HED dexamethasone base was administered orally on day −2. CBC and flow cytometry results are shown in FIGS. 19-24, and body weights are shown in FIG. 25.

Figure 23:
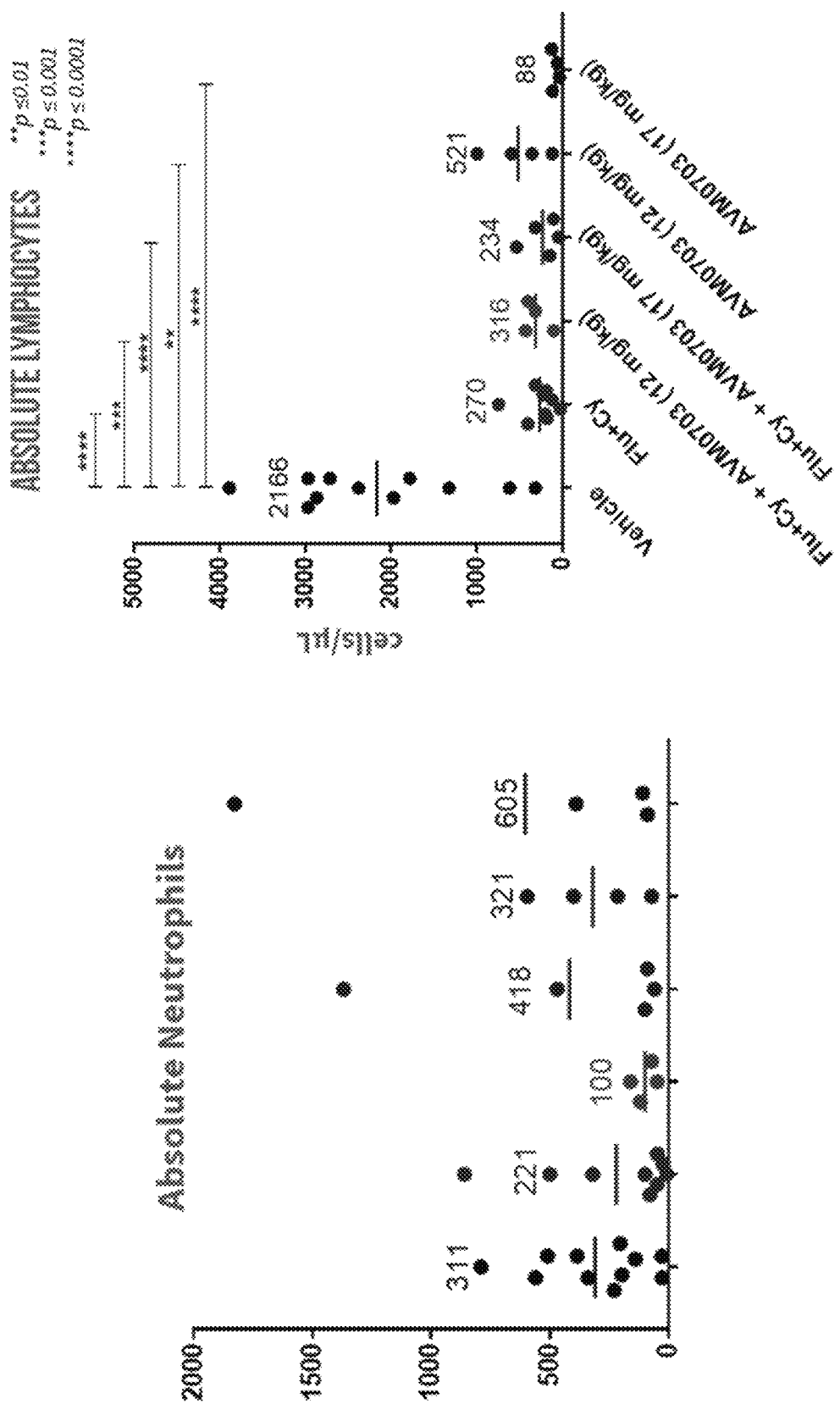
FIG. 23. A single dose of Cyclophosphamide 166 mg/kg (HED 500 mg/m2) and Fludarabine 10 mg/kg on day −5 combined with 12 mg/kg or 17-18 mg/kg dexamethasone base on day −2 equivalently lymphodepleted absolute lymphocytes, but spared neutrophils, compared to 2 days of repeat Cyclophosphamide 166 mg/kg on day −5 and −4 and 4 days of Fludarabine 10 mg/kg (HED 30 mg/m2) on days −5, −4, −3, −2. Shown are graphs of individual absolute neutrophils (left) and absolute lymphocytes (right) and averages measured by complete blood counts 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+ AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)). On both the neutrophil plot (left) and the lymphocyte plot (right), the 12 mg/kg or 17-18 mg/kg dexamethasone base data are shown in the right-hand columns of each (relative counts are '321', '605', '521' and '88').
Figure 24:
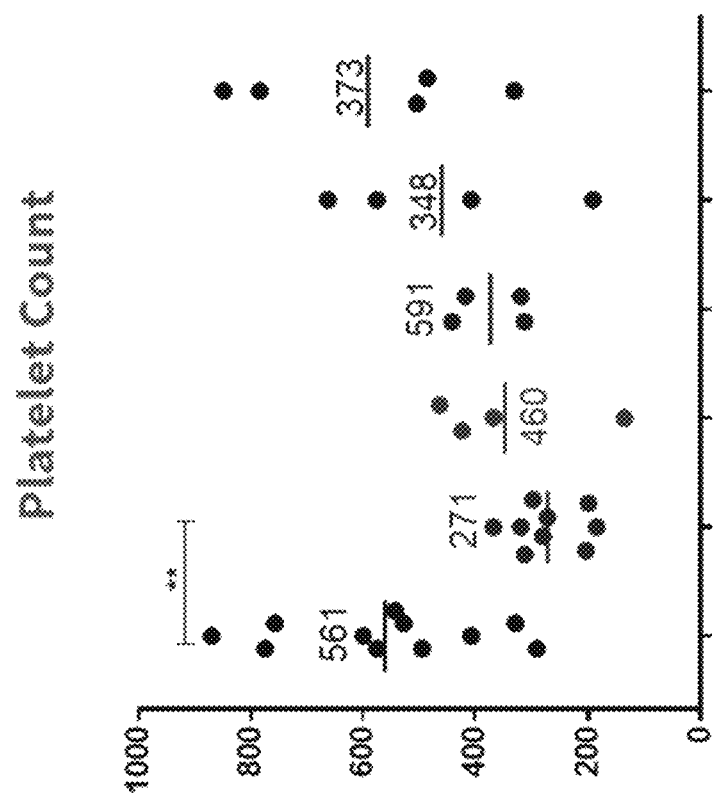
FIG. 24. A single dose of Cyclophosphamide 166 mg/kg (500 mg/m2) and Fludarabine 10 mg/kg (HED 30 mg/m2) on day −5 combined with 12 mg/kg or 17-18 mg/kg dexamethasone base on day −2 spared red blood cells (RBCs) and platelets. Shown are graphs of individual absolute platelet and absolute RBCs and averages measured by complete blood counts 48 hours after mice were treated IP with PBS (Vehicle), or with repeat IP Cyclophosphamide 166 mg/kg on day −5 and −4 and 4 days of IP Fludarabine 10 mg/kg (HED 30 mg/m2) on days −5, −4, −3, −2 (Flu+ Cy), or with a single IP dose of Cyclophosphamide 166 mg/kg (HED 500 mg/m2) and IP Fludarabine 10 mg/kg both on day −5 and then with oral 12 mg/kg or 17-18 mg/kg dexamethasone base on day −2 (Flu+Cy+AVM0703 (12 mg/kg); Flu+Cy+AVM0703 (17 mg/kg)), or with oral 12 mg/kg or 17-18 mg/kg dexamethasone base (AVM0703 (12 mg/kg); AVM0703 (17 mg/kg)). On both the RBC plot (left) and the platelet plot (right), the 12 mg/kg or 17-18 mg/kg dexamethasone base data are shown in the right-hand columns of each (relative counts are '10', '10', '348' and '373').
Figure 24:
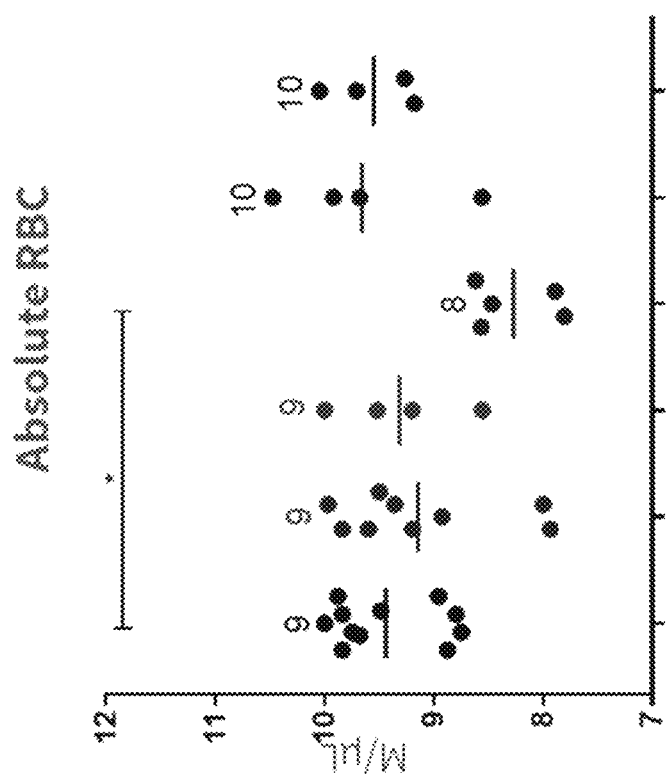

Dexamethasone base 12 mg/kg or 17.5 mg/kg HED given between 12-72 hours before blood draw leads to a comparable lymphodepletion profile compared to standard 2 day Cy with 4 day Flu, as does the combination of a single Cy on day −5 and a single Flu on day −5 with 12 mg/kg dexamethasone HED on day −2 (FIG. 23). The single Cy and single Flu dose can be administered on day −6, day −4, or day-3 with equal effect. The lymphodepletion profile of dexamethasone alone may be preferable because absolute lymphocytes are not depleted as dramatically as with CyFlu, and the degree of lymphodepletion may be related to neuroedema when adoptive cell therapy is given after CyFlu.

The standard repeat CyFlu regimen significantly reduced body weight as a general measure of toxicity, while 12 mg/kg or 17.5 mg/kg dexamethasone base HED did not impact body weight. The combination of one Cy and one Flu dose on day −5 with 12 mg/kg dexamethasone HED impacted body weight significantly less than the standard CyFlu regimen, while the combination of one Cy and one Flu dose on day −5 with 17.5 mg/kg dexamethasone HED did not impact body weight (FIG. 25). This demonstrates that acute high dose dexamethasone has a lymphodepletion profile equivalent to standard chemotherapy based on Cyclophosphamide (Cy) and Fludarabine (Flu) but with no associated weight loss, confirming the safety of the dexamethasone formulation compared to chemotherapy.

Additionally, in a double-blind controlled horse trial with acute high dose dexamethasone, no adverse side effects were observed for out to 70 days.

Data collected to date suggest that acute high dose dexamethasone presents with a safety profile consistent with that of approved DSP products. The proposed doses of acute high dose dexamethasone (HED 15-26 mg/kg) are equivalent or less than the cumulative doses of DSP that are used safely and effectively for pulse therapy daily for up to 5 days for a variety of conditions, and DSP has been well tolerated in physician initiated high-dose pulse therapy clinical use (Han et al, 2014; Annane et al, 2004; Ayache et al, 2014). A preliminary study performed on a small number of human osteoarthritis patients revealed that acute high dose dexamethasone elevates levels of plasma IL-2 and IL-15 cytokines, without affecting the concentration of pro-inflammatory cytokines (e.g. IL-6), as seen after chemotherapy regimens (U.S. Pat. No. 9,855,298B2). A full analysis of clinical chemistries in mice treated with acute high dose dexamethasone at increasing HED doses (6-12 mg/kg) showed that acute oral doses are safe and do not elevate clinical chemistry levels out of normal range including cholesterol and total protein. Moreover, while chronic low doses of DSP have been shown to cause undesirable side effects, including weight gain and glucose increase (Ferris & Kahn, 2012), the glucose level after acute high dose dexamethasone has been found not elevated over the normal range. Altogether, the lymphodepleting activity of acute high dose dexamethasone and its safe profile strongly support its use as immunologic reset treatment for autoimmune diseases with efficacy comparable to chemotherapy.

Other standard chemotherapeutic regimens that can be given as a single dose(s) on day −1 or day −2 or day −3 or day −4 or day −5 and be combined with Dexamethasone between about 3 to about 12 mg/kg on day −2 include: Cy 120 mg/kg and Flu 75 mg/m2; 30 mg/m2 flu and 50 mg/kg Cy and 200 cGy TBI; Cy 1500 mg/m2 and Bendamustine 120 mg/m2; Cy between about 300 mg/m2 and about 2300 mg/m2; Flu between about 10 mg/m2 and about 900 mg/m2; Cy 600 mg/m2 and Flu 30 mg/m2; Busulfan and Melphalan and Flu; Busulfan (dose adjusted according to weight) and Thiotepa (10 mg/kg) and Fludarabine (160 mg/m2); Flu 30 mg/m2 and Cy 300 mg/m2 and Mensa 300 mg/m2; Flu 30 mg/m2 and Cy 60 mg/m2 and Alemtuzumab 0.2 mg/kg.

Example 5—Treatment of Patients with Autoimmune Diseases

A patient with an autoimmune disease such as, but not limited to: SLE, psoriasis, rheumatoid arthritis, sporiatic arthritis, type I diabetes, multiple sclerosis, Sjogren's Syndrome, scleroderma, Grave's Disease, Hashimoto's thyroiditis, Celiac Disease, Addison's Disease, Myasthenia Gravis, Autoimmune hepatitis, Antiphospholipid syndrome, biliary cholangitis, can be treated with a glucocorticoid immune suppressant, or with dexamethasone dose. Acute high dose dexamethasone (as base) doses range from about 15 mg/kg to about 26 mg/kg, with doses between about 15 mg/kg and about 21 mg/kg being preferred.

B lymphocyte numbers are reduced by greater than 90% with acute high dose dexamethasone doses, and as memory B cells make up approximately 50% of the B cell compartment in people over age 20, memory B cell populations are also reduced by greater than 90%. The patient's autoimmune attacking B cells have apoptosed and the patient ceases to have active self-immune attacks. The patient's physical symptoms are improved or eliminated. Remission from the autoimmune disease lasts indefinitely in most patients, however, should the patient relapse then a repeat dose of the glucocorticoid immune suppressant, dexamethasone doses, or antagonist to CD26 can be administered. Repeat treatments can occur as often as once per month if necessary, but preferably not more than one a year, and most preferably not more than once every 5 years.

Example 6—Treatment of Residual HIV

A patient with residual HIV is treated with glucocorticoid immune suppressant, or with dexamethasone. Acute high dose dexamethasone (as base) doses range from about 15 mg/kg to about 26 mg/kg, with doses between about 15 mg/kg and about 21 mg/kg being preferred. The treatment eliminates the niches in the spleen where HIV hides and sends the infected T cells into the circulation where they can be killed by standard HIV therapies that include antiretroviral drugs, including but not limited to nucleoside reverse transcriptase inhibitors (NTRIs), non-nucleoside reverse transcriptase inhibitors (NNRTIs), protease inhibitors (PIs), fusion and entry inhibitors, pharmacokinetic enhances and integrase strand transfer inhibitors (INSTIs).

Example 7—Treatment of Germinal Center Lymphomas, for Example Burkitts Lymphoma A patient with a germinal center lymphoma such as but not limited to Burkitt's Lymphoma or diffuse large B-cell lymphoma (DLBCL) is treated with glucocorticoid immune suppressant, or with dexamethasone. Acute high dose dexamethasone (as base) doses range from about 15 mg/kg to about 26 mg/kg, with doses between about 15 mg/kg and about 21 mg/kg being preferred. The treatment eliminates the niches in the spleen where the germinal center lymphomas bind and sends the cells into the circulation where they can be eliminated more completely, or with lower doses, of standard chemotherapy such as R-CHOP, or by antibodies to CD20 such as Rituxan, Bexxar, or Zevalin, or by antibodies to CD22 or CD70 such as Lymphocide or Vorsetuzumab mafodotin, or by Bcl-2 inhibitors such as Oblimersen sodium, ABT-737 (oral form navitoclax, ABT-263), or Fenretinide, or by Syk inhibitors such as Fostamatinib or Tamatinib, or by proteasome inhibitors such as Bortezomib (Velcade), or COMPADME, CODOX-M/IVAC. Relapse rates are reduced and disease free survival rates are increased.

Example 8—Conversion of a Dexamethasone Dose to an Equivalent Dose of Another Glucocorticoid To calculate the equivalent dosing for another glucocorticoid, the dose of dexamethasone is entered into a publicly available glucocorticoid conversion calculator, preferably http://www.medcalc.com. Then the total dosing is determined based on the half-life of the glucocorticoid. For instance, 3 to 12 mg/kg dexamethasone converts to 19 to 75 mg/kg prednisone. Since prednisone's biologic half-life is about 20 hours, while dexamethasone's biologic half-life is about 36 to 54 hours. Therefore, prednisone would be dosed between 19 to 75 mg/kg every 24 hours for equivalent biologic dosing.

Example 9—Treatment of Patients with Autoimmune Diseases with Prednisone

A patient with an autoimmune disease such as, but not limited to: SLE, psoriasis, rheumatoid arthritis, sporiatic arthritis, type I diabetes, multiple sclerosis, Sjogren's Syndrome, scleroderma, Grave's Disease, Hashimoto's thyroiditis, Celiac Disease, Addison's Disease, Myasthenia Gravis, Autoimmune hepatitis, Antiphospholipid syndrome, biliary cholangitis, can be treated with acute high dose prednisone. Acute high dose prednisone doses range from about 19 mg/kg to about 150 mg/kg, with doses between about 56 mg/kg and about 112 mg/kg being preferred, with a repeat (second) administration of this dose 24 hours later and an optional repeat (third) administration of this dose 48-72 hours after the initial dose.

B lymphocyte numbers are reduced by greater than 90% with acute high dose prednisone doses, and as memory B cells make up approximately 50% of the B cell compartment in people over age 20, memory B cell populations are also reduced by greater than 90%. The patient's autoimmune attacking B cells have apoptosed and the patient ceases to have active self-immune attacks. The patient's physical symptoms are improved or eliminated. Remission from the autoimmune disease lasts indefinitely in most patients, however, should the patient relapse then a repeat dose of the prednisone can be administered. Repeat treatments can occur as often as once per month if necessary, but preferably not more than one a year, and most preferably not more than once every 5 years.

Example 10—Immunosuppressant Lymphodepletion in Female Mice 24-48 Hours after Acute Administration of Dexamethasone, with Neutrophil, RBC, Platelet and Stem Cell Sparing Properties Preliminary dose escalation studies performed in naïve mouse and rat models showed that administration of high-dose dexamethasone results in complete lymphodepletion. High-doses of dexamethasone were able to induce ~98% reduction in CD4+, CD8+, Tregs and B cells population measured 48 hours after administration, supporting rapid ablation of autoimmune pathophysiologic substrates. Early stage validation showed that acute high dose dexamethasone has 2-3 hour half-life by pharmacokinetic and a pharmacodynamics half-life of 4-5 days, which exclude prolonged immune suppression. In addition, oral dosing of acute high dose dexamethasone has comparable effects to IV dosing, which supports the use of acute high dose dexamethasone as a single oral treatment.

Oral acute administration of dexamethasone to C57B1 female mice at HED of 12 mg/kg, HED 15 mg/kg, 18 mg/kg demonstrated that female mice were less sensitive to dexamethasone base with lymphoablation not completely evident until doses above 18 mg/kg.

Acute high dose dexamethasone activates receptor-mediated apoptosis via the caspase pathway and lympho-depletes or lympho-ablates all lymphocytes depending on the dose used. As expected from its receptor-mediated mode of action, dexamethasone induces lymphodepletion sparing neutrophils, platelets, and Red Blood Cells (RBCs) due to the lack of or due to different glucocorticoid receptors on these cells. A tendency to elevate neutrophil counts above placebo in both peripheral blood and bone marrow was observed with high doses of dexamethasone, supporting possible protection against infections during lymphodepletion treatments.

The non-myeloablative regimen represented by acute high dose dexamethasone could, therefore, eliminate the need for transfusions of stem cells for hematopoietic recovery after immune-reset.

REFERENCES

A number of publications are cited above in order to more fully describe and disclose the invention and the state of the art to which the invention pertains. Full citations for these references are provided below:

Aker, A. M. et al. Phenols and parabens in relation to reproductive and thyroid hormones in pregnant women. *Environ. Res.* 151, 30-37 (2016)

Alexander, T. et al. Hematopoietic stem cell therapy for autoimmune diseases—Clinical experience and mechanisms. *J. Autoimmun.* 92, 35-46 (2018).

American Diabetes Association. Diagnosis and classification of diabetes mellitus. *Diabetes Care* 37 Suppl 1, S81-90 (2014)

American Diabetes Association. Type 1 Diabetes. (2018)

Atkinson, M. A., Eisenbarth, G. S. & Michels, A. W. Type 1 diabetes. *Lancet* (London, England) 383, 69-82 (2014) autoimmune disease. Nat Rev Immunol; 1:147-153 (2001)

Autoimmune disease: Updates from Europe and the United States. Biol Blood Marrow Transplant; 16(1 Suppl): S48-S56. doi:10.1016/j.bbmt.2009.10.034 (2010)

Baraldo, S., Kim Lokar Oliani, Graziella Turato, Renzo Zuin and Marina Saetta, "The Role of Lymphocytes in the Pathogenesis of Asthma and COPD", Current Medicinal Chemistry 14: 2250. (2007)

Bone, R. N. & Evans-Molina, C. Combination Immunotherapy for Type 1 Diabetes. *Curr. Diab. Rep.* 17, 50 (2017)

Broder, M. S. et al. The Cost of Hematopoietic Stem-Cell Transplantation in the United States. *Am. Heal. drug benefits* 10, 366-374 (2017).

Burger, J. A. & Montserrat, E., Coming full circle: 70 years of chronic lymphocytic leukemia cell redistribution, from glucocorticoids to inhibitors of B-cell receptor signaling; Blood 2013 vol. 121 no. 9 1501-1509, doi: https://doi.org/10.1182/blood-2012-08-452607 (2013).

*Burkitt's Lymphoma National Treatment Guidelines*. Health, IMA World. 2009

Burkit, D. *A sarcoma involving the jaws in African children*. The British Journal of Surgery., Vols. 46 (197): 218-23 (1958)

Cantu-Rodriguez, 0. G. et al. Long-Term Insulin Independence in Type 1 Diabetes Mellitus Using a Simplified Autologous Stem Cell Transplant. *J. Clin. Endocrinol. Metab.* 101, 2141-2148 (2016)

Couri, C. E. B., Malmegrim, K. C. R. & Oliveira, M. C. New Horizons in the Treatment of Type 1 Diabetes: More Intense Immunosuppression and Beta Cell Replacement. *Front. Immunol.* 9, 1086 (2018).

Daikeler, T., Tichelli, A. & Passweg, J. Complications of autologous hematopoietic stem cell transplantation for patients with autoimmune diseases. *Pediatr. Res.* 71, 439-444 (2012).

Darbre, P. D. & Harvey, P. W. Parabens can enable hallmarks and characteristics of cancer in human breast epithelial cells: a review of the literature with reference to new exposure data and regulatory status. *J. Appl. Toxicol.* 34, 925-938 (2014)

DeFranco, A. L. Germinal centers and autoimmune disease in humans and mice. *Immunol. Cell Biol.* 94, 918-924 (2016)

Fauci AS. Mechanisms of corticosteroid action on lymphocyte subpopulations. II. Differential effects of in vivo hydrocortisone, prednisone and dexamethasone on in vitro expression of lymphocyte function. Clinical and Experimental Immunology; 24(1):54-62 (1976)

Flammer, J. R. & Rogatsky, I. Minireview: Glucocorticoids in autoimmunity: unexpected targets and mechanisms. *Mol. Endocrinol.* 25, 1075-1086 (2011)

Henig, I. & Zuckerman, T. Hematopoietic stem cell transplantation-50 years of evolution and future perspectives. *Rambam Maimonides Med. J.* 5, e0028 (2014).

Kim, J. H., Jin, S.-M., Kim, H. S., Kim, K.-A. & Lee, M.-S. Immunotherapeutic treatment of autoimmune diabetes. *Crit. Rev. Immunol.* 33, 245-281 (2013)

Loh, Y. et al. Development of a secondary autoimmune disorder after hematopoietic stem cell transplantation for autoimmune diseases: role of conditioning regimen used. *Blood* 109, 2548-2643 (2007).

Lu, Y., Suzuki, J., Guillioli, M., Umland, O., & Chen, Z. Induction of self-antigen-specific Foxp3+ regulatory T cells in the periphery by lymphodepletion treatment with anti-mouse thymocyte globulin in mice. *Immunology* 134, 50-59 (2011)

Magdalena, W. et al. Lack of persistent remission following initial recovery in patients with type 1 diabetes treated with autologous peripheral blood stem cell transplantation. *Diabetes Res. Clin. Pract.* (2018). doi:10.1016/j.diabres.2018.07.020

Malmegrim, K. C. R. et al. Immunological Balance Is Associated with Clinical Outcome after Autologous Hematopoietic Stem Cell Transplantation in Type 1 Diabetes. *Front. Immunol.* 8, 167 (2017)

Medicines Agency, E. Benzyl alcohol and benzoic acid group used as excipients. (2017)

Menke, A. et al. The prevalence of type 1 diabetes in the United States. *Epidemiology* (Cambridge, Mass.) 24, 773-774 (2013)

Orem, J., et al. *Burkitt's Lymphoma in Africa, a Review of the Epidemiology and Etiology*. s.l.: African Health Sciences, Vols. 7.3: 166-175 (2007)

Pallera, A. M. & Schwartzberg, L. S. Managing the toxicity of hematopoietic stem cell transplant. *J. Support. Oncol.* 2, 223-228-247 (2004).

Pasricha, J. Current regimen of pulse therapy for pemphigus: Minor modifications, improved results. *Indian J Dermatol Venereol Leprol* 74; 3, pp 217-221 (2008)

Patt H, Bandgar T, Lila A, Shah N. Management issues with exogenous steroid therapy. Indian Journal of Endocrinology and Metabolism. 17(Suppl 3):5612-5617. doi: 10.4103/2230-8210.123548 (2013)

Peng, B.-Y. et al. Addressing Stem Cell Therapeutic Approaches in Pathobiology of Diabetes and Its Complications. *J. Diabetes Res.* 2018, U.S. Pat. No. 7,806,435 (2018)

Ponchel et al., Interleukin-7 deficiency in rheumatoid arthritis: consequences for therapy-induced lymphopenia. *Arthritis Res Ther,* 7:R80-R92 (DOI 10.1186/ar1452) (2005)

Savage, J. H., Matsui, E. C., Wood, R. A. & Keet, C. A. Urinary levels of triclosan and parabens are associated with aeroallergen and food sensitization. *J. Allergy Clin. Immunol.* 130, 453-60.e7 (2012)

Schwartz

Serafin, V., Capuzzo, G., Milani, G., Minuzzo, S. A., Pinazza, M., Bortolozzi, R., Bresolin, S., Porcù, E., Frasson, C., Indraccolo, S., Basso, G., & Accordi, B. Glucocorticoid resistance is reverted by LCK inhibition in pediatric T-cell acute lymphoblastic leukemia. Blood, 130(25), 2750-2761 (2017)

Shlomchik M J, Craft J E, Mamula M J. From T to B and back again: positive feedback in systemic Snarski, E. et al. Immunoablation and autologous hematopoietic stem cell transplantation in the treatment of new-onset type 1 diabetes mellitus: long-term observations. *Bone Marrow Transplant.* 51, 398-402 (2016)

Spanier, A. J., Fausnight, T., Camacho, T. F. & Braun, J. M. The associations of triclosan and paraben exposure with allergen sensitization and wheeze in children. *Allergy asthma Proc.* 35, 475-481 (2014)

Sullivan, K., Muraro, P., & Tyndall, A. Hematopoietic cell transplantation for

Swart, J. F. et al. Haematopoietic stem cell transplantation for autoimmune diseases. *Nat. Rev. Rheumatol.* 13, 244-256 (2017).

Thomas S L, Griffiths C, Smeeth L, Rooney C, Hall A J. Burden of Mortality Associated With Autoimmune Diseases Among Females in the United Kingdom. American Journal of Public Health. 100(11):2279-2287. doi: 10.2105/AJPH.2009.180273 (2010)

Thangavelu Gl, Parkman J C, Ewen C L, Uwiera R R, Baldwin T A, Anderson C C. Programmed death-1 is required for systemic self-tolerance in newly generated T cells during the establishment of immune homeostasis. Arthritis Res Ther. 7(1):R80-92. (2005)

U.S Department of Health and Human Services Food and Drug Administration Center for Drug Evaluation and Research (CDER) Guidance for Industry: Estimating the Maximum Safe Starting Dose in Initial Clinical Trials for Therapeutics in Adult Healthy Volunteers. *Pharmacology and Toxicology* July (2005)

Voltarelli, J. C. et al., Autologous nonmyeloablative hematopoietic stem cell transplantation in newly diagnosed type 1 diabetes mellitus. *JAMA* 297, 1568-1576 (2007).

Yan, S X et al., Prednisone treatment inhibits the differentiation of B lymphocytes into plasma cells in MRL/MpSlac-lpr mice, *Acta Pharmacologica Sinica* volume 36, pages 1367-1376 (2015).

Zwang Homeostatic expansion as a barrier to lymphocyte depletion strategies Curr Opin Organ Transplant. August; 19(4): 357-362 (2014)

The invention claimed is:

1. A method of treating a lymphocyte mediated disease in a subject, comprising administering a pharmaceutical composition comprising dexamethasone or betamethasone and one or more pharmaceutically acceptable carriers, preservatives, and/or chelating agents, to the subject at a dose of about 9 to about 26 mg/kg human equivalent dose (HED) of dexamethasone base,
    wherein administering the pharmaceutical composition depletes splenic, peripheral blood, thymic and bone marrow lymphocytes in the subject by at least 50%;
    wherein the method does not comprise co-administration of a chemotherapy agent; and
    wherein the lymphocyte mediated disease is not graft versus host disease (GVHD).

2. The method of claim 1, wherein the lymphocyte mediated disease is an autoimmune disease.

3. The method of claim 1, wherein the lymphocyte mediated disease is residual HIV disease.

4. The method of claim 1, wherein the lymphocyte mediated disease is a germinal center lymphoma.

5. The method of claim 1, wherein the lymphocyte mediated disease is an allergic disorder.

6. The method of claim 2, wherein the autoimmune disease is selected from Type 1 diabetes, multiple sclerosis, amyotrophic lateral sclerosis, scleroderma, pemphigus, and lupus.

7. The method of claim 1, wherein the pharmaceutical composition comprises a preservative, wherein the preservative is a sulfite.

8. The method of claim 1, wherein the pharmaceutical composition comprises a chelating agent, wherein the chelating agent is EDTA.

9. The method of claim 1, wherein the glucocorticoid is dexamethasone, wherein the dexamethasone is selected from dexamethasone base, dexamethasone sodium phosphate and dexamethasone acetate.

10. The method of claim 9, wherein the dexamethasone is dexamethasone sodium phosphate.

11. The method of claim 1, wherein the pharmaceutical composition is administered as a single acute dose or a total dose given over about a 72 hour period.

12. The method of claim 1, wherein the pharmaceutical composition is administered as an intravenous (IV) or oral dose.

13. The method of claim 1, wherein the pharmaceutical composition is an aqueous solution.

14. The method of claim 1, wherein the pharmaceutical composition is administered at a dose of at least about 9 mg/kg, at least about 10 mg/kg, at least about 11 mg/kg, at least about 12 mg/kg, at least about 15 mg/kg, at least about 18 mg/kg, or at least about 24 mg/kg of a human equivalent dose (HED) of dexamethasone base.

* * * * *